United States Patent
Hoegh et al.

(10) Patent No.: US 11,081,222 B2
(45) Date of Patent: Aug. 3, 2021

(54) OBSTRUCTIVE SLEEP APNEA TREATMENT SCREENING METHODS

(71) Applicant: LivaNova USA, Inc., Houston, TX (US)

(72) Inventors: Thomas B. Hoegh, Edina, MN (US); Daniel A. Parrish, Bloomington, MN (US)

(73) Assignee: LivaNova USA, Inc., Houston, TX (US)

( * ) Notice: Subject to any disclaimer, the term of this patent is extended or adjusted under 35 U.S.C. 154(b) by 1166 days.

(21) Appl. No.: 14/505,151

(22) Filed: Oct. 2, 2014

(65) Prior Publication Data

US 2015/0094962 A1    Apr. 2, 2015

Related U.S. Application Data

(60) Provisional application No. 61/885,991, filed on Oct. 2, 2013, provisional application No. 62/058,914, filed on Oct. 2, 2014.

(51) Int. Cl.

| | |
|---|---|
| *G06Q 50/00* | (2012.01) |
| *G16H 20/30* | (2018.01) |
| *G01N 33/49* | (2006.01) |
| *G01N 33/80* | (2006.01) |
| *A61B 5/145* | (2006.01) |
| *A61B 5/00* | (2006.01) |
| *G16H 50/30* | (2018.01) |

(52) U.S. Cl.
CPC ......... *G16H 20/30* (2018.01); *A61B 5/14542* (2013.01); *A61B 5/4818* (2013.01); *A61B 5/686* (2013.01); *A61B 5/7275* (2013.01); *A61B 5/7282* (2013.01); *G01N 33/49* (2013.01); *G01N 33/80* (2013.01); *G16H 50/30* (2018.01)

(58) Field of Classification Search
CPC ........ A61B 5/08; A61B 5/4818; A61B 5/0878
USPC .................... 600/529, 410, 534, 300; 607/42
See application file for complete search history.

(56) References Cited

U.S. PATENT DOCUMENTS

| | | | | |
|---|---|---|---|---|
| 6,811,538 B2* | 11/2004 | Westbrook | ........... | A61B 5/0205 600/529 |
| 7,510,531 B2* | 3/2009 | Lee | ........ | A61B 5/0031 600/534 |
| 8,140,164 B2* | 3/2012 | Tehrani | ................ | A61N 1/3601 607/42 |
| 8,545,416 B1 | 10/2013 | Kayyali et al. | | |
| 8,983,572 B2* | 3/2015 | Ni | ........................ | A61B 5/0878 600/410 |

(Continued)

OTHER PUBLICATIONS ip.com search, Mar. 24, 2021 (Year: 2021).*

(Continued)

*Primary Examiner* — Dilek B Cobanoglu
(74) *Attorney, Agent, or Firm* — Foley & Lardner LLP

(57) ABSTRACT

Embodiments include a screening method for evaluating patient suitability for an implanted hypoglossal nerve stimulation (HGNS) device. The screening method evaluates blood oxygen data relating to respiratory events, with the blood oxygen data providing mean blood oxygen desaturation values for comparison to severity thresholds to identify patients who are likely or unlikely to benefit from the implantation of the HGNS device.

56 Claims, 31 Drawing Sheets

(56) References Cited

U.S. PATENT DOCUMENTS

| | | | |
|---|---|---|---|
| 2002/0165462 A1* | 11/2002 | Westbrook | A61B 5/0205 600/529 |
| 2007/0265506 A1* | 11/2007 | Wang | G06Q 50/24 600/300 |
| 2011/0061647 A1* | 3/2011 | Stahmann | A61B 5/0031 128/202.16 |
| 2011/0208539 A1* | 8/2011 | Lynn | G16H 50/70 705/2 |
| 2013/0060110 A1* | 3/2013 | Lynn | G16H 20/10 600/324 |
| 2013/0197376 A1 | 8/2013 | Alt et al. | |

OTHER PUBLICATIONS

International Search Report and Written Opinion for corresponding International Application No. PCT/US2014/058858, dated Dec. 9, 2014 (9 pages).

Office Action on EP Application No. 14790882.6 dated Aug. 12, 2019. 5 pages.

Examination Report issued in EP 14790882.6 dated Sep. 24, 2020.

* cited by examiner

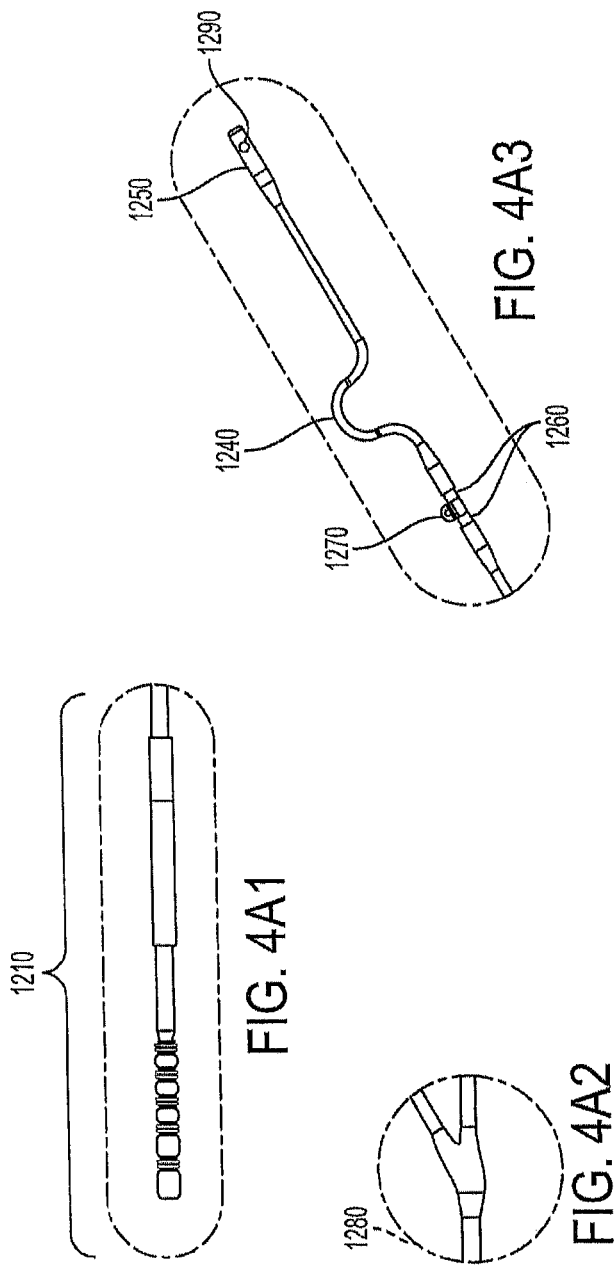

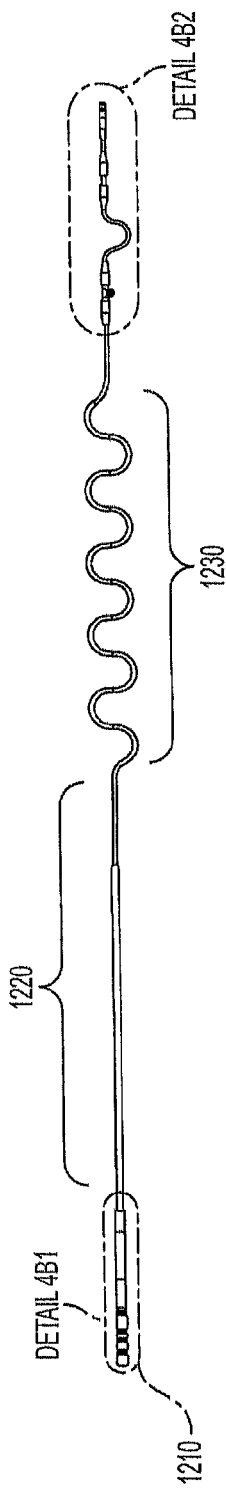
FIG. 4B
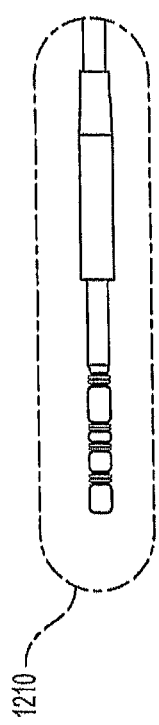
FIG. 4B1
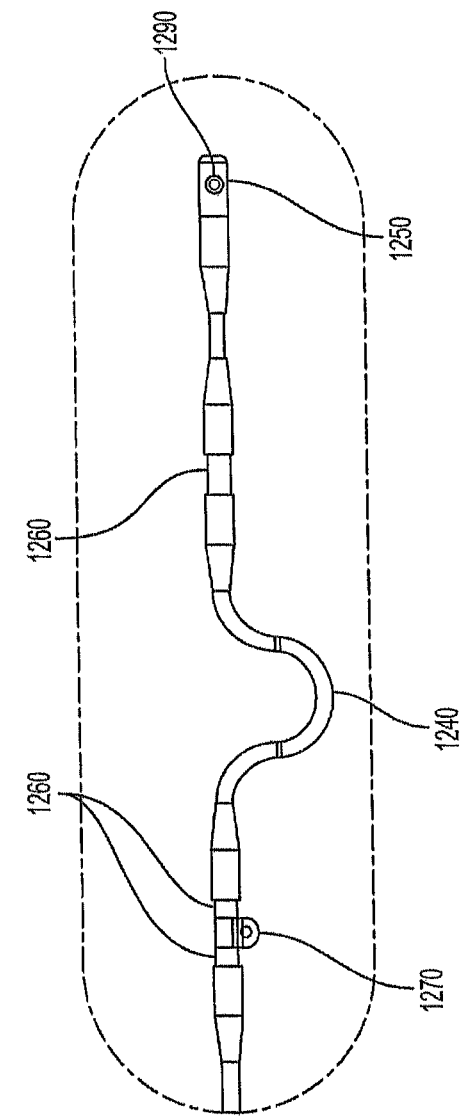
FIG. 4B2

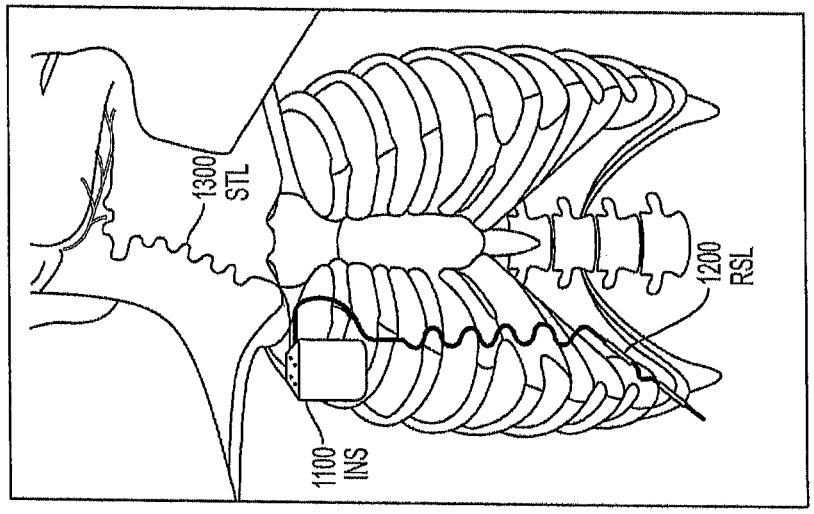
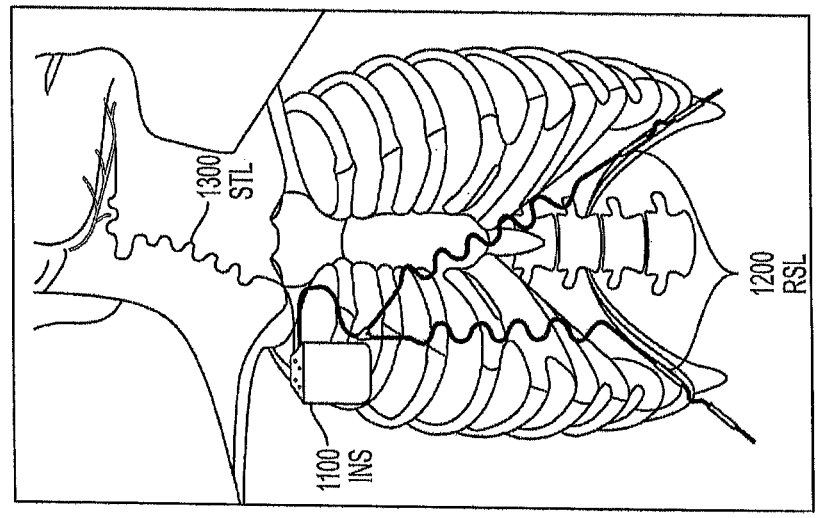
FIG. 4D
FIG. 4C

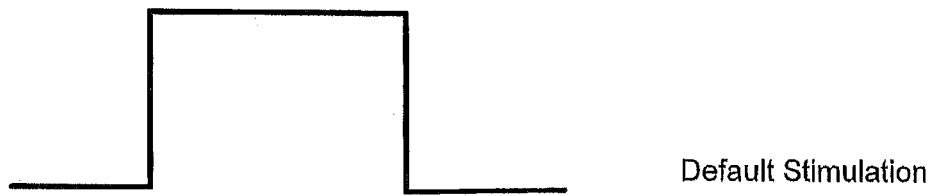
FIG. 6D — Default Stimulation
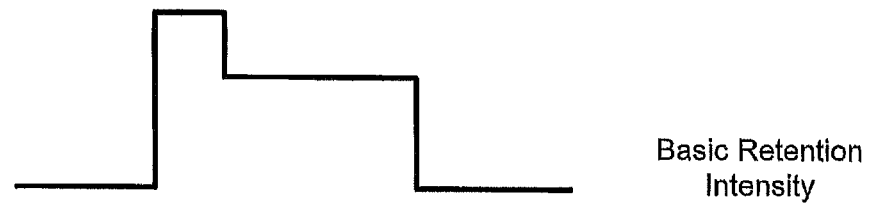
FIG. 6E — Basic Retention Intensity
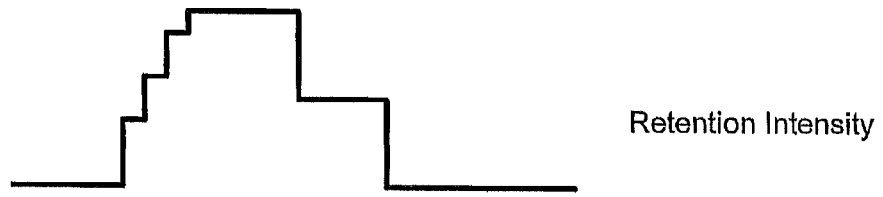
FIG. 6F — Retention Intensity
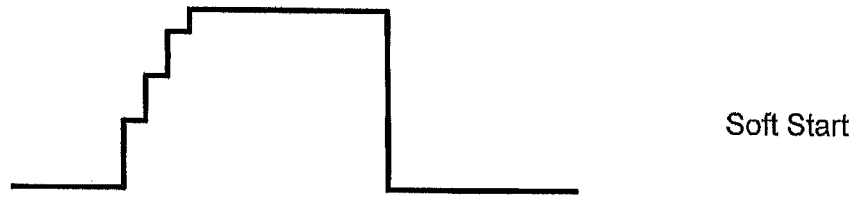
FIG. 6G — Soft Start
FIG. 6H — Nested Stimulation

OBSTRUCTIVE SLEEP APNEA TREATMENT SCREENING METHODS

RELATED APPLICATION(S)

This application claims priority to U.S. Provisional Application Nos. 61/885,991, filed Oct. 2, 2013, and 62/058,914, filed Oct. 2, 2014, the entire disclosures of which are hereby incorporated by reference in their entireties.

TECHNICAL FIELD

The embodiments described herein relate to devices, systems and associated methods for treating sleep disordered breathing. More particularly, the embodiments described herein relate to devices, systems and methods for treating obstructive sleep apnea.

BACKGROUND

Obstructive sleep apnea (OSA) is highly prevalent, affecting one in five adults in the United States. One in fifteen adults has moderate to severe OSA requiring treatment. Untreated OSA results in reduced quality of life measures and increased risk of disease including hypertension, stroke, heart disease, etc.

Continuous positive airway pressure (CPAP) is a standard treatment for OSA. While CPAP is non-invasive and highly effective, it is not well tolerated by patients. Patient compliance for CPAP is often reported to be between 40% and 60%.

Surgical treatment options for OSA are available too. However, they tend to be highly invasive (result in structural changes), irreversible, and have poor and/or inconsistent efficacy. Even the more effective surgical procedures may be undesirable because they usually require multiple invasive and irreversible operations, they may alter a patient's appearance (e.g., maxillo-mandibular advancement), and/or they may be socially stigmatic (e.g., tracheostomy).

U.S. Pat. No. 4,830,008 to Meer proposes hypoglossal nerve stimulation as an alternative treatment for OSA. An example of an implanted hypoglossal nerve stimulator for OSA treatment is the Inspire™ technology developed by Medtronic, Inc. (Fridley, Minn.) and described in an eight patient human clinical study, the results of which were published by Schwartz et al. in *Therapeutic Electrical Stimulation of the Hypoglossal Nerve in Obstructive Sleep Apnea*, 127 ARCH OTOLARYNGOL HEAD NECK SURG 1216-1223 (2001) (hereinafter "Schwartz et al.") and by Eisele et al. The Inspire device includes an implanted neurostimulator, an implanted nerve cuff electrode connected to the neurostimulator by a lead, and an implanted intra-thoracic pressure sensor for respiratory feedback and timing of stimulation delivery. The Inspire device was shown to be efficacious (approximately 75% response rate as defined by a 50% or more reduction in RDI (Respiratory Disturbance Index) and a post RDI of 20) in the eight patient human clinical study. However, both study authors reported that only three of eight patients remained free from device malfunction, thus demonstrating the need for improvements.

SUMMARY

To address this and other unmet needs, the present disclosure provides, in exemplary non-limiting embodiments, devices, systems and methods for nerve stimulation for OSA therapy as described in the following detailed description. Potential screening methods can be utilized to increase the likelihood of therapeutic efficacy.

BRIEF DESCRIPTION OF THE DRAWINGS

It is to be understood that both the foregoing summary and the following detailed description are exemplary. Together with the following detailed description, the drawings illustrate exemplary embodiments and serve to explain certain principles. In the drawings:

FIG. 4A1 is a detailed perspective view of the proximal connector assembly of the respiration sensing lead shown in FIG. 4A.

FIG. 4A2 is a detailed perspective view of the bifurcation section of the respiration sensing lead shown in FIG. 4A.

FIG. 4A3 is a detailed perspective view of the contra-lateral distal body portion of the respiration sensing lead shown in FIG. 4A.

FIG. 4A4 is a detailed perspective view of the ipsi-lateral distal body portion in the respiration sensing lead shown in FIG. 4A.

FIG. 4B is a detailed perspective view of an alternative embodiment of the respiration sensing lead which may be used in the system shown in FIG. 1.

FIG. 4B1 is a detailed perspective view of the proximal connector assembly of the respiration sensing lead shown in FIG. 4B.

FIG. 4B2 is a detailed perspective view of the distal body portion of the respiration sensing lead shown in FIG. 4B.

FIG. 4C illustrates the implanted system shown in FIG. 1 with the respiration lead shown in FIG. 4A.

FIG. 4D illustrates the implanted system shown in FIG. 1 with the respiration lead shown in FIG. 4B.

FIGS. 6D, 6E, 6F, 6G, and 6H illustrate various stimulation pulse configurations for the implantable neurostimulator shown in FIG. 1, as may be used for therapy or sleep titration, for example.

DETAILED DESCRIPTION OF EXEMPLARY EMBODIMENTS

The following detailed description should be read with reference to the drawings in which similar elements in different drawings are numbered the same. The drawings, which are not necessarily to scale, depict illustrative embodiments and are not intended to limit the scope of the disclosure.

Overall System

Figure 1:
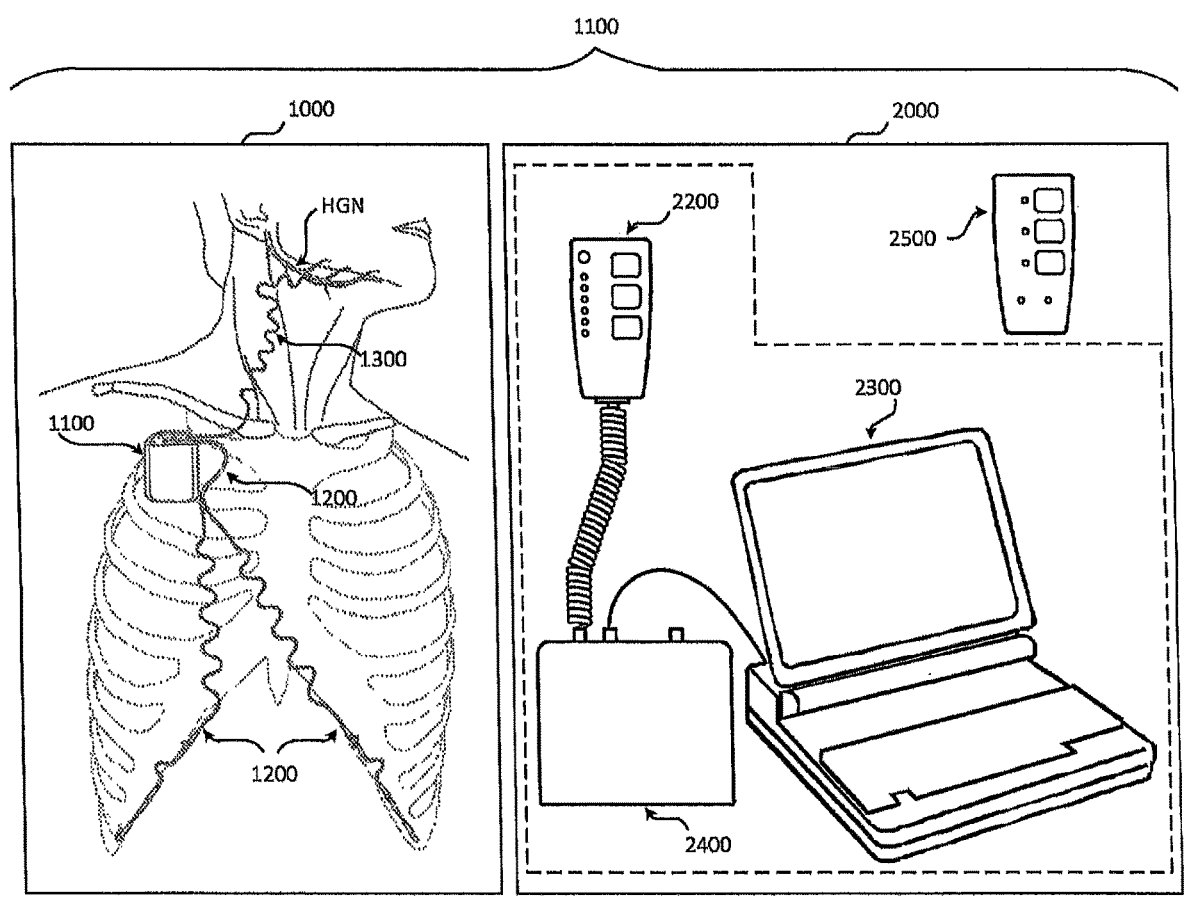
FIG. 1 is a schematic illustration of a system according to an embodiment of the present disclosure, including internal (chronically implanted) and external components.

FIG. 1 schematically illustrates an exemplary hypoglossal nerve stimulation (HGNS) system 100 comprising internal components 1000 and external components 2000. The HGNS system 100 may treat obstructive sleep apnea (OSA) by increasing neuromuscular activity to the genioglossus muscle via stimulation of the hypoglossal nerve (HGN), such as synchronous with inspiration, to mitigate upper airway collapse during sleep. Stimulation may be generated by an implantable neurostimulator (INS) 1100, for example synchronized with inspiration as measured by the respiration sensing lead (RSL) 1200 using bio-impedance, and delivered to the hypoglossal nerve by a stimulation lead (STL) 1300. A programmer system 2100 and a therapy controller 2500 may be wirelessly linked to the INS 1100. The programmer system 2100 may include a computer 2300, a programmer interface 2400, and a programmer head 2200. The programmer system 2100 may be used by the physician, a sleep lab technician, or care provider to control, monitor, and program the INS 1100 during surgery and/or therapy titration, and the therapy controller 2500 may be used by the patient or a care provider to control and monitor limited aspects of therapy delivery.

The implanted components 1000 of the HGNS system 100 may include the INS 1100, STL 1300, and RSL 1200. The INS may be designed to accommodate one STL 1300 and one RSL 1200. One STL 1300 may be used for unilateral implantation and unilateral hypoglossal nerve stimulation. Similarly, one RSL 1200 may be used for respiration detection. Alternative embodiments of the RSL 1200 are described below and may be substituted. Therefore, for purposes of illustration not limitation, the INS 1100 is shown with STL 1300 and a bifurcated RSL 1200.

The implanted components 1000 may be surgically implanted with the patient under general anesthesia. The INS 1100 may be implanted in a subcutaneous pocket inferior to the clavicle over the pectoralis fascia. The distal end of the STL 1300 (cuff 1350) may be implanted on the hypoglossal nerve or a branch of the hypoglossal nerve in the submandibular region, and the proximal end of the STL 1300 may be tunneled under the skin to the INS 1100. The RSL 1200 may be tunneled under the skin from the INS 1100 to the rib cage and placed on the costal margin. The INS 1100 of the exemplary embodiment detects respiration via the RSL 1200 using bio-impedance.

Stimulation Lead (STL)

Figure 2:
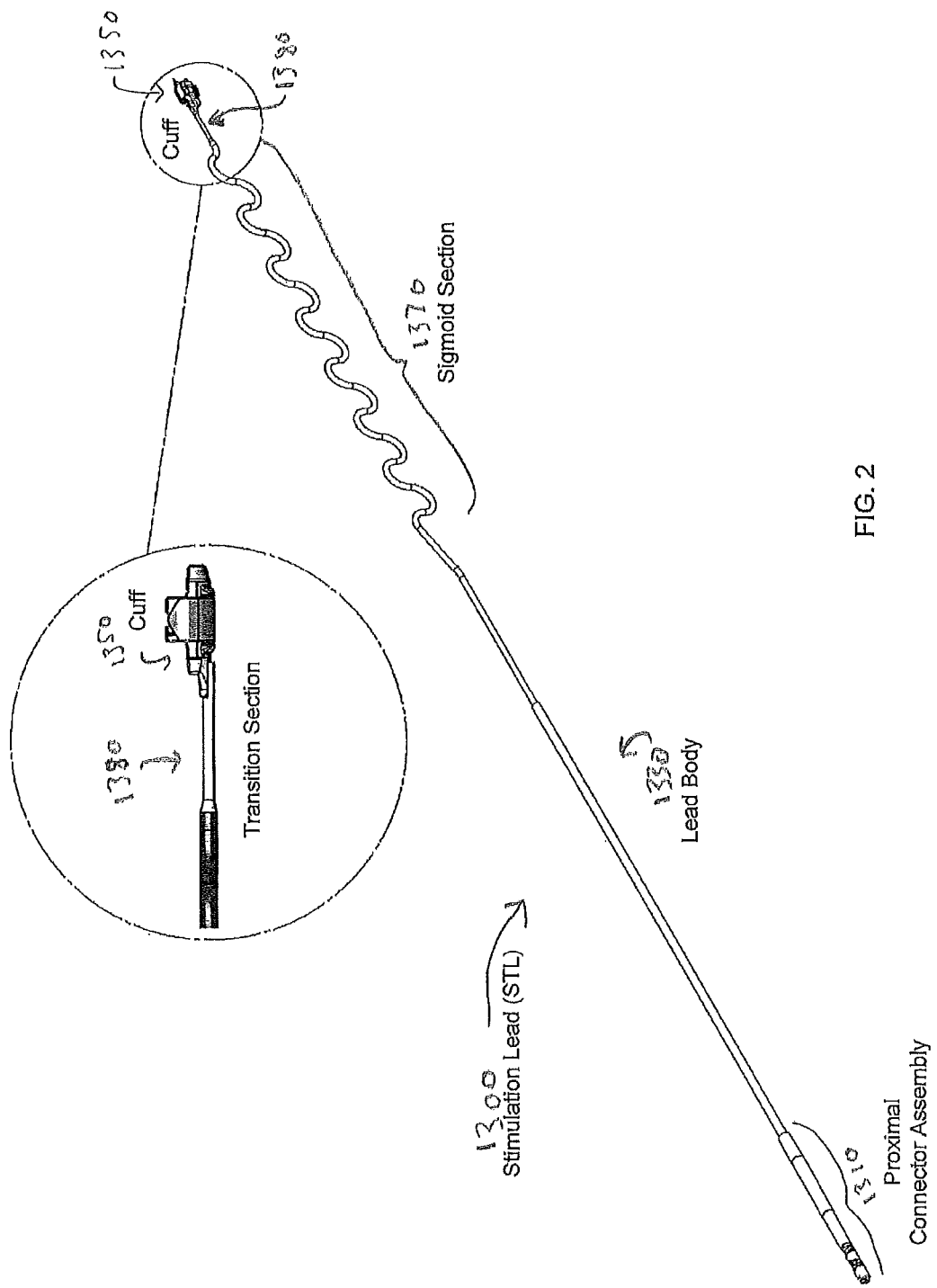
FIG. 2 is a perspective view of a stimulation lead for use in the system shown in FIG. 1, including a detailed view of the distal end of the stimulation lead.

FIG. 2 schematically illustrates the STL 1300 in more detail. The STL 1300 may be designed to deliver the stimulation signal from the INS 1100 to the hypoglossal nerve and may include a proximal connector assembly 1310, a main tubular body 1330, and a distal cuff 1350. The main tubular body of the STL may include a sigmoid shaped section 1370 and a distal flexible transition section 1380 proximal of the cuff. The STL may have a nominal outside diameter of 0.062 inches to have minimal cosmetic impact, and a nominal overall length of 17.7 inches (45 cm) (including cuff) to extend from the infraclavicular region (INS) to the submandibular region (hypoglossal nerve) and to accommodate anatomical variation.

The main tubular body 1330 of the STL 1300 may be designed to withstand gross neck movement as well as mandibular movement and hypoglossal nerve movement caused by talking, chewing, swallowing, etc. To survive in this high fatigue environment, the main tubular body 1330 may incorporate a highly compliant silicone jacket in the form of a sigmoid, and two conductors 1390 (one for cathode electrodes, one for anode electrodes), each comprising ETFE insulated MP35N multifilament cable disposed inside the jacket in the form of a bi-filar coil (not visible). This design may provide high fatigue resistance and three-dimensional flexibility (bending and elongation).

The proximal connector assembly 1310 may be designed to provide a reliable mechanical and electrical connection of the STL 1300 to the INS 1100. It may have a number of strain relief elements that enable it to withstand handling during insertion and removal from the INS 1100, as well as adverse conditions encountered when implanted. The connector assembly 1310 may include two in-line stainless steel ring contacts (one for each conductor 1390) and two silicone ring seals. STL proximal connector contacts 1310 may have a nominal outside diameter of about 0.122 inches. Set screws in the header of the INS 1100 may bear down on the contacts, and together with the ring seals, provide a sealed mechanical and electrical connection to the INS 1100. As an alternative, wound coil spring contacts may provide mechanical and electrical connections.

Figure 3A:
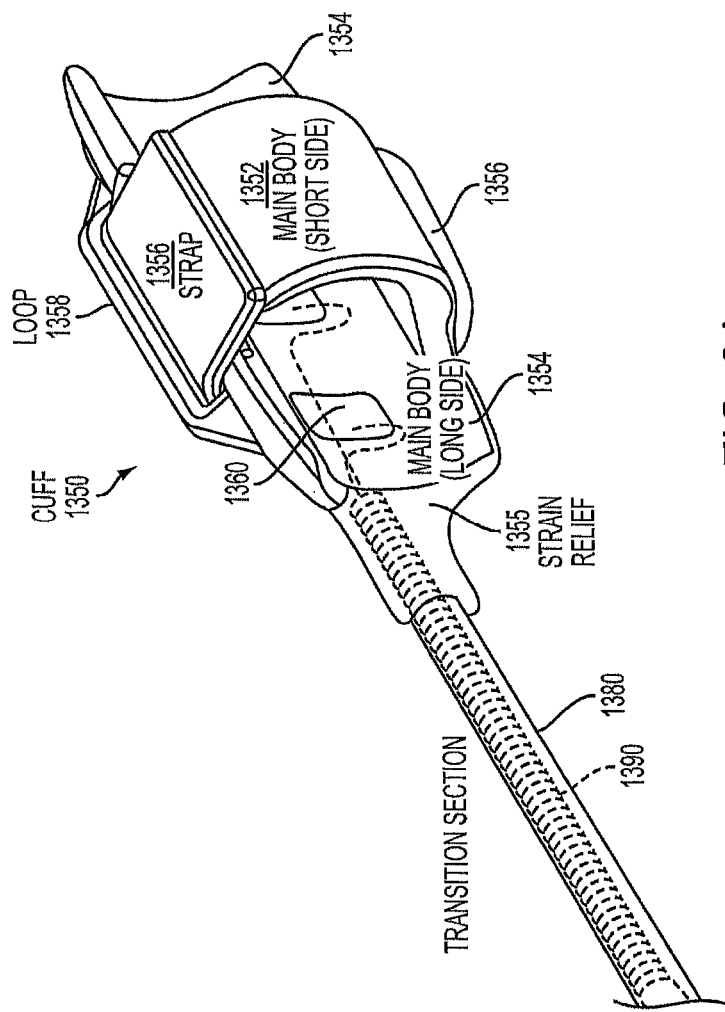
FIG. 3A is a detailed perspective view of the cuff of the stimulation lead shown in FIG. 2.
Figure 3B:
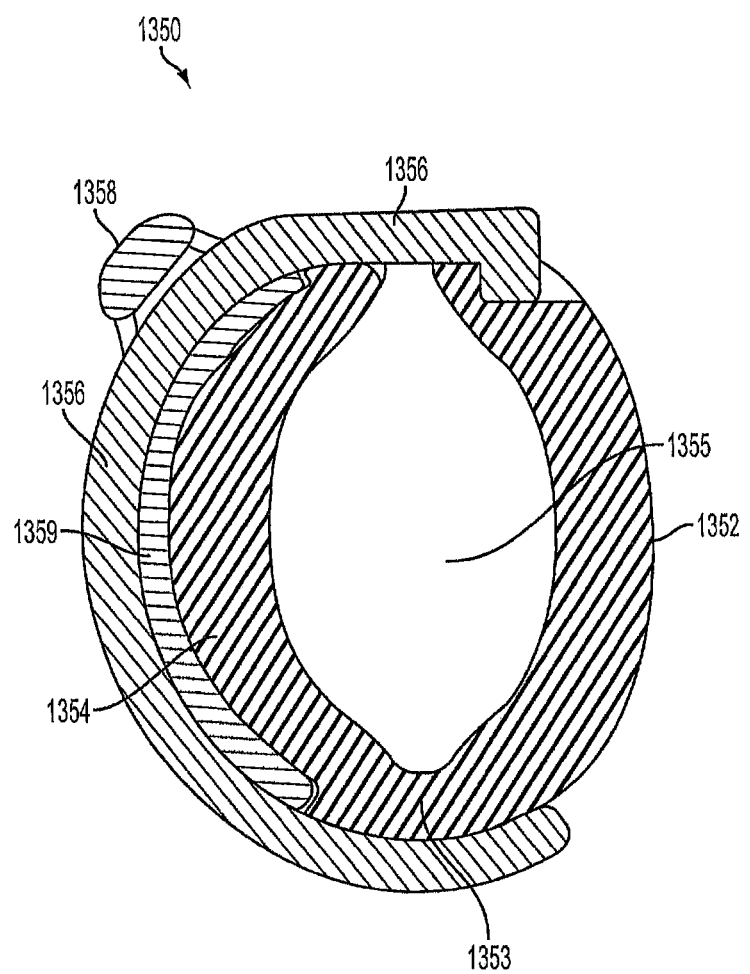
FIG. 3B is a lateral cross-sectional view of the cuff shown in FIGS. 2 and 3A.

More detailed views of the cuff 1350 are shown in FIGS. 3A and 3B, wherein FIG. 3A schematically illustrates the cuff 1350 in isometric view, and FIG. 3B schematically illustrates the cuff 1350 in cross-sectional view. The cuff 1350 may have a hinged oval-shaped silicone body (collectively 1352 and 1354) to define an oval lumen 1355 that may provide secure and gentle retention around the hypoglossal nerve. The cuff 1350 may be designed to fit the nerve very closely to minimize tissue growth between the electrode and nerve. The cuff 1350 may be designed to be self-sizing such that different nerve diameters may be accommodated safely. The self-sizing may safely adjust to larger sizes if swelling occurs. This may reduce the likelihood of nerved damage caused by unsafe pressures. Thus, the cuff may be available in two sizes to accommodate nerves of different diameter: a small size to accommodate nerves having a diameter of up to about 2.5-3.0 mm, and a large size to accommodate nerves having a diameter of up to 3.0-4.0 mm. At 3.0 mm nerve diameter, either size cuff may fit the nerve with minimal open space for tissue in-growth. Using a large cuff on a 2.5 mm nerve may allow clearance between the nerve and electrode which promotes capsule formation between the cuff and nerve. This may cause an increase in capture threshold but may not affect safety. Conversely, a small cuff placed on a large nerve may minimize electrode coverage around the nerve and may fall off with swelling. The short side 1352 (e.g., 4.0 mm long) of the cuff body may fit between nerve branches and connective tissue on the deep side of the nerve, thereby minimization nerve dissection. The long side 1354 (e.g., 10.0 mm long) of the cuff body may rest on the superficial side of the nerve (where few branches exist) and may be connected to the transition section 1380 of the main lead body 1330.

A silicone strap 1356 may be connected to and extend from the short side 1352 of the cuff body. A silicone top plate comprising an integral base portion 1359 and loop 1358 may be attached to and cover the exterior surface of the long side 1354 of the cuff body. The strap 1356 may freely slide through the loop 1358, and wrap around the long side 1354 of the cuff body. The strap 1356 may be removed from the loop 1358 for placement of the cuff 1350 around the nerve and reinserted into the loop 1358 to hold the cuff 1350 on the nerve. A mark may be disposed on the strap 1356 of the small size cuff to indicate that the cuff is too small and that a larger size cuff should be used if the mark does not pass through the loop 1358. The cuff body may readily expand along a hinge line 1353 (defined at the junction of the short side 1352 to the long side 1354) as well as other portions of the cuff 1350 structure. Expansion of the cuff body may accommodate nerves of different diameters and nerve swelling after implantation, while the strap 1356 may remains in the loop 1358 to retain the cuff 1350 on the nerve. In the event of excess nerve swelling (e.g., >50% increase in nerve diameter) or traction from the lead 1300 (e.g., as may accidentally occur during implantation), the strap 1356 may pull out of the loop 1358 and release the cuff 1350 from the nerve to minimize the potential for nerve damage.

The cuff body may carries four platinum-iridium electrodes 1360 (e.g., 2.0 mm$^2$ exposed area each for small cuff, 3.0 mm$^2$ exposed area each for large cuff), with one cathode electrode 1360 on the short side 1352, another cathode electrode 1360 (not visible) diametrically opposed on the long side 1354, and two anode electrodes 1360 guarding the cathode electrode 1360 on the long side 1354. This guarded dual cathode arrangement may provide a more uniform electrical field throughout the cross-section of the nerve while minimizing electrical field outside of the cuff. One conductor 1390 may be connected to the cathode electrode 1360 on the long side, to which the other cathode electrode 1360 on the short side may be connected by a jumper wire. Similarly, the other conductor 1390 may be connected to the distal anode electrode 1360, to which the proximal anode electrode 1360 may be connected by jumper wire. With this arrangement, the cathode electrodes may be commonly connected to one conductor 1390 and the anode electrodes may be commonly connected to the other conductor 1390.

With the exception of the metal electrode contacts in the cuff, all external surfaces of the STL 1300 exposed to the body when implanted may comprise implantable grade polymers selected from the following: silicone, and fully cured silicone adhesive. The metal electrode contacts in the cuff may comprise implantable grade platinum-iridium and may be secured to the silicone cuff body with silicone adhesive, for example.

Respiration Sensing Lead (RSL)

FIGS. 4A-4G schematically illustrates the respiration sensing lead (RSL) 1200 in more detail. The respiration sensing lead 1200 may be designed to measure bio-impedance and includes a proximal portion with a proximal connector assembly 1210, a proximal tubular body 1220 ending in a bifurcation section 1280, and ipsi-lateral and contra-lateral distal portions extending from the bifurcation section. Each distal portion may include a tubular body 1220, a proximal sigmoid section 1230, a distal sigmoid section 1240, one or more current injection ring electrodes 1250, one or more voltage sensing ring electrodes 1260, anchor tabs 1270, and a suture hole 1290 in the most distal ring electrodes. Alternatively, the ring electrodes 1250 and 1260 may be dual-function, such that each electrode may function as either a current emitting electrode or voltage sensing electrode. The ipsi-lateral distal portion may contain three ring electrodes, the most distal being a current emitting electrode 1250 and containing a suture hole 1290, and the other two electrodes being voltage sensing electrodes 1260. The contra-lateral distal portion may contain two ring electrodes, the distal being a current emitting electrode 1250 and containing a suture hole 1290, and the proximal a voltage sensing electrode. In at least one embodiment, the suture holes may be in the most distal ring electrodes since no wires pass through this point and because this may provides a robust anchor point for the electrode to be sutured on the costal margin muscle fascia. The RSL 1200 may have a nominal outside diameter of about 0.072 inches to have minimal cosmetic impact. The RSL proximal connector contacts 1210 may have a nominal outside diameter of about 0.122 inches (same as the STL proximal connector contacts 1310). The distal ring electrodes (here, current emitting electrodes 1250), may also have a nominal outside diameter of 0.122 inches. This uniformity in diameters may allow the same lead carrier 3100 to place both STL 1300 and RSL 1200 leads for tunneling.

The distance from the tip of the proximal connector 1210 to the bifurcation section 1280 may have an overall length of 8.9 inches (22.5 cm). The distance from the bifurcation section 1280 to the ipsi-lateral proximal anchor tab 1270 may be 9.6 inches (24.4 cm) unstretched and 12.2 inches (31 cm) stretched. The distance from the bifurcation section 1280 to the contra-lateral proximal anchor tab 1270 may be 13.5 inches (34.3 cm) unstretched and 16.1 inches (41 cm) stretched. The distance from the proximal anchor tab 1270 to the distal suture hole 1290 may be 2.8 inches (7 cm) unstretched and 3.1 inches (8 cm) stretched on both the contra-lateral and ipsi-lateral distal portions. The RSL 1200 may extend from the infraclavicular region (where the INS 1100 is implanted) to the ipsi-lateral and contra-lateral thorax where the RSL 1200 may be implanted to accommodate anatomical variation.

The bifurcated RSL 1200 design may enable one RSL 1200 to sense bio-impedance on the contra-lateral and ipsi-lateral sides of the thorax. Two RSLs 1200, one on each side of the patient's chest, may also achieve this. The bifurcated design may achieve this result while reducing the number of implanted components and reducing volume of the INS header 1110 since only one RSL port 1112 is required.

The main tubular lead body 1220 of the RSL 1200 may be designed to withstand thoracic movement due to flexion, extension, rotation and breathing. To withstand this environment, the main tubular body 1220 may include a flexible silicone jacket formed such that each distal end has two sigmoid sections, 1230 and 1240, and conductors comprising small diameter ETFE insulated MP35NLT cables (not visible) disposed inside the jacket. An injection molded Y-fitting (yoke) connects the proximal portion of the RSL 1200 to the distal portions, creating the bifurcation section 1280. Conductors, here five, may be continuously fed from the connector assembly through the proximal tubing body 1220 and proximal portion of the Y-fitting. Three of these conductors may continue through the ipsi-lateral distal portion of the Y-fitting to the ipsi-lateral distal tubing body of the RSL. The other two conductors may continue through the contra-lateral distal portion of the Y-fitting to the contra-lateral distal tubing body of the RSL. The tubing bodies may be adhesively bonded or molded to the Y-fitting. The number of conductors may equal the number of contacts in the INS header 1112, here five. Two of the conductors, one on each side, may connect proximally to current emitting header contacts, (e.g., R1 and L1), and terminate distally in current emitting electrodes 1250. Three of the conductors may connect proximally to voltage sensing header contacts (e.g., R2, R3, and L3) and terminate distally in voltage sensing electrodes. As mentioned previously, dual-function electrodes may enable any electrode (ring electrode 1250 or 1260) to emit current or sense voltage. This switching may occur via components on the INS circuit board 1130. Alternatively, a bridge may be formed joining two contacts in the proximal connector assembly such that the corresponding electrode may function as either a current emitting electrode 1250 or voltage sensing electrode 1260. Dual-function electrodes may enable more vectors in an implanted region without additional electrodes.

The proximal sigmoid section 1230 may isolate movement of the INS 1100 from the electrodes 1250 and 1260, and accommodates anatomic variations in thoracic length. The distal sigmoid section 1240 may allow adjustment in the distance between electrodes 1250 and 1260, and reduce strain applied between the anchor tabs 1270, which may be secured with sutures to the underlying fascia when implanted. The proximal sigmoid 1230 section may have 5 wavelengths with an outside peak-to-peak dimension of approximately 0.84 inches (2.1 cm) and an overall length of 7.0 inches (17.8 cm). The distal sigmoid 1240 section may have half a wavelength with a center-to-center peak-to-peak dimension of approximately 0.43 inches (2.1 cm) and an overall length of 0.869 inches (2.2 cm).

The two distal portions' electrodes 1250 and 1260 may comprise five electrodes total, and each may comprise MP35N rings having an exposed surface area. The distal electrode containing a suture hole 1290 may have an exposed surface area of 73.8 mm$^2$ including the suture hole 1290, and 66.4 mm$^2$ not including the suture hole 1290. The proximal electrode containing an anchor tab 1270 may have an exposed surface area of 30.5 mm$^2$ and the electrode without an anchor tab may have an exposed surface area of 32.0 mm$^2$. Tubular strain relief segments may be disposed on the lead body on either side of electrode 1250 or 1260. Where the strain relief segments are adjacent to each other, a gap may be provided there between the strain relief segments or the segments may abut one another to avoid a stress concentration point. Strain reliefs may also be disposed on each end of the electrodes 1250 or 1260 to avoid stress concentration points. The anchor tab 1270 may be disposed over an electrode leaving the proximal and distal extremities of the electrode exposed.

At any given time, the INS 1100 may detect impedance along a vector, with each end of the vector defined by a current delivery electrode 1250 and a voltage sensing electrode 1260. In each vector, a small excitation current may be delivered between the two current emitting electrodes 1250, and the corresponding change in voltage may be measured by the two voltage sensing electrodes 1260. The INS housing 1120 may also act as a current emitting and/or voltage sensing electrode, or contain smaller current emitting and/or voltage sensing electrodes on its surface. Changes in impedance may be calculated by dividing the change in voltage by the excitation current, which correspond to movement of the diaphragm, lung, and other tissues to produce a signal indicative of respiratory activity.

The proximal connector assembly 1210 of the RSL 1200 may be designed to provide a reliable mechanical and electrical connection of the RSL 1200 to the INS 1100. It has a number of strain relief elements that may enable it to withstand handling during insertion and removal from the INS 1100, as well as adverse conditions encountered when implanted. The connector assembly 1210 may include five in-line stainless steel ring contacts (one for each conductor) and five silicone ring seals. Set screws in the header of the INS 1100 may bear down on the contacts, and, together with ring seals, provide a sealed mechanical and electrical connection to the INS 1100. Ring seals may be part of the RSL 1200 or the INS header 1110. With the exception of the distal electrodes, all external surfaces of the RSL 1200 exposed to the body when implanted may comprise implantable grade polymers selected from the following: silicone, and fully cured silicone adhesive. The distal electrodes may comprise implantable grade MP35N and may be sealed to the lead body with silicone adhesive, for example.

A wide variety of respiration sensing lead designs may be employed to provide at least one bio-impedance vector (current injection electrode pair and voltage sensing electrode pair) from a point along the costal margin to a point along the opposite (trans-lateral) costal margin, to a point along the same side (ipsi-lateral) costal margin, or to a point in the infraclavicular region, as seen in FIG. 4C. For example, an alternative embodiment of the RSL 1200 is shown in FIG. 4B, wherein the bifurcation section 1280 and contra-lateral distal portion are eliminated. In this three electrode straight RSL 1200 embodiment, there is one current emitting ring electrode 1250 and two voltage sensing ring electrodes 1260. The lead body may contain three conductors. The connector assembly 1210 may include three in-line stainless steel ring contacts (one for each conductor) and three silicone ring seals. The RSL may have an overall length of 21.2 inches (53.9 cm). The distance from the proximal tip of the proximal connector assembly 1210 to the first sigmoid may be 9.5 inches (24.1 cm). The proximal sigmoid 1230 section may have 5 wavelengths with an outside peak-to-peak dimension of approximately 0.84 inches (2.1 cm) and an overall length of 7.0 inches (17.8 cm). The distal sigmoid 1240 section may have a ½ wavelength with a center-to-center peak-to-peak dimension of approximately 0.43 inches (2.1 cm) and a length of 0.869 inches (2.2 cm). The RSL 1200 may be implanted ipsi-laterally on the ipsi-lateral costal margin, a less invasive surgery, while maintaining vectors from the ipsi-lateral costal margin to the infraclavicular region, see FIG. 4D.

Further alternative embodiments are illustrated in FIGS. 4E, 4F, 4G, and 4H, wherein the RSL 1200 may contain four electrodes, one or more of which can function as either a current emitting electrode 1250 or voltage sensing electrode 1260, as described previously. Here, this may be achieved by exposing the conductor of the bi-functional electrode to two contacts (one voltage sensing, one current emitting) in the INS header 1110, and selecting only one contact for sensing. Alternatively, this functionality may be built into the INS circuit board 1130. These embodiments of the RSL 1200 may be implanted ipsi-laterally (e.g. on the right costal margin), which is a less invasive surgery, while maintaining vectors from the ipsi-lateral costal margin to the infraclavicular region.

Figure 4A:
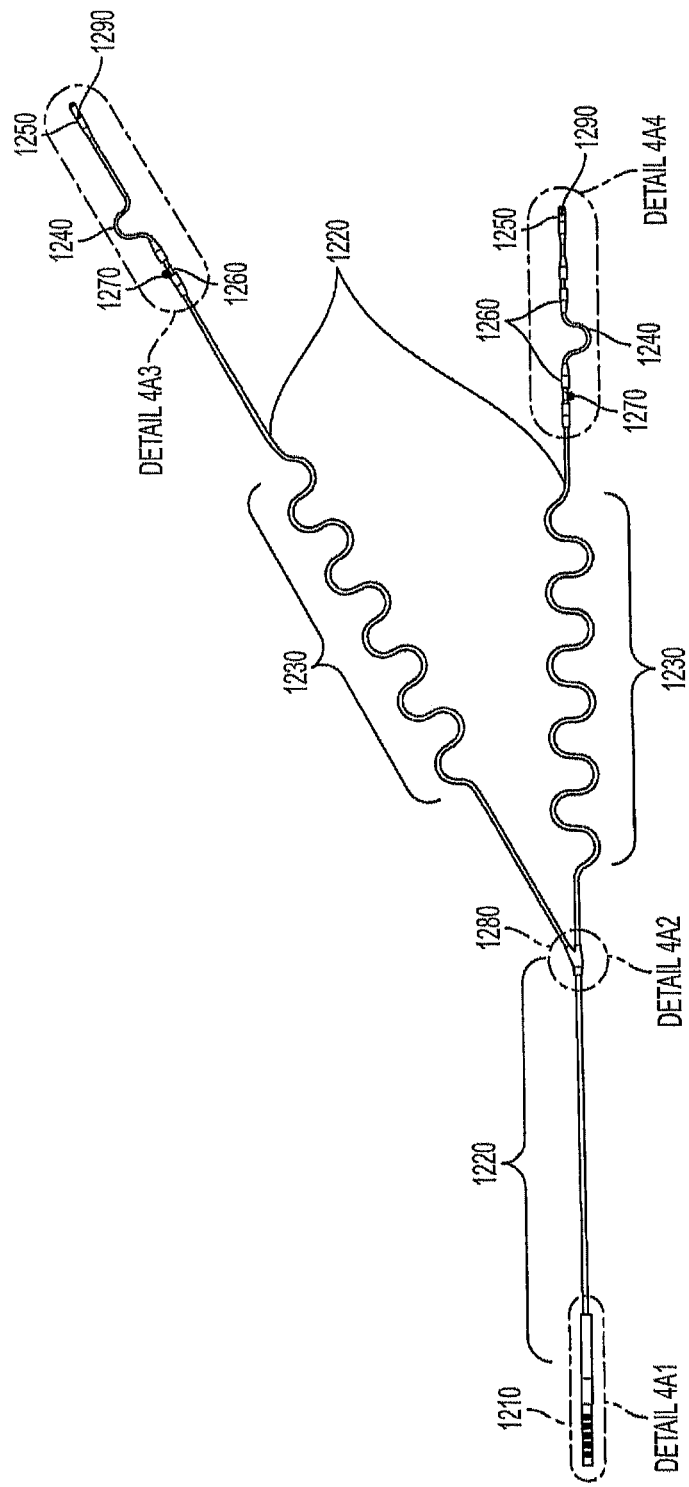
FIG. 4A is a perspective view of a bifurcated respiration sensing lead which may be used in the system shown in FIG. 1.
Figure 4E:
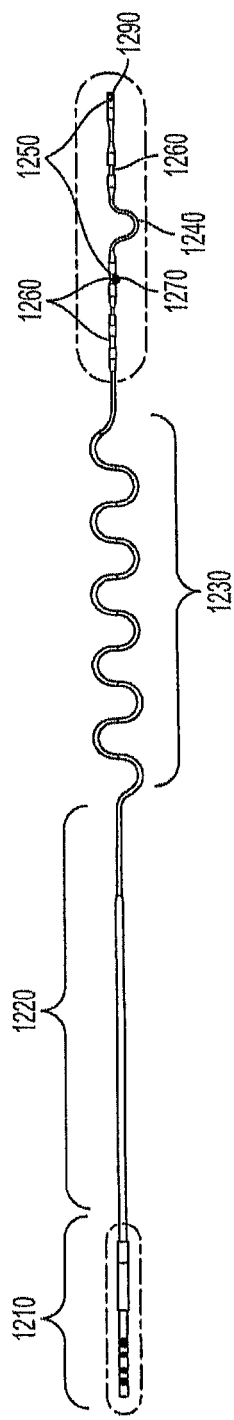
FIG. 4E illustrates an alternative embodiment of the respiration sensing lead which may be used in the system shown in FIG. 1.

FIG. 4E illustrates a straight four electrode RSL 1200. This is similar in design to the RSL 1200 of FIG. 4B, wherein there may be a first, second, third, and fourth electrodes, from proximal to distal.

Figure 4F:
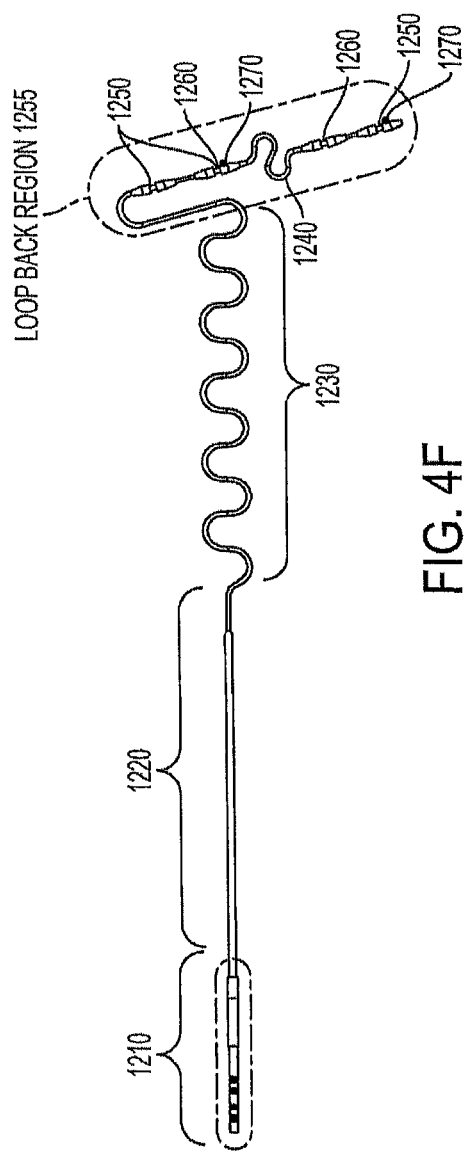
FIG. 4F illustrates an alternative embodiment of the respiration sensing lead containing a loop-back region. This lead may be used in the system shown in FIG. 1.

FIG. 4F illustrates a four electrode RSL 1200 with a loop back region 1255. This differs from the above embodiments in that there may be an extra half sigmoid in the proximal sigmoid section 1230 after which the lead body may enter the loop back region 1255. Here, the lead body may run in the medial direction, then loop back in the lateral direction. The loop back region 1255 may act as a strain relief and allow the medial anchor tab 1270 to be sutured at the intersection of the two tunneling paths (from INS incision to medial incision, and between two RSL incisions). This may allow the RSL 1200 to lie in an unbiased exemplary configuration along the costal margin. Here again, the first and third most distal electrodes may be current emitting, and the second, third, and fourth most distal electrodes may be voltage sensing.

Figure 4G:
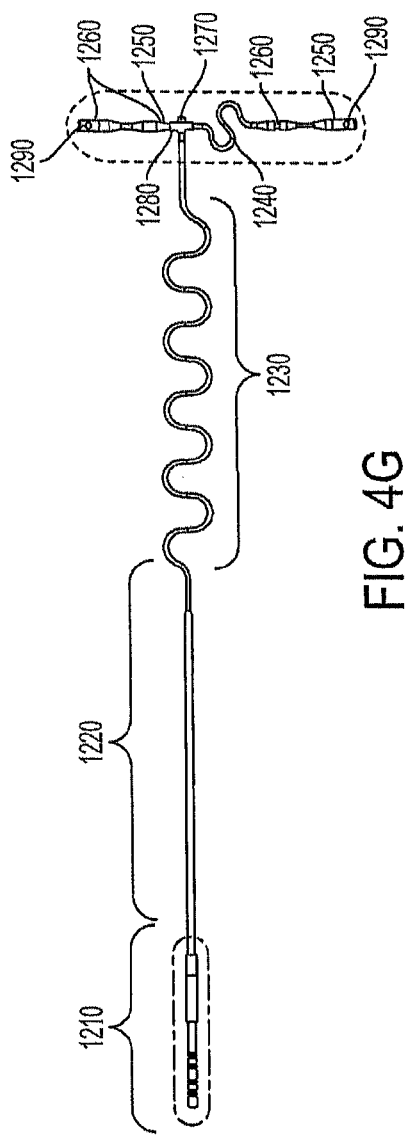
FIG. 4G illustrates an alternative embodiment of the respiration sensing lead which may be used in the system shown in FIG. 1.

FIG. 4G illustrates a four electrode RSL 1200 with a bifurcation section 1280 created by a T-fitting. An injection molded T-fitting may connect the proximal portion of the RSL 1200 to the distal portions, creating the bifurcation section 1280. Conductors, here four, may be continuously fed from the connector assembly through the proximal tubing body 1220 and proximal portion of T-fitting. Two of these conductors may continue through the proximal distal portion of the T-fitting to the proximal distal tubing body of the RSL. The other two conductors may continue through the medial distal portion of the T-fitting and to the medial distal tubing body of the RSL. The tubing bodies may be adhesively bonded or molded to the T-fitting. The anchor tab 1270 may be adhesively bonded to the bifurcation section 1280. Again, this may allow the RSL 1200 to lie in an unbiased exemplary configuration along the costal margin. In addition, the T-fitting may act as a strain relief. Both medial and lateral distal electrodes may contain suture holes 1290.

Figure 4H:
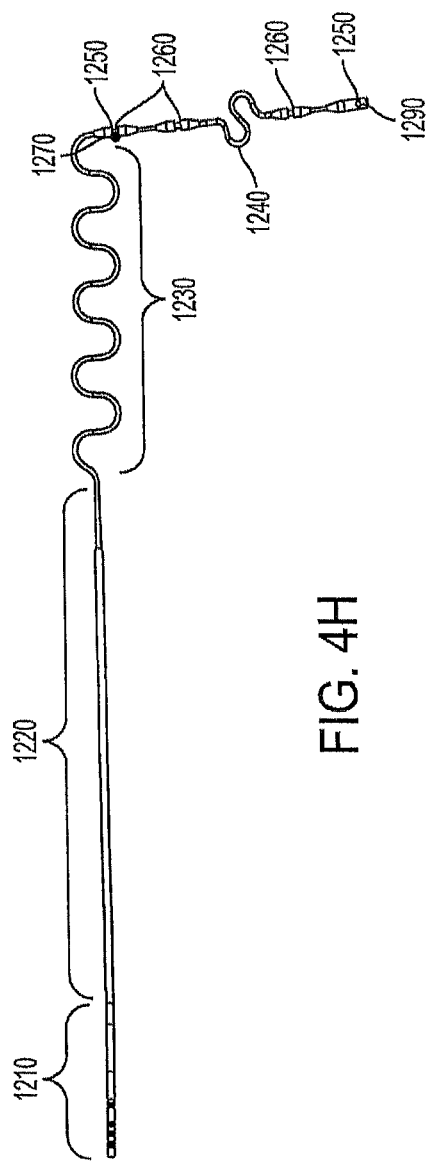
FIG. 4H illustrates an alternative embodiment of the respiration sensing lead which may be used in the system shown in FIG. 1.

FIG. 4H illustrates an alternative embodiment of the RSL 1200, wherein the RSL 1200 may have an overall L-shape. In this embodiment, there may be four ring electrodes, numbered one through four from most proximal to furthest distal. The first and fourth electrodes may be current emitting electrodes 1250. The second and third electrodes may be voltage sensing electrodes 1260. The lead body may contain four conductors. The connector assembly 1210 may include four in-line stainless steel ring contacts (one for each conductor) and four silicone ring seals. The proximal portion of the RSL 1200 (including the proximal connector and proximal sigmoid) may have an overall length of 17.0 inches (43.2 cm). The distance from the proximal tip of the proximal connector assembly 1210 to the first sigmoid may be 11.1 inches (28.1 cm). The proximal sigmoid 1230 section may have 4.5 wavelengths, each wavelength 1.25 inches (3.2 cm), and with an outside peak-to-peak dimension of approximately 0.84 inches (2.1 cm). The distal portion of the RSL 1200 (from the distal end of the proximal sigmoid 1230 to the distal suture hole 1290) may have an overall length of 4.9 inches (12.5 cm). The length from the distal end of the proximal sigmoid 1230 to the proximal end of the distal sigmoid 1240 may be 2.2 inches (5.7 cm). The length from the distal end of the distal sigmoid 1240 to the distal suture hole 1290 may be 1.8 inches (4.6 cm). The distal sigmoid 1240 section may have a center-to-center peak-to-peak dimension of approximately 0.92 inches (2.3 cm). The RSL 1200 may be implanted ipsi-laterally on the ipsi-lateral costal margin, a less invasive surgery, while maintaining vectors from the ipsi-lateral costal margin to the infraclavicular region.

Implantable Neurostimulator (INS)

Figure 5A:
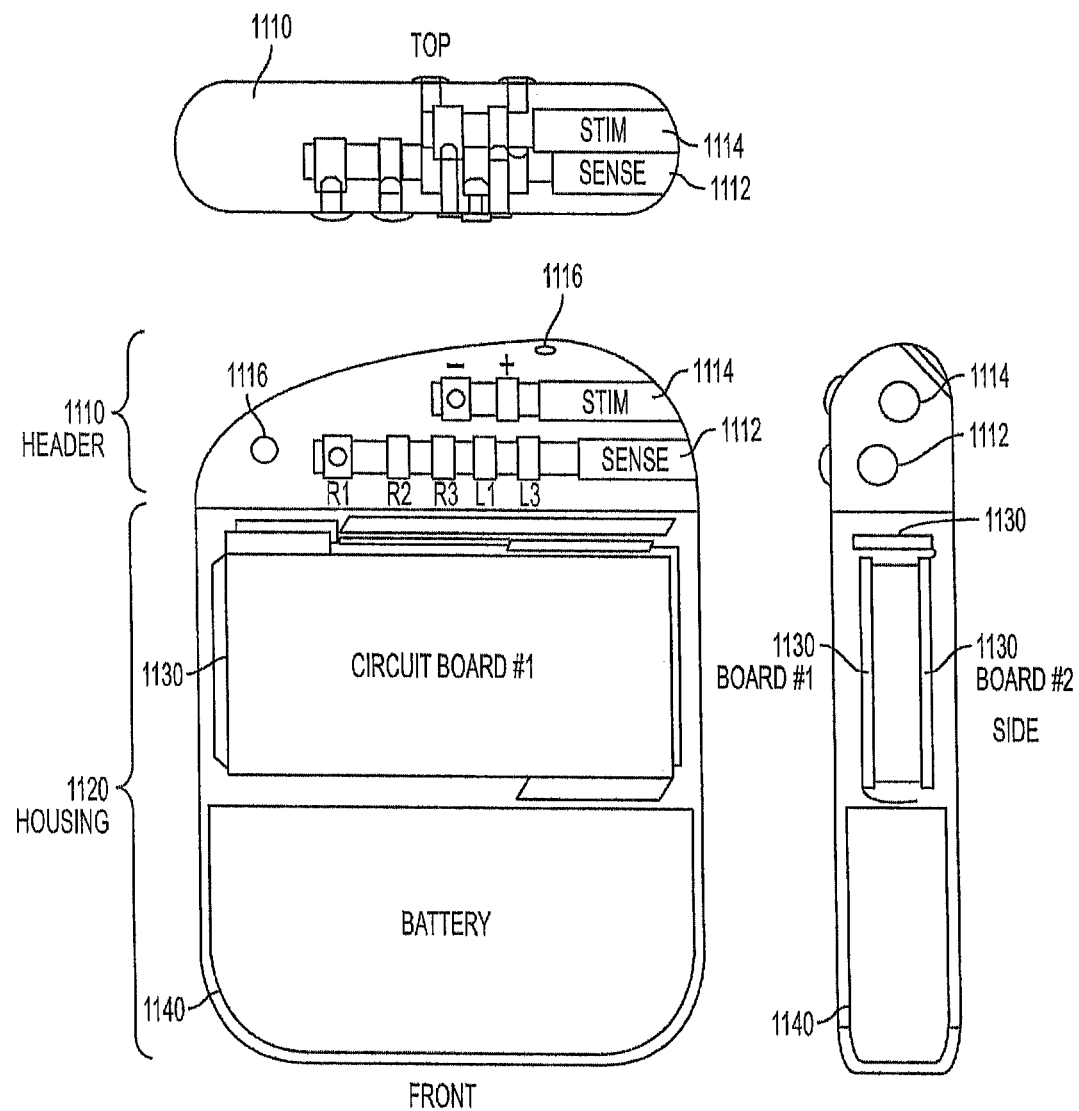
FIG. 5A shows front, side and top views of an implantable neurostimulator for use in the system shown in FIG. 1.

FIG. 5A schematically illustrates the INS 1100 in more detail, including a front view, a top view, and a side view. The INS 1100 may be similar in certain aspects to commercially available implantable pulse generators and implantable neurostimulators, which may be obtained from suitable manufacturers such as CCC Medical Devices (Montevideo, Uruguay), for example. Other non-limiting examples of equipment which may be used include commercially available at-home sleep study or monitoring equipment, pulse oximeters, and/or CPAP/BiPAP machines with an oximeter. The INS 1100 generally may include a header 1110 for connection of the STL 1300 and RSLs 1200, and a hermetically sealed housing 1120 for containing the associated electronics 1130, a battery 1140 (e.g., Greatbatch 9086), and an accelerometer 1150. The INS 1100 may contain an oxygen sensor (e.g., $SaO_2$, $SpO_2$, ion, etc.). Alternatively, the oxygen sensor may be incorporated in a lead with connection to the INS 1100. Also alternatively, the oxygen sensor may be provided as a separate stand-alone device, or as a component of another device, that generates values that can be provided to the INS 1100 or provided to a processor or caregiver receiving information from a patient during a sleep study, while receiving therapy, or while being evaluated for the receipt of therapy.

The electronic circuitry 1130 contained in the INS 1100 may enable telemetry communication with the programmer system 2100 and therapy controller 2500, detection of respiration via the RSL 1200, determination of the start time and duration of a stimulation signal, and delivery of a controlled electrical stimulation signal (pulse train) via the STL 1300. The INS 1100 also may record therapy history data (device settings, status, measured data, device use, respiration data, stimulation delivery data, statistics based on measured signals, etc., for example).

The header 1110 may comprise epoxy that is hermetically sealed to the housing 1120. The housing 1120 may comprise titanium. As mentioned in the context of respiration sensing, the housing 1120 may be used as an electrode for bio-impedance respiration measurement. Similarly, electrodes 1360 may be used as an electrode for bio-impedance respiration measurement. For example, the housing 1120 may comprise a combination current emitting and voltage sensing electrode for respiration detection. Alternatively, separate electrodes may be included in the header of the device from which to sense or stimulate.

The header 1110 may include two ports: one RSL port 1112 (labeled "sense") for receiving the proximal connector of the RSL 1200 and one STL port 1114 (labeled "stim") for receiving the proximal connector of the STL 1300. The port configured to receive a STL 1300 may include two set screws (labeled "−" for cathode and "+" for anode) with associated set screw blocks and seals for mechanical and electrical connection to corresponding contacts on the proximal connector 1310 of the STL 1300. Similarly, the port that is configured to receive a RSL 1200 may include five set screws (two labeled R1 and L1 for current emitting electrodes and three labeled R2, R3, and L3, for voltage sensing electrodes) with associated set screw blocks and seals for mechanical and electrical connection to corresponding contacts on the proximal connector 1210 of the RSL 1200. Seals may be located between electrical contacts as well as between the distal-most electrical contact and the remainder of the proximal connector assembly 1210. These seals may electrically isolate each contact.

Alternatively, wound coil spring contacts may provide electrical connections between the INS header 1110 and the proximal connector assemblies 1210 and 1310. Typically, one electrical connection may still be achieved with a set screw which may also serve to hold the connector assembly in place. This embodiment may provide a sealed mechanical and electrical connection of the RSL 1200 and STL 1300 to the INS 1100. An example of this technology is Bal Seal's Canted Coil™ Spring Technology.

The header 1110 further may include two suture holes 1116 for securing the INS 1100 to subcutaneous tissue such as muscle fascia using sutures when implanted in a subcutaneous pocket. As shown, component values and component configurations are given by way of example, not limitation.

The INS 1100 may generate the stimulation output for delivery to the hypoglossal nerve by way of the STL 1300. For this purpose, the INS 1100 may have a bipolar stimulation output channel corresponding to the STL port 1114, with the channel providing a pulse train of bi-phasic constant current pulses with a frequency range of 20 to 50 Hz, a pulse width range of 30 to 215 µs, an amplitude range of 0.4 to 5.0 mA, and a stimulation duty cycle range of 41%-69%, by way of example, not limitation.

The INS 1100 also may generate the excitation signal and measures voltage by way of the RSL 1200 for bio-impedance respiration detection. For this purpose, the INS 1100 also may have two respiration sensing channels for simultaneous acquisition of bio-impedance sensing on different vectors. This may be achieved by sequential or alternating sampling of different vectors. The INS 1100 may measure bio-impedance via the RSL port 1112, with each channel providing a small excitation current ("I") and measuring voltage ("V"). The excitation signal may comprise a 10 Hz biphasic constant current pulse, with the positive and negative phases of each biphasic pulse having amplitude of 450 µA, duration of 80 µs, and charge of 36nC. Current ("I") may be fixed, allowing voltage ("V") to be a relative measure of impedance ("Z"), which corresponds to movement of the diaphragm, lung, and other structures to produce a signal indicative of respiratory activity.

Figure 5B:
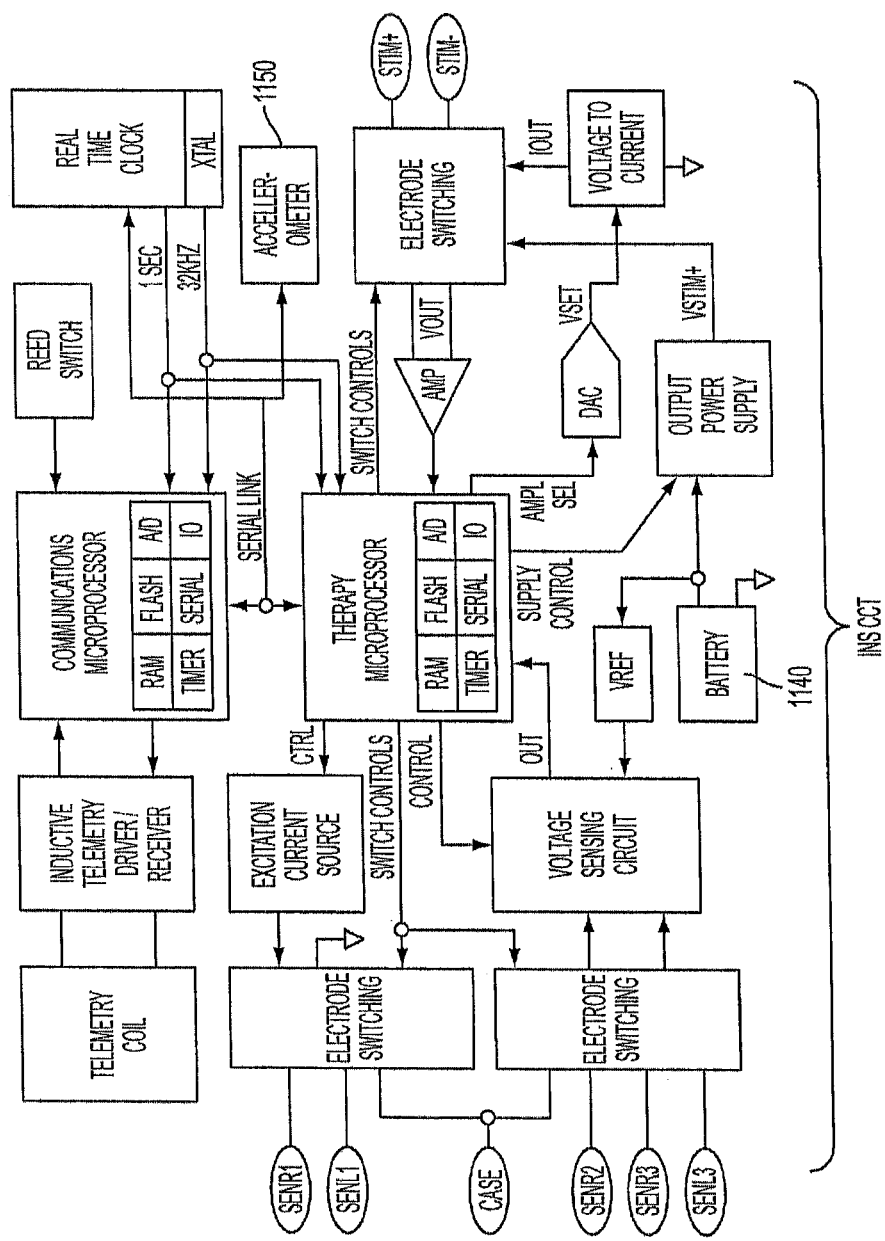
FIG. 5B is a schematic block diagram of electronic circuitry for use in the implantable neurostimulator shown in FIG. 5A.

With reference to FIG. 5B, a block diagram of an example of the INS circuit 1130 is shown schematically. The INS circuit 1130 may utilize a microprocessor to control telemetry communications with the programmer system 2100, operating the sensing circuits to monitor respiration via the RSL 1200, controlling the delivery of output stimuli via the STL 1300, monitoring the accelerometer, magnetically sensitive reed switch and the real-time clock. The microprocessor may contain built-in support circuits (RAM, flash memory, analog to digital (A/D) converter, timers, serial ports and digital IO) used to interface with the rest of the INS circuit 1130, including the accelerometer 1150. Two microprocessors communicating via a serial link may be used instead of one microprocessor, with the first microprocessor for telemetry communications, monitoring the accelerometer, magnetically sensitive reed switch and the real-time clock; and the second microprocessor for operating the sensing circuits and controlling the delivery of output stimuli. Alternatively, a single microprocessor could perform these functions.

The telemetry interface circuits may consist of a tuned telemetry coil circuit and a telemetry driver/receiver circuit to allow pulse encoded communication between the external programmer system 2100 and the microprocessor. As an alternative to telemetry coils and an inductive link, RF antennae with associated circuitry may be used to establish a RF link to provide for arms-length telemetry. The reed switch may provide a means for the INS 1100 to be controlled by using a magnet placed in close proximity thereto. The real-time clock may provide the basic time base (768 Hz) for the INS circuit 1130 as well as a clock (year, day, hour, minute, second) which can be used to control the scheduled delivery of therapy. The clock may also be used to time-stamp information about the operation of the system that is recorded on a nightly basis.

The respiratory sensing circuit may be comprised of two main parts: the excitation current source (output) and the voltage sensing circuit (input). As will be described in more detail hereinafter, respiration may be detected via the RSL 1200 using a 3 or 4-wire impedance measurement circuit. In a 4-wire measurement, an excitation current may be driven through a pair of electrodes, and the resulting voltage may be measured on a separate pair of electrodes. The electrode switching circuits may allow the INS 1100 to monitor one of several different vectors from the RSL electrodes 1250 and 1260. As mentioned previously, each physical electrode may function as a current emitting electrode 1250 or a voltage sensing electrode 1260, depending on the programmable vector configuration. In one embodiment of a 3-wire measurement, the INS housing 1120 may be used as both an excitation and sensing electrode. The excitation current circuit may deliver biphasic pulses of low level (450 uA) current to the selected electrode pair every 100 ms during sensing. The voltage sensing amplifier circuit may synchronously monitor the voltage produced by the excitation current on the selected electrode pair. The resulting output signal may be proportional to the respiratory impedance (0.07 □ to 10 □) and may be applied to the A/D circuit in the microprocessor for digitization and analysis.

The stimulation output circuits may deliver bursts of biphasic stimulation pulses to the STL 1300. These bursts may be synchronized to the sensed respiratory waveform to deliver stimulation and thus airway opening at the appropriate time. The stimulation output circuits may include an electrode switching network, a current source circuit, and an output power supply. The electrode switching network also may allow for a charge balancing cycle following each stimulation pulse during which the outputs may be connected together with no applied output pulse. The timing and polarity of the pulse delivery may be provided by control outputs of the microprocessor. The microprocessor may select the amplitude (e.g., 0.4 mA to 5 mA) of the output current from the current source circuit which may be applied through the switching network. The output power supply may convert battery voltage to a higher voltage (e.g., 5V to 14V) which may be sufficient to provide the selected current into the load impedance of the STL 1300. The microprocessor may measure the voltage output from the electrode switching network resulting from the delivered current and the load impedance. The microprocessor may divide the output voltage by the output current resulting in a measure of the load impedance (400 □ to 2700 □) which can be an indicator of integrity of the STL 1300.

The INS 1100 (or lead connected to the INS 1100) may contain, communicate with, or be used with an oxygen sensor configured to monitor oxygen levels, for example during a therapy session. This may be used to monitor efficacy as well to set stimulation settings during a therapy session. For example, the INS 1100 may be programmed to increase stimulation when oxygen de-saturations are detected at a programmable threshold rate and/or severity. In addition, the INS 1100 may turn stimulation on once de-saturations are detected, wherein thresholds of rate and severity are programmable. Desaturations may act to indicate the sleep state or wakefulness. In a similar manner, electroneurogram (ENG) may be used to monitor nerve activity, which may also be indicative of sleep state and/or wakefulness. The INS 1100 may use the indication of sleep state or wakefulness to change stimulation settings. For example, stimulation may be increased when the patient is in N3 or REM sleep. In addition, stimulation level may be decreased or turned off during stage N1, N2, or wakefulness.

The INS 1100 circuitry may contain a three-axis accelerometer 1150 that can be used to determine the patient's body position (supine, prone, upright, left, or right side) and/or detect motion events (wakefulness). These data may be used to change stimulation settings or inhibit output. The INS 1100 may be programmed to increase stimulation intensity when the patient is in specific body positions (e.g., supine, a more challenging position). The INS 1100 may segregate recorded therapy statistics (e.g., cycling detector events, oxygen desaturations) with respect to body position. For example, a patient's cycling detector may record very few events in the lateral position and many events in the supine position, indicative of the patient being treated in the lateral position.

Figure 6A:
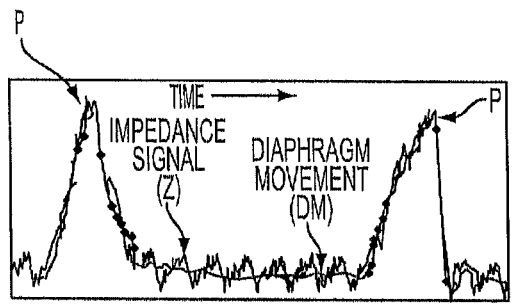
FIGS. 6A, 6B, and 6C illustrate a respiratory waveform as detected by a bio-impedance signal, and further illustrate physiological events corresponding to the waveform and exemplary stimulation delivery algorithms for use in the system shown in FIG. 1.

With reference to FIG. 6A, the bio-impedance respiration signal ("Z"), which is generated by dividing the change in measured voltage ("V") by the excitation current ("I"), tracks with diaphragm movement (DM) over time and therefore is a good measure of respiratory activity, and may be used to measure respiratory effort, respiratory rate, respiratory (tidal) volume, minute volume, etc. If the excitation current (I) is constant or assumed constant, then the bio-impedance (Z) is proportional to the measured voltage (V), and thus the voltage (V) may be used as a surrogate for bio-impedance (Z), thereby eliminating the division step. As used in this context, diaphragm movement includes movements and shape changes of the diaphragm and adjacent tissue that occur during normal breathing and during obstructed breathing. The bio-impedance waveform may be filtered to reduce noise and eliminate cardiac artifact, clarifying positive and negative peak occurrence. The signal may be filtered using a first order low pass filter. Alternatively, a higher order curve fit approach could be utilized to filter the signal. The (positive or negative) peak (P) of the impedance signal (Z) corresponds to the end of the inspiratory phase and the beginning of the expiratory phase. If the signal is normal (as shown), the positive peak is used; and if the signal is inverted, the negative peak is used. The beginning of the inspiratory phase occurs somewhere between the peaks and may not be readily discernable. Thus, the impedance signal provides a reliable fiducial (P) for end-inspiration and begin-expiration (also called expiratory onset), but may not provide a readily discernable fiducial for begin-inspiration (also called inspiratory onset). Therefore, algorithms described herein do not rely on begin-inspiration (or inspiratory onset) to determine the start of stimulation bursts as proposed in the prior art, but rather use a more readily discernible fiducial (P) corresponding to begin-expiration (or expiratory onset) in a predictive algorithm as described below. Other non-predictive (e.g., triggered) algorithms are described elsewhere herein.

Gross body motion may be indicative of patient wakefulness and may change the bio-impedance signal (Z). A motion event may be detected, for example, by assessing variability in the bio-impedance peak-to-peak signal strength (P-P). Different thresholds of sensitivity may be utilized such that minor movements are not grouped with motion events. When a motion event is determined, stimulation may be turned off or turned down until motion stops or for a programmable duration of time. The frequency and duration of these motion events may be recorded in device history. The accelerometer 1150 could be utilized in a similar fashion to detect and record motion events.

Waxing and waning of the bio-impedance signal (Z) may be indicative of apneas or hypopneas. Generally referred to as cycling, this pattern may be detected, for example, by assessing trends of increasing and decreasing average P-P amplitude values. Different thresholds of sensitivity may be utilized such that minor changes in P-P values are not declared cycling events. When cycling is detected, stimulation parameters may be initiated or changed (e.g., increased intensity, increased duty cycle, etc.) to improve therapy. The frequency and duration of these cyclic breathing patterns may be recorded in therapy history. These values may be used as an indicator of how well the patient is being treated, providing an estimate of AHI.

The INS 1100 may be programmed to change stimulation level between therapy sessions, days, or other programmable value. The stimulation level may be recorded alongside therapy session data, for example cycling rate (via the cycling detector), oxygen desaturation frequency and severity, stimulation time, variations in respiratory rate, variations in respiratory prediction, etc.

In people without OSA, inspiration is typically 25-50% of the respiratory cycle, with variations in respiration rate being common. Variations may cause actual inspiration to differ from predicted inspiration. The hypoglossal nerve usually activates approximately 300 ms before inspiration and remains active for the entire inspiratory phase. To mimic this natural physiology, stimulation may be delivered to the hypoglossal nerve during the inspiratory phase plus a brief pre-inspiratory period of about 300 ms. To maximize stimulation coverage of actual inspiration and to account for this variability, stimulation may be centered on the predicted inspiration. As mentioned previously, there are reliable fiducials for the beginning of the expiratory phase (peak P) which may be used to deliver stimulation to cover the inspiratory phase plus brief pre and/or post-inspiratory periods.

Accordingly, an algorithm may be used to predict respiratory period and determine the start of the stimulation burst. The predictive algorithm may be contained in software and executed by a microprocessor resident in the INS circuitry 1130, thus enabling the INS 1100 to generate stimulation synchronous with inspiration. One example of a prediction algorithm uses the respiratory period of previous breaths to predict the respiratory period of each subsequent breath. In this algorithm, a respiratory period is determined by calculating the time between peaks in the bio-impedance signal (Z). If the actual respiratory period is different from the predicted respiratory period, then the subsequent predicted respiratory period is resynchronized and updated to equal the actual period, up to a programmable value (e.g., 300 ms). If the difference in respiratory period exceeds the programmable value, then the predicted respiratory period is incremented or decremented by this value.

Figure 6B:
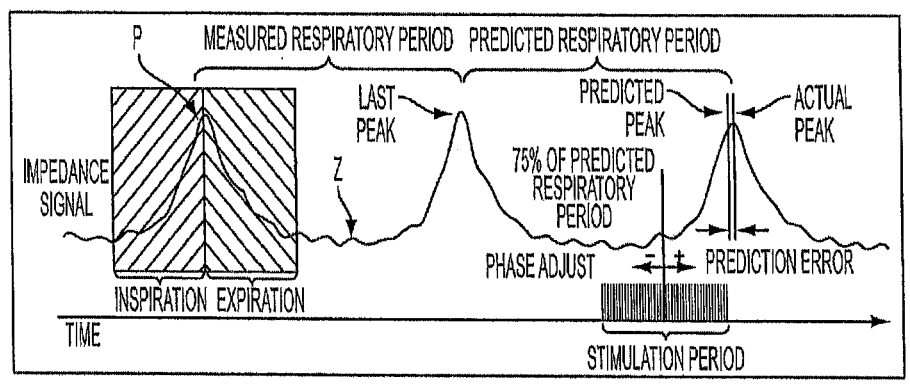

One example of a predictive algorithm is illustrated in FIG. 6B. In this example, the stimulation period is centered about a percentage (e.g., 75%) of the predictive respiratory period. The predictive algorithm uses historical peak data (i.e., begin-expiration data) to predict the time to the next peak, which is equivalent to the predicted respiratory period. The stimulation period is centered at 75%, for example, of the predicted respiratory time period. Thus, the time to start a stimulation burst is calculated by predicting the time to the next peak, adding 75% of that predicted time to the last peak, and subtracting ½ of the stimulation period (stimulation start time=time of last peak+75% of predicted time to next peak−½ stimulation period). A phase adjustment parameter (range: +/−1000 ms, for example) permits the stimulation period to be biased early or late.

Figure 6C:
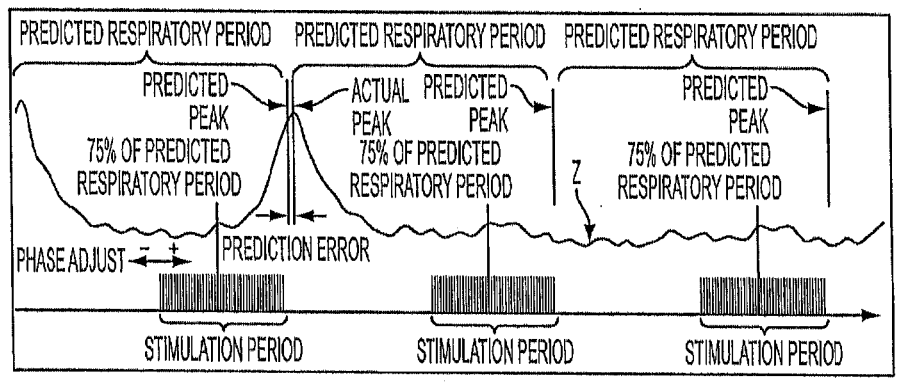

A feature common to the predictive algorithms is illustrated in FIG. 6C. This feature provides a sequence of predicted respiratory periods in case the respiration impedance signal ("Z") is temporarily lost (e.g., due to change in respiratory effort). Until a subsequent respiratory peak is detected, stimulation parameters which are based on the measured respiratory period (e.g., stimulation period) are unchanged. Thus, stimulation timing remains synchronous to the last detected peak.

The stimulation duty cycle may vary to meet efficacy and safety requirements. Generally, the stimulation duty cycle may be used to determine the stimulation period as a percentage of the predicted respiratory period (stimulation period=duty cycle×predicted respiratory period). After a stimulation burst (pulse train) is started, stimulation may continue until the end of the stimulation burst as set by the stimulation duty cycle, or until the next actual peak is detected, whichever occurs first. Alternatively, the feature of terminating a stimulation period when an actual peak is detected may be turned off.

The stimulation duty cycle may be fixed or adaptive. In the fixed mode, the stimulation duty cycle may be set using the programmer system 2100 to designate a fixed percentage value. This fixed value may be increased when the respiratory signal is lost, increasing the likelihood of aligning with actual inspiration. In adaptive mode, the duty cycle may be allowed to vary as a function of a characteristic of respiration. For example, the adaptive duty cycle may increase when prediction is less accurate (higher variability in respiration rate) or when the respiratory signal is lost. Thus, in some instances, the stimulation duty cycle may run above normal (e.g., above 50% to 60%) to achieve a better likelihood of covering the inspiratory phase. Because above normal stimulation duty cycle may result in nerve and/or muscle fatigue if prolonged, it may be desirable to offset above-normal stimulation periods with below-normal stimulation periods to result in a net normal duty cycle. Thus, when the prediction is highly accurate (stable respiration rate), the stimulation duty cycle may be reduced.

The following stimulation duty cycle parameters are given by way of example, not limitation. In fixed mode, the maximum stimulation duty cycle may be set from 41% to 69% in 3% increments, and the default setting may be 50%. In adaptive mode, the stimulation duty cycle for a respiratory period may vary from 31% to 69% in 3% increments, and the maximum running average may be set to 53%. As mentioned above, the adaptive mode allows the duty cycle to decrease when respiratory period is stable and increase with respiratory period variability, for example, and the stimulation duty cycle may run in excess of 53% for a limited period of time, but those periods are proportionally offset by periods where the stimulation duty cycle runs less than 53% (e.g., according to an exponentially weighted moving average). For example, an adaptive duty cycle set to 69% would run at that level for no longer than 5 to 7 minutes before being offset by a lower stimulation duty cycle at 47% to result in a running average of 53%. This equation is approximate and may vary slightly depending on the averaging technique used. Other offset methods may be used as an alternative.

The stimulation duty cycle may be nominally 50%. A duty cycle limiter may be enabled such that it prevents the device from exceeding a programmable long term average stimulation duty cycle threshold (e.g., 53%). Long term average duty cycle may be calculated using a first order filter of duty cycle measured over a fixed time period (e.g., 6 seconds), with a programmable filter time constant (e.g., each iterative calculation is given a weight of 1/32). If the long term average duty cycle reaches the programmable threshold, then stimulation duty cycle is decreased to a programmable value, (e.g., 44%) until the long term average drops below the nominal value (here, 50%), at which time the nominal duty cycle is restored. This safety mechanism may prevent nerve and muscle fatigue.

The INS 1100 may deliver stimulation as a train of pulses with constant pulse width and amplitude at a set frequency for a duration limited by duty cycle. This train of pulses may be described as a pulse train envelope and is illustrated in FIG. 6D. The envelope describes a series of biphasic pulses delivered consecutively during a stimulation burst. When the stimulation level of the positive phase of each biphasic pulse is uniform, this level is the level of the stimulation burst. The INS 1100 may also deliver stimulation in pulse train envelopes wherein the pulses are non-uniform (e.g., pulses may have different amplitudes).

The muscle(s) activated by the stimulation may not require the full stimulation intensity for the duration of the stimulation in order to maintain muscle contraction. Accordingly, the INS 1100 may be programmed to deliver a basic retention intensity pulse configuration, defined as a pulse train envelope wherein each pulse's intensity (e.g., amplitude) is less than or equal to the previous pulse's intensity, (e.g., a two second pulse wherein the first 1000 ms is at 2 mA and the subsequent 1000 ms is at 1.7 mA). This pulse configuration is illustrated in FIG. 6E. This allows the muscle to activate to a level and then remain in that position with a less intense stimulation. This may be more comfortable and allow the patient to fall asleep more easily with the stimulation on, be less likely to cause arousal from sleep, and/or reduce the possibility of muscle/nerve fatigue. Alternatively, the pulse level (amplitude) could be decreased gradually during each burst (rather than abruptly) to reach the same final stimulation level.

A more gradual transition at the start of each burst may be more comfortable and be less likely to cause arousal from sleep, and/or reduce the possibility of muscle/nerve fatigue. Accordingly, the INS 1100 may be programmed to deliver a soft start pulse configuration, defined as a pulse train envelope wherein at the start of each burst, each pulse's intensity (e.g., amplitude) is greater than or equal to the previous pulse's intensity, (e.g., a two second pulse wherein the first 100 ms is at 1.85 mA, the second 100 ms is at 1.95 mA, the third 100 ms is at 2.05 mA and the remaining 1700 ms is at 2.1 mA). This pulse configuration is illustrated in FIG. 6G. The pulse train envelope would thus have a stair-like appearance as stimulation increases to the full stimulation plateau.

In another embodiment, a pulse train envelope may employ a soft start to reach full stimulation and subsequently decrease intensity (amplitude) to a retention intensity for the remainder of the stimulation, (e.g., a two second pulse wherein the first 100 ms is at 1.85 mA, the second 100 ms is at 1.95 mA, the third 100 ms is at 2.05 mA, and the next 700 ms is at 2.1 mA, and the remaining 1000 ms is at 1.8 mA). This pulse configuration is illustrated in FIG. 6F. This configuration may provide the benefits of both soft start and retention intensity, wherein the stimulation starts gradually to fully activate the muscle(s), then decreases to a level of less intense stimulation, with the muscle remaining in a contracted position. FIG. 6H shows nested mode, a simplified version of the previously mentioned retention intensity, wherein there is one step up to the full amplitude, and then an equal step down to the retention intensity.

Figure 6I:
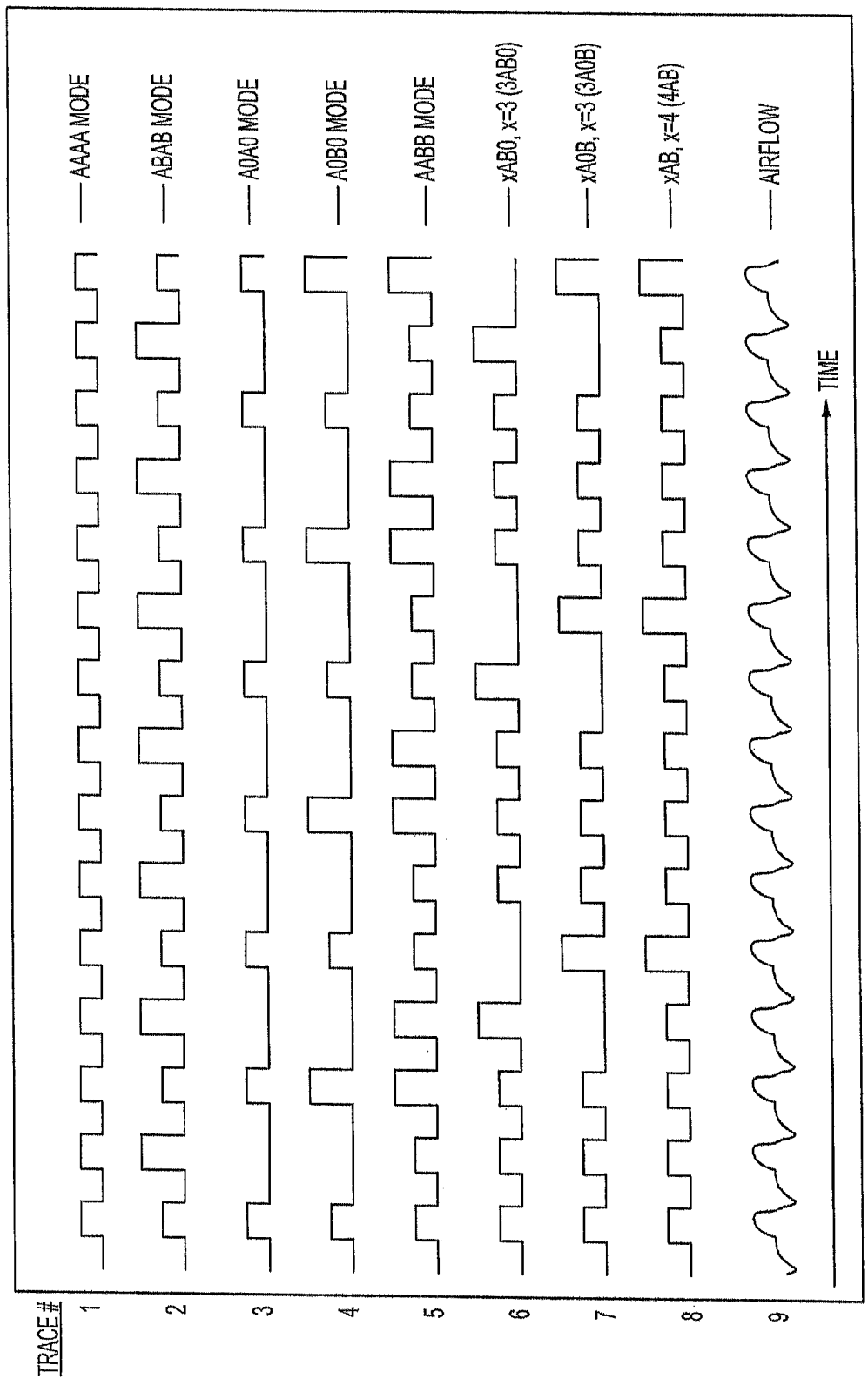
FIG. 6I (traces 1-8) shows various stimulation modes for the implantable neurostimulator shown in FIG. 1, as may be used for therapy or sleep titration, for example.

The INS provides two separate stimulation strengths (A & B) with independent parameters (amplitude, pulse width, frequency, duty cycle, and phase adjust). Stimulation may be delivered in different therapy modes, examples of which are shown in FIG. 6I. FIG. 6I (traces 1-8) illustrates some commonly used modes, all of which are inspiratory synchronous, meaning stimulation is automatically delivered according to an algorithm that predicts the inspiratory phase and initiates stimulation delivery at a desired time relative to inspiration, such as centered on the predicted inspiration. These modes may be used as standard therapy as well as to determine device settings during a polysomnography (PSG) (e.g. sleep titration PSG). Additionally, these modes may be used to diagnose phenotypes of OSA or other diseases.

FIG. 6I (trace 1) illustrates synchronous mode in which every stimulation has the same pulse configuration and amplitude, known as AAAA mode, the default therapy mode. The term AAAA mode means that four consecutive inspirations are covered by stimulation of level A, where A is 2.0 mA, for example. Inspiration is shown in FIG. 6I (trace 9) in the upward direction.

The inspiratory-synchronous ABAB mode, FIG. 6I (trace 2), also delivers stimulation bursts synchronous with inspiration as determined by the device, therapy delivery algorithm settings, and sensed respiratory signal. This mode is similar to AAAA mode, except that the stimulation is delivered on four consecutive inspirations alternating between stimulation levels A and B on each burst where, for example, A is 2.0 mA and B is 1.8 mA.

FIG. 6I (trace 3) illustrates a subset of ABAB mode known as A0A0 mode, wherein the B breath is not stimulated. A may be 2.0 mA and B may be 0 mA, for example.

FIG. 6I (trace 4) illustrates A0B0 mode, wherein a first breath is stimulated at level "A," followed by an second breath that is unstimulated, followed by a third breath that is stimulated at level "B," followed by a fourth breath that is unstimulated, (e.g., A is 2.0 mA and B is 1.8 mA). This allows for simultaneous assessment of two different levels (A and B) when compared to adjacent non-stimulated breaths.

FIG. 6I (trace 5) illustrates AABB mode wherein two breaths are stimulated at level "A" followed by two breaths stimulated at level "B," (e.g. A is 2.0 mA and B is 1.8 mA). In this mode, every stimulated breath is adjacent to a stimulated breath at level "A" and a stimulated breath at level "B." The AABB mode may be used to test if there is a short-term residual cross-over effect when changing from one stimulation level to another stimulation level or from a stimulation level to no stimulation. For example, the airflow measured during the first "A" can be compared to the airflow measured during the second "A" in each sequence over many periods to determine if there is a measurable residual effect from the "B" level simulation.

FIG. 6I (trace 6) illustrates xAB0 mode, wherein "x" number of breaths are stimulated at level "A," followed by a breath stimulated at level "B," followed by an unstimulated breath, (e.g. A is 2.0 mA and B is 1.8 mA). The illustration shows x equals 3 (3AB0), although x may be any number of breaths (e.g., 1, 2, 3, 4, 5, 6, 7, 8, 9).

FIG. 6I (trace 7) illustrates xA0B mode, wherein "x" number of breaths are stimulated at level "A," followed by an unstimulated breath, followed by a breath stimulated at level "B," (e.g. A is 2.0 mA and B is 1.8 mA). The illustration shows x equals 3 (3A0B), although x may be any number of breaths (e.g., 1, 2, 3, 4, 5, 6, 7, 8, 9).

FIG. 6I (trace 8) illustrates xAB mode, wherein "x" number of breaths are stimulated at level "A," followed by a breath stimulated at level "B," (e.g. A is 2.0 mA and B is 1.8 mA). The illustration shows x equals 4 (4AB), although x may be any number of breaths (e.g., 1, 2, 3, 4, 5, 6, 7, 8, 9).

Stimulation may also be delivered in two modes which are not inspiratory synchronous: manual stimulation and asynchronous (fixed) stimulation. Manual mode delivers stimulation at any frequency, pulse width, amplitude, pulse configuration, and/or duration (e.g., up to 12 seconds). In manual mode, stimulation is delivered by manually entering a command via the programmer system to initiate delivery of a stimulation burst or bursts. The stimulation continues until the burst duration expires or stimulation stop is commanded via the programmer system. Manually delivered stimulations may be delivered in any available pulse configuration.

Asynchronous mode (fixed mode) is when stimulation is delivered at regular programmable intervals (e.g., 2.5 seconds of stimulation, followed by 2.5 seconds off). The intervals may be set to a rate similar to a respiratory cycle, (e.g. 5 seconds). Alternatively, longer intervals (e.g. 8 seconds) may decrease the probability of missing two consecutive inspirations, and increase the probability of providing the patient with stimulation during an entire respiratory cycle. This may be used during daytime familiarization, ensuring that the patient receives stimulation in a regular fashion, as breathing patterns during wakefulness may be more irregular and difficult to predict than during sleep. In addition, this mode may be used to test the benefits of asynchronous stimulation compared to inspiratory synchronous stimulation. Asynchronous stimulation may be initiated by programming the device to fixed mode and starting a therapy session. Fixed mode stimulations may be in any available pulse train configuration.

Typically, stimulation is delivered during a therapy session having a start and a stop time. The patient or physician may start a therapy session using the therapy controller 2500 or programmer system 2100. Additionally, a therapy session may begin according to a programmable schedule. During a session, the start of stimulation may be delayed by a programmable delay, subject to patient preference. The patient or physician may stop a therapy session using therapy controller 2500 or programmer system 2100. Additionally, a therapy session may stop according to a programmable schedule or programmable maximum session duration.

A patient or physician may also pause a therapy session for a programmable time using the therapy controller 2500 or programmer system 2100. This pause function may be programmed to turn stimulation off or reduce the stimulation intensity. The pause function may be programmed to smart pause, wherein the stimulation level is automatically reduced after a programmable number of pauses (e.g. after the second pause) in a programmable time period or session. Additionally, the smart pause may increase pause duration after a programmable number of pauses (e.g. the first pause is five minutes, the second pause is ten minutes). These pause functions, including smart pause, may allow a patient to reduce stimulation for brief periods following an arousal from sleep.

At the start of a therapy session or following an interruption in therapy such as a pause, stimulation level may increase incrementally from an initial stimulation level to an initial therapy level during a ramping period. The ramp may occur over a programmable number of stimulations, breaths, or time period. This ramp may also occur after a pause or a motion event. The ramping feature may be more comfortable, allowing the patient to fall asleep more easily with the stimulation on or reduce the likelihood of causing arousal from sleep.

Figure 6J:
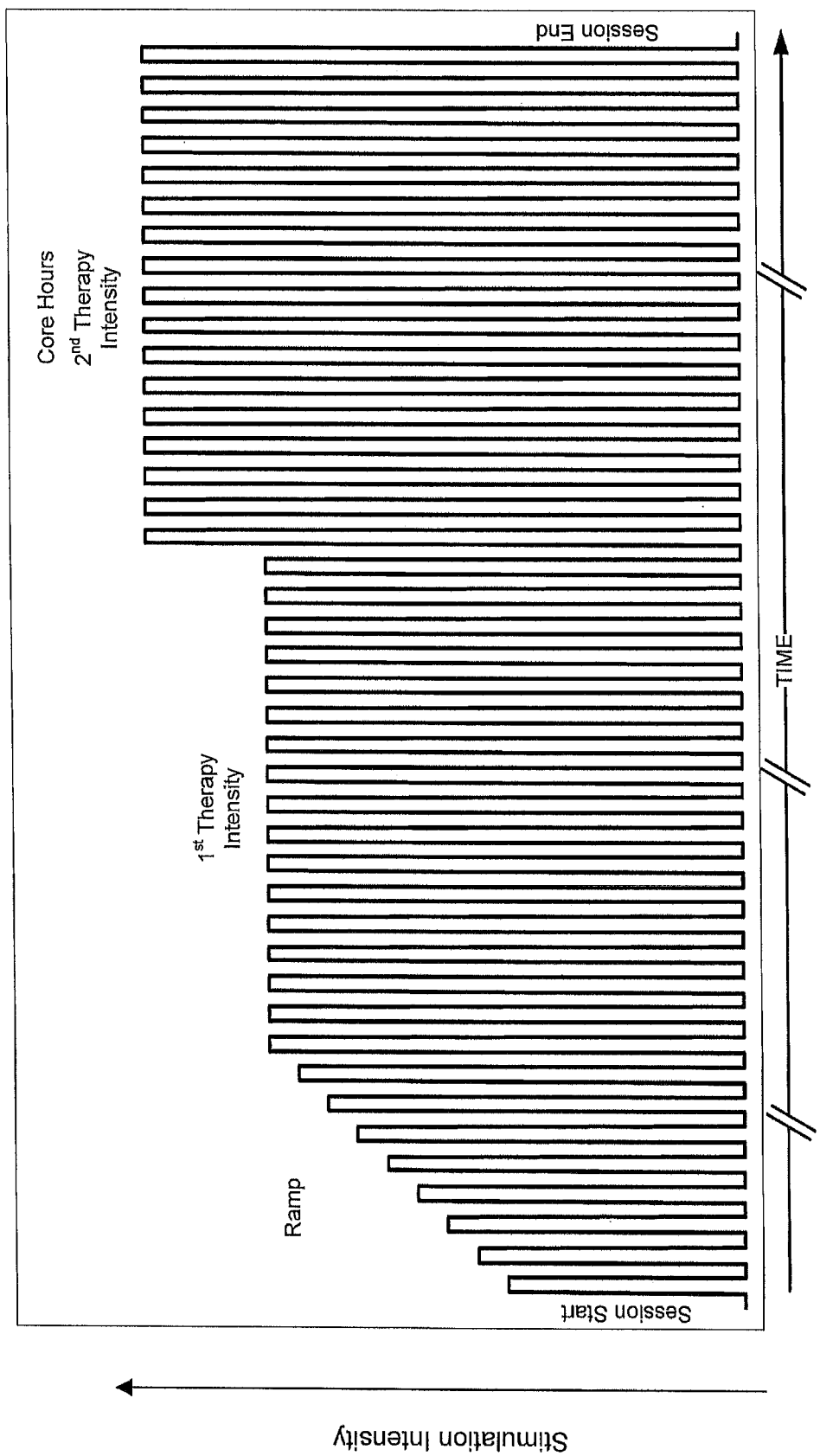
FIG. 6J shows a stimulation regimen called core hours for the implantable neurostimulator shown in FIG. 1, as may be used as a therapy mode.

A patient may be able to tolerate more intense stimulation as a therapy session progresses. This higher intensity stimulation may provide enhanced therapy efficacy. The INS 1100 may be programmed to change stimulation level (e.g., amplitude or pulse width) during a therapy session from an initial level to a second, possibly more efficacious level. This therapy stimulation configuration is illustrated in FIG. 6J and is called core hours. This intensity change may occur after a programmable interval, for example after a fixed duration of time, number of breaths or stimulations (e.g., referring to FIG. 6J, stimulation at a first therapy intensity of 1.8 mA for the first hour of a therapy session, after which stimulation is increased to a second therapy intensity of 2.0 mA until the end of the therapy session). This feature and the related parameters may be programmed by a physician, for example based on patient feedback. This feature may allow a patient to fall asleep at a more tolerable level of stimulation, and then as the therapy session progresses, receive more appropriate therapeutic benefit.

Stimulation may be delivered during a therapy session, which may start and stop according to a programmable schedule or manual use of the therapy controller 2500. The therapy controller 2500 may also allow the patient to pause or adjust therapy settings. Summary history data from each session may be saved in the device memory. Data recorded may include: start, pause, and stop times of the therapy session, scheduled or manual starts/stops, motion detector outputs, cycling detector outputs, prediction algorithm outputs, respiration timing, signal stability outputs, accelerometer outputs, impedance data from STL 1300 and RSL 1200, number of breaths, number of stimulations in a session, average and median P-P sensing impedance ("Z") amplitude values, stimulation settings and changes in stimulation settings such as core hours, pulse configuration, and ramping. These summary data allow a physician or caretaker to understand how the patient is using the device, tolerating the stimulation, troubleshoot errors in programming, and estimate the therapeutic effects of the neurostimulator. This feedback data may aid in determining if adjustments are needed to the patient's therapy (e.g. patient is ready for stimulation up-titration).

Programmer System

Figure 7A:
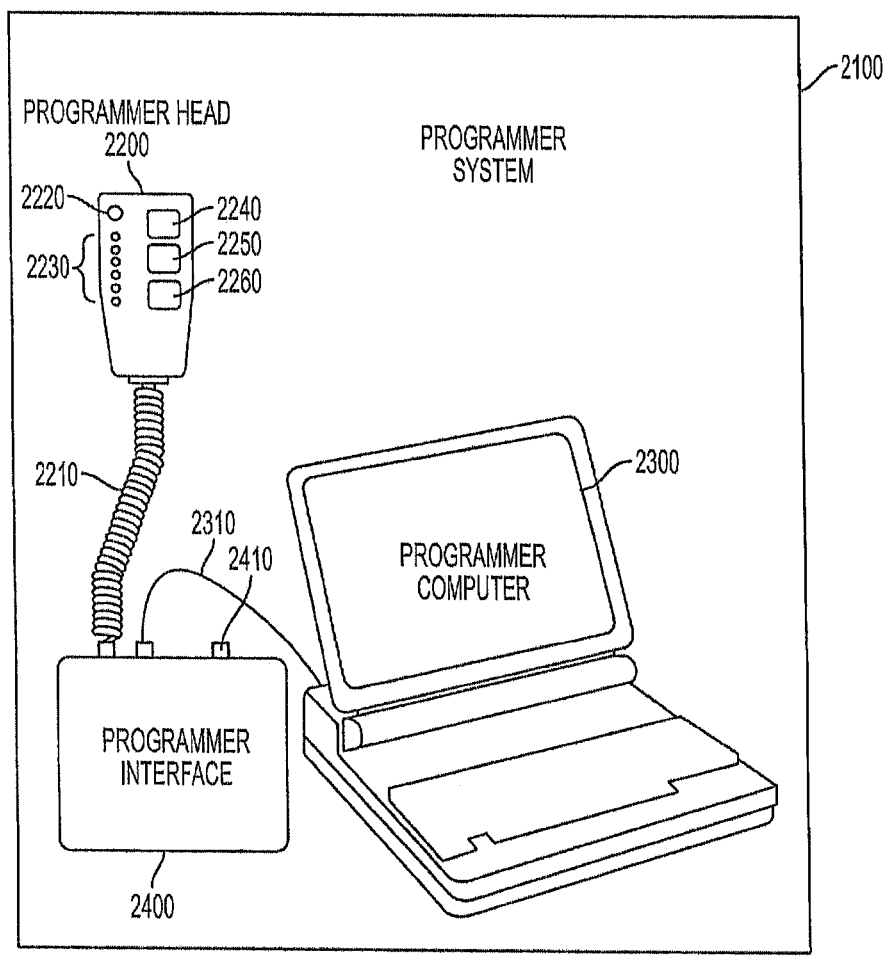
FIG. 7A is a schematic illustration of the programmer system for use in the system shown in FIG. 1.
Figure 15:
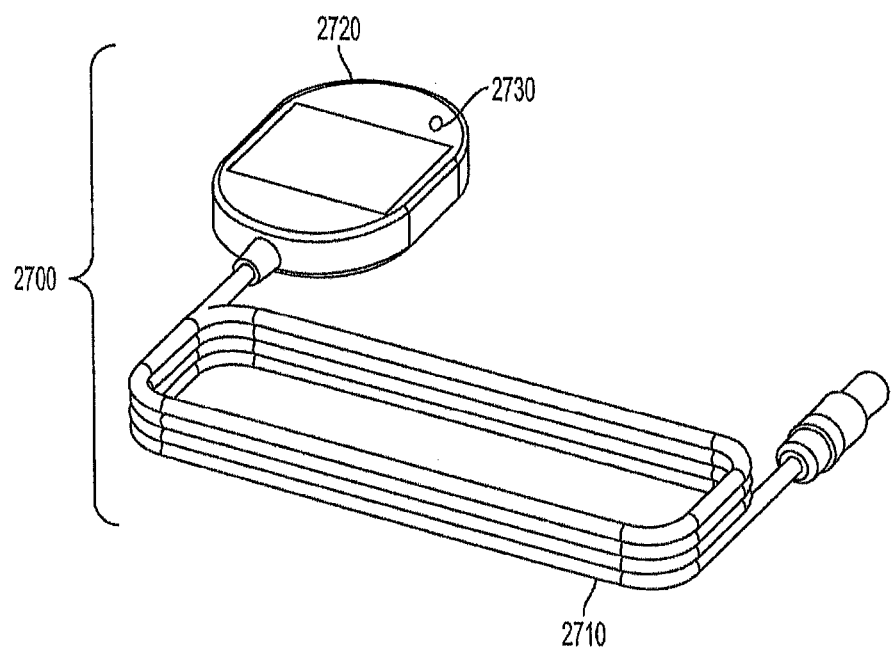
FIG. 15 illustrates a sleep wand, for wireless communication with the neurostimulator during sleep.

As shown schematically in FIG. 7A, the programmer system 2100 may include a computer 2300, a programmer interface 2400, a programmer head 2200, and a sleep wand 2700. The programmer interface 2400 and programmer head 2200 may be similar in certain aspects to commercially available programmers, which may be obtained from suitable manufacturers such as CCC Medical Devices (Montevideo, Uruguay). The programmer head 2200 may be connected to the programmer interface 2400 via a flexible cable 2210, and the programmer interface 2400 may be connected to the computer 2300 via a USB cable 2310. Cable 2210 may be coiled as shown or straight. As shown in FIG. 15, the sleep wand 2700 may comprise a sleep wand head 2720, a flexible cable 2710, and an LED 2730. The sleep wand 2700 may connect to the programmer interface 2400 via a flexible cable 2710. The sleep wand head 2720 may be 3.2 inches in length, 2.1 inches in width, and 0.5 inches deep. The programmer system 2100 may wirelessly communicate with the INS 1100 via a wireless telemetry link (e.g., 30 KHz) utilizing an antenna and associated circuitry in the programmer head 2200. The programmer may use long range telemetry such that the programmer head 2200 may rest beside the patient without interfering with sleep. The programmer interface 2400 may provide analog to digital conversion and signal processing circuitry allowing the computer 2300 to control and program the INS 1100 via the programmer head 2200. The programmer head may include a power indication LED 2220, a signal strength LED array 2230 (signal strength to/from INS 1100), an interrogate button 2240 (to upload data from INS 1100), a program button 2250 (to download data/commands to the INS 1100), and a therapy-off button 2260 (to stop therapy/stimulation output from the INS 1100). The computer 2300 may comprise a conventional laptop computer with software to facilitate adjustment of a variety of INS 1100 parameters, including, for example: stimulation parameters (stimulation pulse amplitude, stimulation pulse frequency, stimulation pulse width, stimulation duty cycle, etc.); respiration sensing algorithm parameters; stimulation trigger/synchronization algorithm parameters, therapy delivery schedule, and various test functions. The sleep wand 2700 may function like the programmer head 2200, but may be reduced in size for patient comfort during sleep. There may be one LED 2730 to indicate signal presence. Frequency of LED light pulses may indicate signal strength. The sleep wand 2700 may exclude functional buttons (i.e. interrogate command, program command, and stop therapy command) found on the programmer head 2200.

Figure 7B:
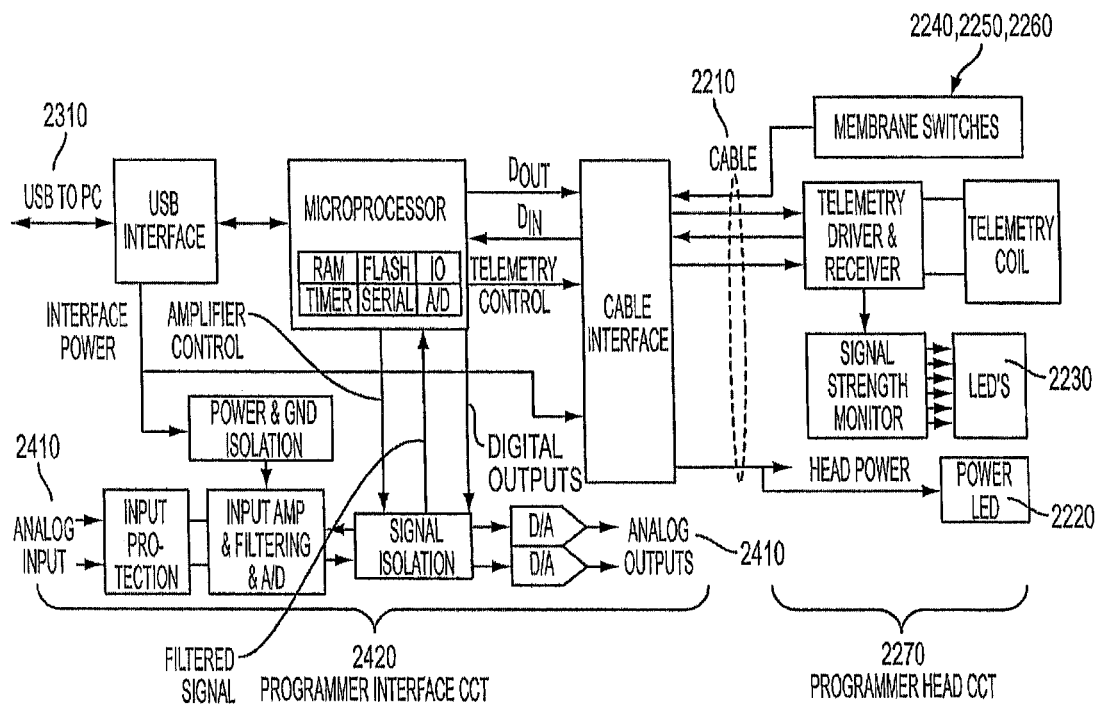
FIGS. 7B and 7C are schematic block diagrams of electronic circuitry for use in the programmer system for shown in FIG. 7A.

With reference to FIG. 7B, a block diagram of example circuits 2420/2270 for the programmer interface 2400 and the programmer head 2200 are shown schematically. The programmer interface circuit 2420 may be controlled by a microprocessor having a standard set of peripherals (RAM, flash, digital I/O, timers, serial ports, A/D converter, etc.). The microprocessor may communicate with a standard personal computer (PC) 2300 through a Universal Serial Bus (USB) interface. Commands and data may be passed from the computer 2300 to/from the microprocessor via the USB interface and cable 2310. The USB interface also may provide DC power for the programmer interface circuit 2420 and the programmer head circuit 2270 via cable 2210. The microprocessor may control the cable interface leading to the programmer head circuit 2270 via cable 2210. The programmer head circuit 2270 may contain telemetry driver and receiver electronics that interface to the telemetry coil. The telemetry coil may be designed to inductively couple signals from the programmer head circuit 2270 to the coil in the INS circuit 1130 when the programmer head 2200 is placed over the INS 1100 with the coils aligned. As an alternative to telemetry coils and an inductive link, RF antennae with associated circuitry may be used to establish a RF link to provide for arms-length telemetry. The programmer head circuit 2270 also may contain electronics that monitor the signal strength as received from the INS 1100. The outputs of the signal strength electronics drive may display LED's for the user. Another LED may indicate that power is available, for example, supplied by the computer 2300. The programmer interface microprocessor may control and receive analog input signals from an isolated sensor interface. The power and ground for the sensor interface may be derived from the USB power input, but provide DC isolation for this circuitry to prevent leakage currents from flowing through any patient connections that may be present at the sensor inputs. The sensor inputs may be protected against external high voltages (i.e. defibrillation protection). The sensor input signals may be amplified and filtered appropriately for the sensor type. The amplifier gain and filter characteristics may be controlled by microprocessor. The signals to/from the amplifier circuit may be DC isolated to prevent leakage currents from flowing through any patient connections that may be present at the sensor inputs. The sensor signals may be digitized by the microprocessor and transmitted through the USB link to the PC along with the telemetered signals from the INS 1100 for recording and display.

Figure 7C:
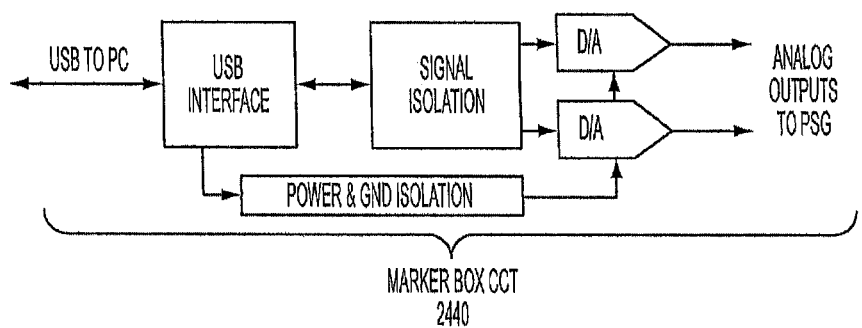
Figure 10:
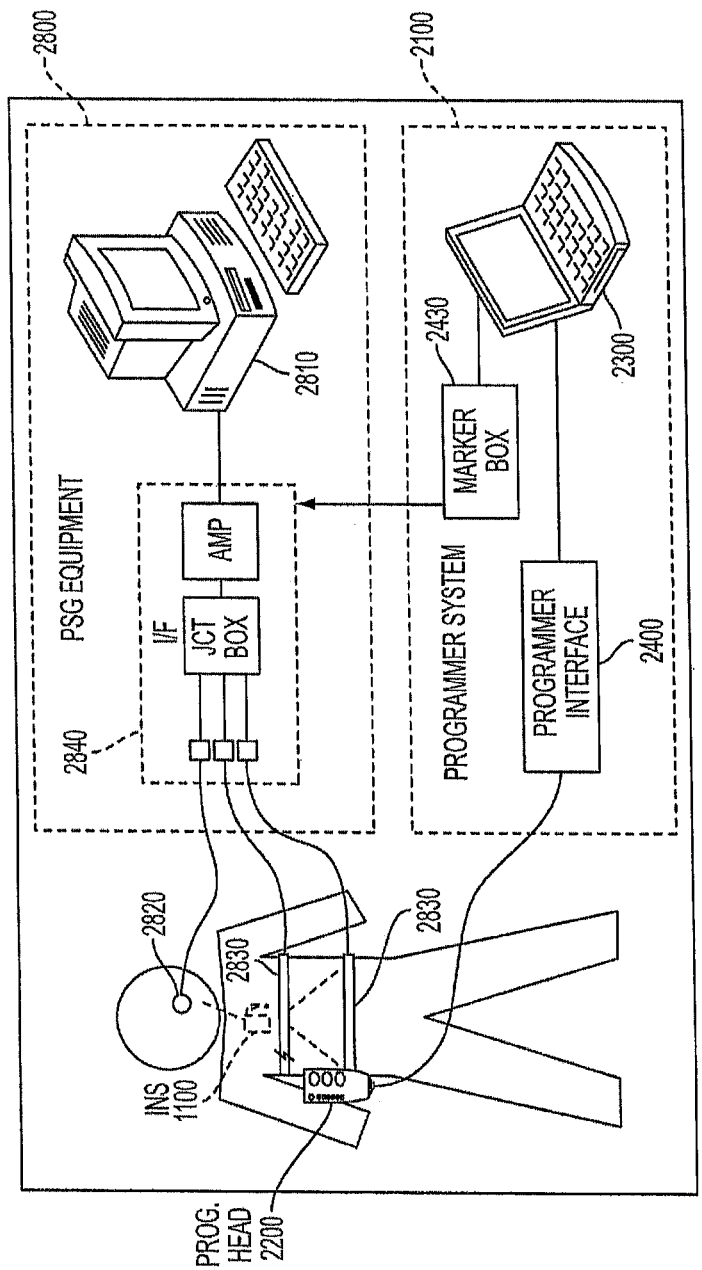
FIG. 10 is a schematic illustration of an interface of the system shown in FIG. 1 and polysomnographic (PSG) equipment as may be used in a sleep study for therapy titration or therapy assessment, for example.

With reference to FIG. 7C, a block diagram of example circuit 2440 for the marker box 2430 is shown schematically. Generally, marker box 2430 and associated circuitry 2440 may replace the D/A circuits and analog outputs 2410 of programmer interface circuit 2420 shown in FIG. 7B providing for the alternative arrangement illustrated in FIG. 10B. The marker box circuit 2440 may be separately connected to a Universal Serial Bus (USB) port of the programmer computer 2300 via a USB cable. The USB interface also may provide DC power for the marker box circuit 2440 via the USB cable. The power and ground for the marker box circuit 2440 may be derived from the USB power input, but provide DC isolation for this circuitry to prevent leakage currents from flowing through any equipment that may be connected to the patient. Analog marker output data signals may be transmitted from the PC 2300 to control the digital to analog (D/A) converter outputs. These analog output signals may be connected to standard PSG recording equipment 2800. Signals from the INS 1100 (such as sensed respiration impedance and stimulation output timing and amplitude) can be represented by these outputs to allow simultaneous recording with other standard PSG signals (flow, belts, EMG/ECG, etc). The programmer 2300 may be enabled to automatically switch programmable settings at regular time intervals, allowing respiratory sensing vectors, stimulation levels, stimulation modes, or stimulation pulse configurations to be altered at specified intervals during sleep. Sampled values may be selected such that only a limited number of settings are sampled.

As mentioned previously, the INS 1100 may record session summary data. The programmer computer 2300 may display these data using text and images to graphically display device settings, session data, and analyses of data. This data may be used to evaluate system performance and guide programming of settings. The patient's name or identifier may be stored in the INS 1100 and/or displayed on the programmer computer 2300. All text and symbols displayed by the programmer 2300 may be in a variety of selectable languages. The programmer 2300 may have the capability to connect to the internet. Through this connection files may be uploaded to a database to enable remote real time monitoring of device operation, recorded data and settings. The connection may also be used to update the programmer application software and or the (indirectly) the INS firmware.

The programmer 2300 may display and tag data to a variety of dates and times. These times may programmed to take into account daylight savings time, local time, Greenwich Mean Time, or a free-running counter in the INS 1100.

The programmer 2300 may display the voltage (or other capacity measurements) of battery 1140. In addition, an elective replacement indicator (ERI) and end of life (EOL) indicator may be displayed on the programmer as the battery nears depletion. There may be several months from ERI to EOL or alternatively, two months from ERI to EOL, with an estimated one month of use after EOL.

Therapy Controller

Figure 8A:
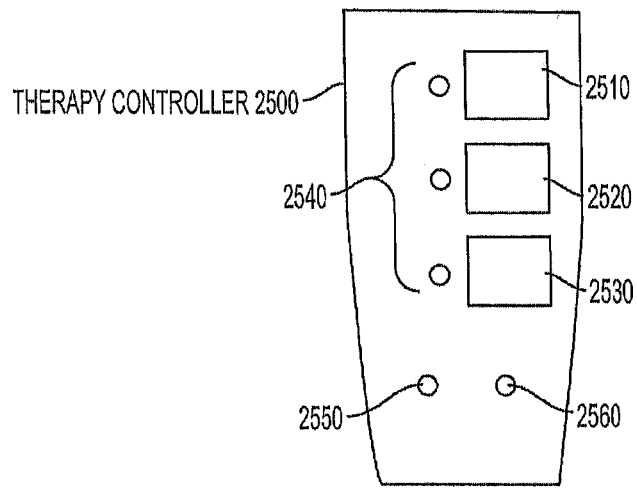
FIG. 8A is a schematic illustration of the therapy controller for use in the system shown in FIG. 1.

As shown schematically in FIG. 8A, the therapy controller 2500 may be used by the patient to control limited aspects of therapy delivery. The therapy controller 2500 may be similar in certain aspects to commercially available patient controllers, which may be obtained from suitable manufacturers such as CCC Medical Devices (Montevideo, Uruguay). The therapy controller 2500 may house a battery, an antenna, and associated circuitry (not visible) to control limited aspects of therapy delivery via a wireless telemetry link (e.g., 30 KHz) with the INS 1100. Therapy normally may be operated in a manual mode but may also be set for automatic delivery according to a predefined schedule (set by physician using the programmer during titration). The therapy controller may have a user interface including start button 2510 (to start therapy delivery), a stop button 2520 (to stop therapy delivery), and a pause button (to pause therapy delivery or reduce stimulation intensity to a programmable value), each with associated LED indicators 2540 which may flash when the corresponding button is depressed and illuminate steadily when the command is received by the INS 1100. The buttons may be backlit when pressed for ease of use at night. The user interface also may include a schedule set LED 2550 that illuminates if a therapy delivery schedule has been programmed, and a contact physician LED 2560 that illuminates in the event of a low battery or a malfunction requiring a physician visit. In addition, this light may illuminate at ERI or EOL time points.

The therapy controller may have additional functionality (e.g., more buttons) which can be set to give the patient limited control over select therapy settings. These settings include, but are not limited to, stimulation intensity (e.g., amplitude), stimulation mode, pulse train configuration, core hours stimulation settings, ramp, programmable schedule, clock, and motion inhibit programmable values.

As mentioned previously, the INS 1100 may contain data, including metrics from therapy sessions. The therapy controller 2500 may wirelessly communicate with the INS 1100 to download any data to the INS. This data may be stored in internal memory or removable memory such as a USB flash drive or smart card. This data may be uploaded (e.g. from the patient's home computer) for the physician to read. This may allow the physician to monitor device use, home efficacy, and/or the patient's acclimation.

An alternative embodiment of the user interface may include an LCD display or a touchscreen. This may allow for multiple functions to be integrated into the therapy controller while keeping the interface simple. This may also allow for larger text.

Figure 8B:
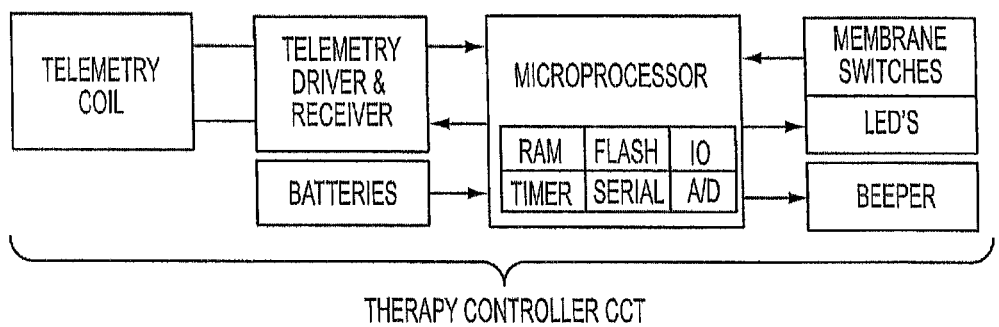
FIG. 8B is a schematic block diagram of electronic circuitry for use in the therapy controller shown in FIG. 8A.

With reference to FIG. 8B, a block diagram of an example circuit for the therapy controller 2500 is shown schematically. The therapy controller circuit 2570 may include a battery powered microprocessor having a standard set of peripherals (RAM, flash, digital I/O, timers, serial ports, A/D converter, etc.). The microprocessor may operate in a low power mode to conserve battery power. The microprocessor may control the telemetry driver and receiver electronics that interface with the telemetry coil. The telemetry coil may be designed to inductively couple signals to the INS telemetry coil when aligned. The microprocessor may monitor the membrane switches and react to switch closures by activating display LED's and initiating telemetry commands to the INS. As an alternative to telemetry coils and an inductive link, RF antennae with associated circuitry may be used to establish a RF link to provide for arms-length telemetry. After communicating with the INS, status information can be displayed to the user. The microprocessor also may control a beeper which can provide audio feedback to the user when buttons are pressed and to indicate the success or failure of communications with the INS. The beeper may have a mute function or volume control.

Magnet

Figure 9:
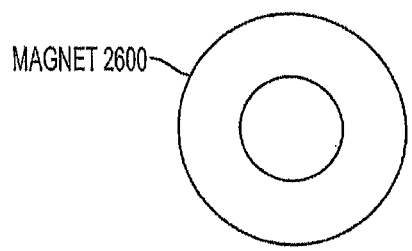
FIG. 9 is a top view of a magnet for use in the system shown in FIG. 1.

As schematically shown in FIG. 9, an annular magnet 2600 may be provided to the patient to inhibit the INS 1100 in the event the therapy controller 2500 is not available or functioning. The magnet 2600 may comprise a permanent annular-shaped magnet made of ferrite strontium material coated with epoxy. The magnet 2600 may produce a strong field of 90 Gauss at 1.5 inches from the surface of the magnet along the centerline of the hole. The magnet 2600 may be used (or carried by) the patient in case of emergency. When temporarily (2 seconds or more) placed over the implanted INS 1100 on the skin or clothing, the magnet 2600 may disable current and future therapy sessions. Although therapy sessions may be disabled by the magnet 2600, all other functions of the INS 1100 may remain enabled including telemetry communication with the programmer system 2100 and therapy controller 2500. Therapy sessions may be re-enabled using the therapy controller 2500 by initiating a new therapy session. Alternatively, the therapy may be temporarily inhibited during placement of the magnet. If left in place for a specified time period (e.g. one minute), therapy may be deactivated.

Interface with PSG Equipment

The programmer interface 2400 may include an input/output (I/O) link 2410 to allow connection to polysomnographic (PSG) equipment 2800 as schematically shown in FIG. 10A. Typical PSG equipment 2800 may include a computer 2810 connected to a plurality of sensors (e.g., airflow sensor 2820, respiratory effort belts 2830) via interface hardware 2840. The I/O link 2410 may be used in a number of different ways. For example, analog data signals from the PSG equipment 2800 may be downloaded to the computer 2300 of the programmer system 2100 to record and/or display PSG data (e.g. airflow) together with therapy data. Alternatively or in addition, digital data signals from the INS 1100 and/or the programmer system 2100 may be uploaded to the computer 2810 of the PSG equipment 2800 to record and/or display therapy data (e.g., stimulation amplitude, stimulation pulse width, and/or respiration data such as bio-impedance, vector, filter settings, prediction markers, or accelerometer data) together with PSG data. The circuitry corresponding to I/O link 2410 may be incorporated into the programmer interface 2400 as shown in FIG. 10A, or may be incorporated into a separate marker box 2430 as shown in FIG. 10B.

Synchronizing data from the sensors 2820/2830 of the PSG equipment 2800 with data from the INS 1100 via the programmer system 2100 may be beneficial to facilitate therapy titration and efficacy measurement. Although the programmer system 2100 and the PSG equipment 2800 may be directly connected by I/O link 2410, transmission delay in each system may result in asynchrony. Data synchronization between the systems may be addressed in a number of different ways. For example, if the delays in each system are relatively fixed and below an acceptable threshold (e.g., 0.5 to 1.0 second), no synchronization step need be taken. If the delays in each system are relatively fixed but above an acceptable threshold (e.g., above 0.5 to 1.0 second), data from the system with less delay may be offset (delayed) by a fixed time value to align with data from the system with more delay. As an alternative, a timing signal (e.g., from a clock signal generator separate from or integral with one of the systems) may be input into the PSG equipment 2800 and programmer system 2100 to allow time stamped data independently collected by each system to be merged and synchronized by post processing.

Treatment Overview

Figure 12A:
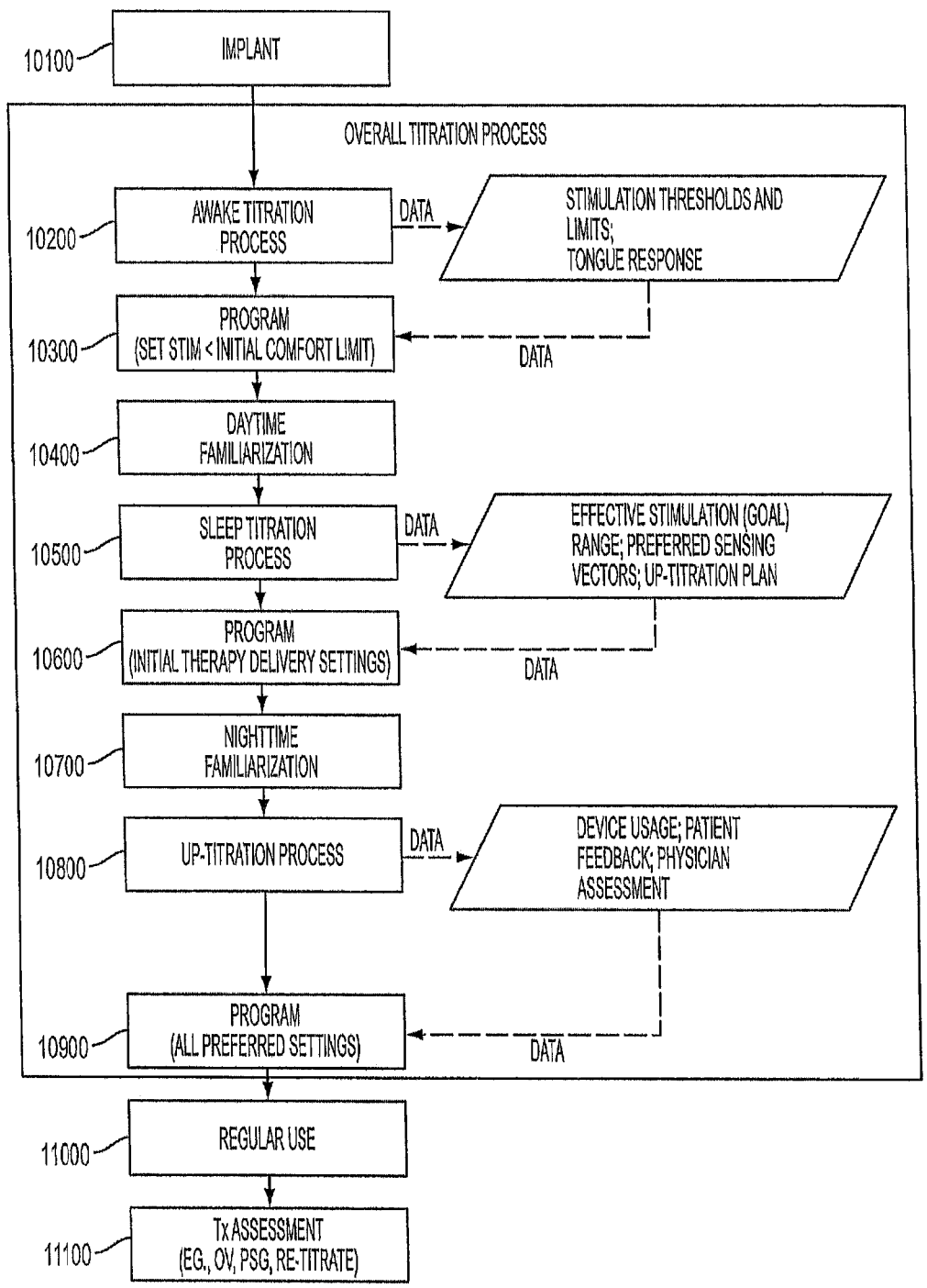
FIG. 12A shows a flowchart of an idealized therapy process and the sub-processes that may be involved.

FIG. 12A illustrates a treatment overview from implant 10100, to awake titration 10200, to daytime familiarization 10400, to sleep titration 10500, to nighttime familiarization 10700, to up-titration 10800, and finally to regular therapeutic use 11000 and therapy assessments 11100.

Figure 11A:
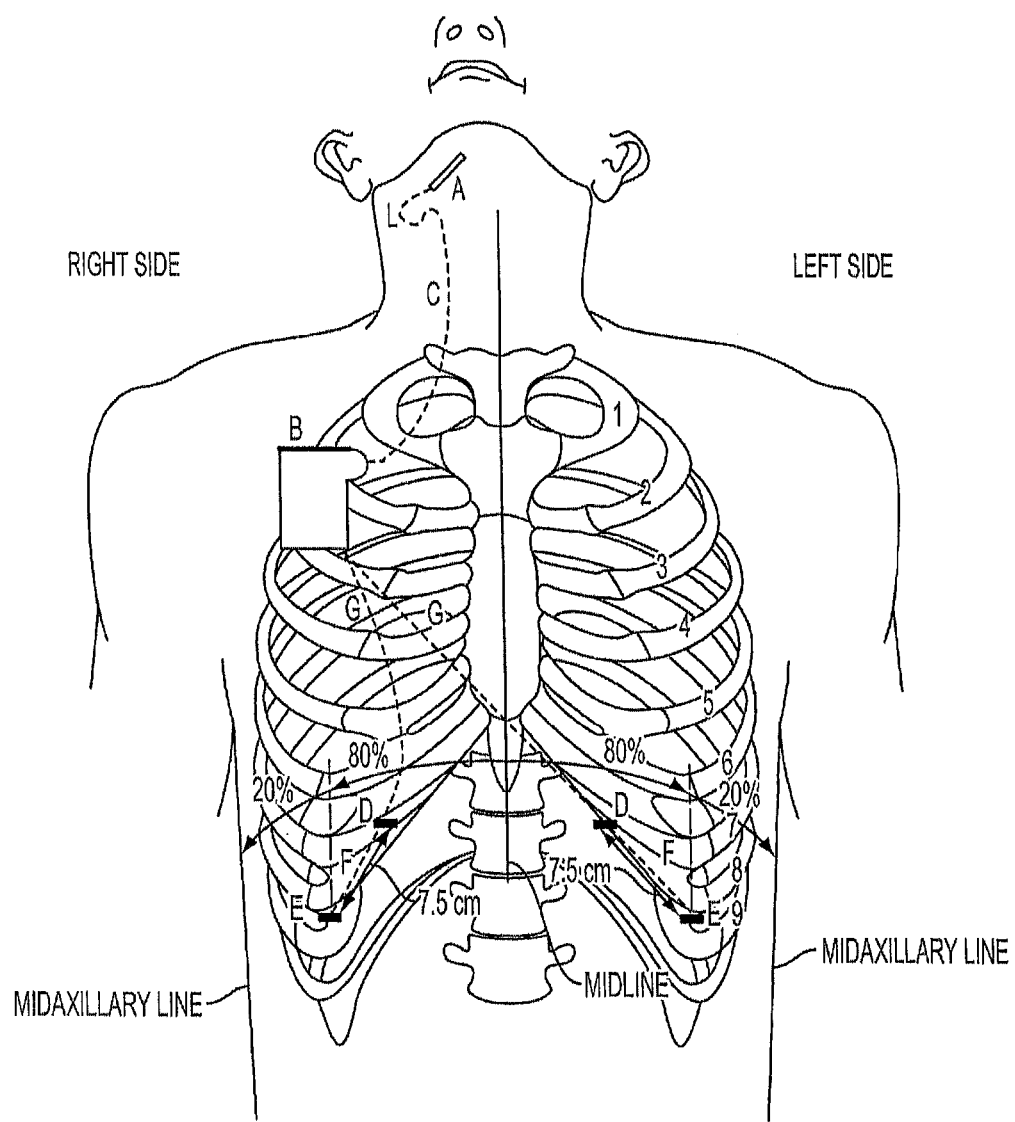
FIG. 11A is an anatomical illustration showing the incision sites and tunneling paths that may be used for implanting the internal components shown in FIG. 1.

Beginning with a surgical implant 10100, FIG. 11A schematically illustrates the incision sites (solid thick lines) and tunneling paths (dotted lines) for implanting the INS 1100, STL 1300 and RSLs 1200. The implant procedure may be performed by a surgeon (e.g., otolaryngologist) in a 1-3 hour surgical procedure with the patient under general or local anesthesia, for example. In general, the implant procedure may involve placing the cuff 1350 of the STL 1300 on the hypoglossal nerve via a submandibular dissection, and tunneling the lead body 1330 and sigmoid section 1370 of the STL 1300 subcutaneously down the neck to the INS 1100 in a subcutaneous pocket in the infraclavicular region.

From the infraclavicular pocket, the RSL 1200 may be tunneled subcutaneously toward midline and then laterally along the costal margins.

Figure 12B:
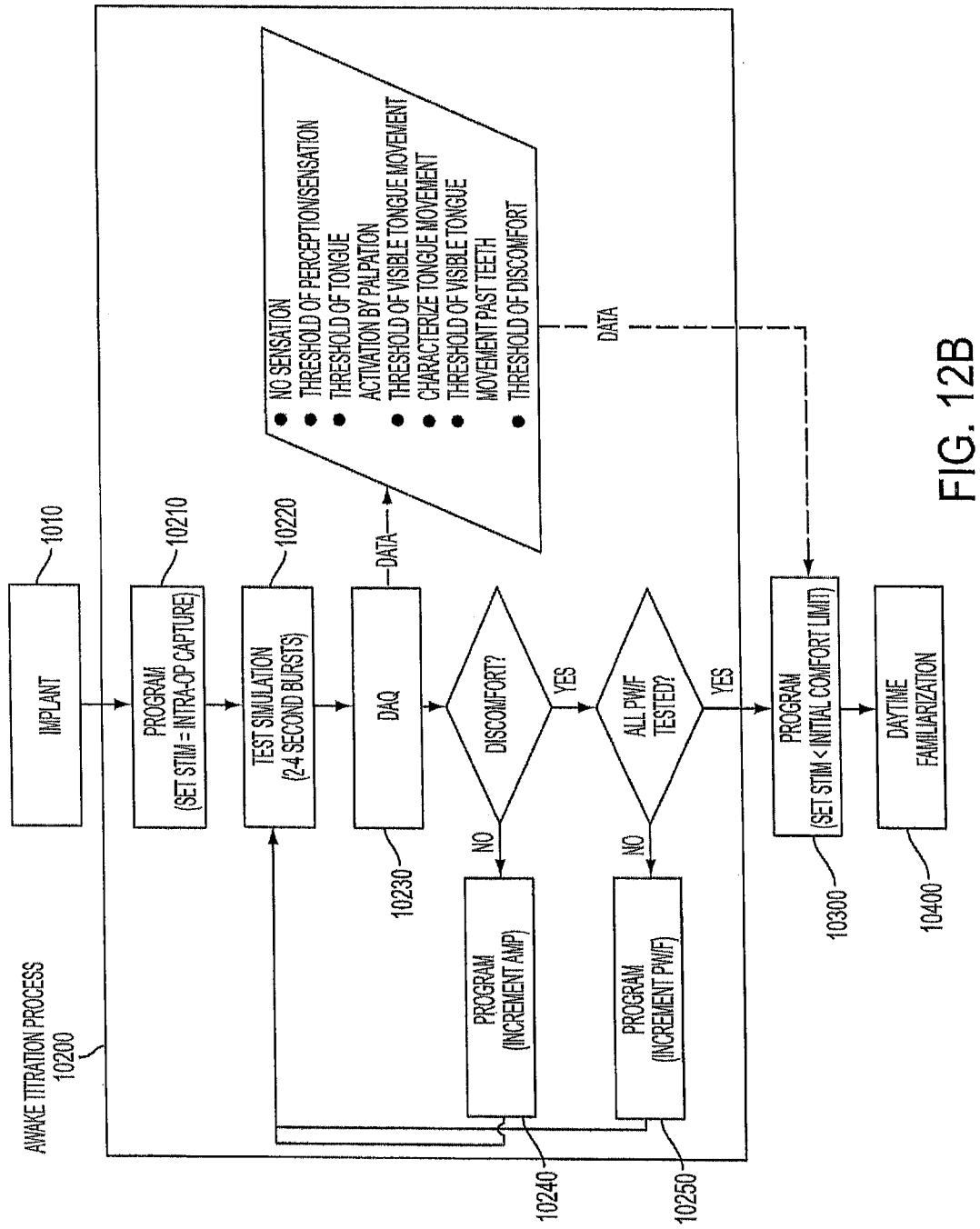
FIGS. 12B, 12C, and 12D show detailed flowcharts of idealized therapy sub-processes shown in FIG. 12A.

After a healing period of a few weeks, an awake titration may be performed 10200 wherein the patient's tongue response to stimulation is observed over a range of comfortable stimulations, as illustrated in FIG. 12B. In addition, a global system check may be performed to check the system integrity. The patient may then be sent home for a period of daytime familiarization 10400 where the patient may turn on stimulation during wakefulness to introduce the sensation of stimulation. The patient subsequently may return to the sleep lab for a sleep titration 10500 where a sleep technician, under the supervision of a certified sleep physician (e.g., pulmonologist), may use the programmer system 2100 to program the INS 1100 (e.g., set the therapy delivery schedule and titrate the stimulus to determine a range of efficacious settings during sleep). After the sleep titration, the patient may return home and begin the nighttime familiarization (acclimation) and therapy up-titration process, wherein stimulation may be increased over time to an efficacious range. For example, the patient may leave the sleep titration with stimulation programmed to turn on at 1.7 mA and stimulation may be increased by 0.1 mA at two week intervals up to a goal setting of 2.0 mA.

Immediately after the titration visit, the patient may return home and begin using the device at the programmed stimulation level during nighttime familiarization 10700. A therapy delivery session may begin when the therapy controller 2500 is used to manually start, stop, and pause a therapy session. This may be beneficial when the patient has an irregular sleep schedule. At the beginning of a therapy delivery session, stimulus may be delayed for a period of time to allow the patient to fall asleep. The therapy delivery session may be programmed to not exceed a fixed number of hours (e.g., eight hours). In addition, a therapy delivery session may begin according to the pre-defined therapy delivery schedule, which may be set to coincide with when the patient normally goes to sleep. The therapy delivery session may end according to the pre-defined therapy delivery schedule, which may be set to coincide with when the patient normally wakes up, or with a manually stop command from the therapy controller. The patient may use the therapy controller 2500 to adjust limited aspects of therapy delivery as defined previously.

Tunneling System

Figure 11B:
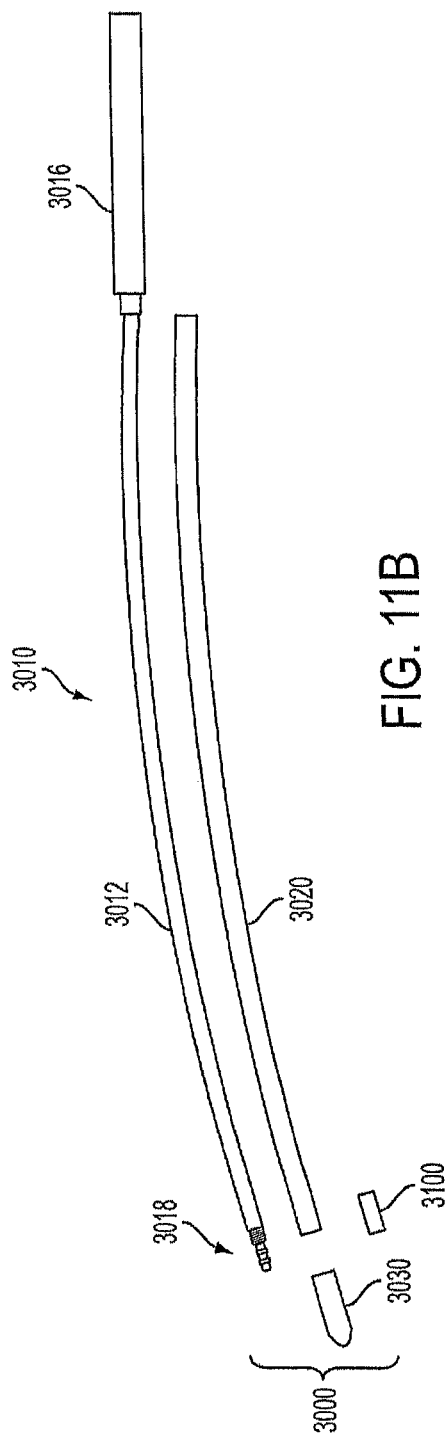
FIG. 11B is a perspective view of a disassembled tunneling tool for use in tunneling the leads of the system shown in FIG. 1.
Figure 11C:
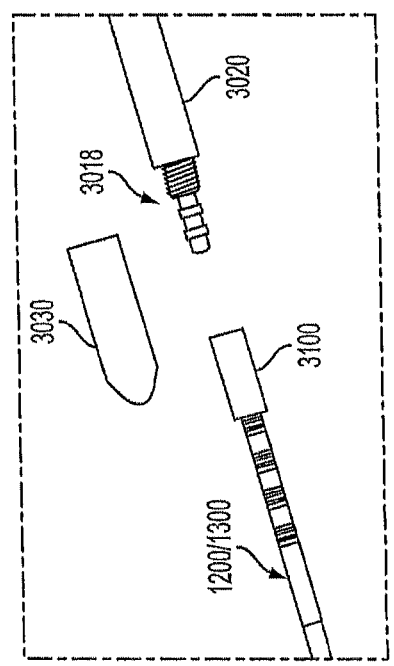
FIG. 11C is a detailed perspective view of the assembled tunneling tool shown in FIG. 11B, but with the cap removed to expose the distal connector for attaching to the lead carrier disposed on the proximal end of a lead.

FIGS. 11B and 11C schematically illustrate the tunneling system 3000 which may be used for tunneling the STL 1300 or RSL 1200. The tunneling system 3000 may include a relatively rigid tool 3010, a tubular sheath 3020, and a tip 3030, and lead carrier 3100.

The tool 3010 may be formed of stainless steel and include a handle 3016, a shaft 3012, and a distal connector 3018. The connector 3018 may include threads that mate with corresponding threads in the tip 3030. The connector 3018 may also include ring barbs that form an interference fit with the inside of the lead carrier 3100 for releasable connection thereto. The lead carrier 3100 may also form an interference fit with the RSL proximal connector 1210, the STL proximal connector 1310, or a distal ring electrode of the RSL 1250 or 1260.

The sheath 3020 may be sized to be slid over the tool 3010 and secured in place via the tip 3030. The tip 3030 may include a radiopaque agent such as barium sulfate loaded at 18% by weight, for example.

The lead carrier 3100 may comprise a small polymeric tube with an inside diameter sized to form an interference fit with the distal connector 3018, the RSL proximal connector assembly 1210, an RSL distal electrode 1250 or 1260, or the STL proximal connector assembly 1310. During tunneling, the proximal end of the lead carrier 3100 may attach to the distal connector 3018 and the distal end of the lead carrier 3100 may attach to the RSL proximal connector assembly 1210, an RSL distal electrode 1250 or 1260, or the STL proximal connector assembly 1310.

The sheath 3020 may comprise a polymeric tube with two open ends, and the tip 3030 may comprise a polymeric tube with one threaded end and one closed end for blunt dissection. The proximal end of the tip 3030 may include internal threads to screw onto the connector 3018 and hold the sheath 3020 on the shaft 3012.

In the embodiment shown in FIGS. 11B and 11C, the tool 3010 may have a pre-bend length of 17.1 inches and a post-bend length of 16.9 inches. The sheath 3020 may have an outside diameter of approximately 0.28 inches, a pre-bend length of 12.4 inches and a post bend length of 12.25 inches. The shaft 3012 may have a diameter of about 0.22 inches, a pre-bend length of 12.375 inches, and a post-bend length of 12.231 inches, sufficient to fill the length of the sheath 3020. The handle 3016 may have a diameter of about 0.5 inches and a length of about 3.50 inches. The tip 3030 may have an outside diameter tapering from approximately 0.13 inches and a length of about 1.0 inches.

Surgical Implant Procedure

With continued reference to FIG. 11A, the internal components 1000 may be implanted using the following surgical procedure 10100, which is given by way of example, not limitation. Unless specifically stated, the order of the steps may be altered as deemed appropriate. Although the INS 1100 may be surgically implanted on the right or left side, implantation on the right side may leave the left side available for implantation of cardiac devices that are traditionally implanted on the left side. In at least one exemplary embodiment, the right side is used for the RSL 1200 to provide a clean respiratory signal that is less susceptible to cardiac artifact than the left side.

Standard surgical instruments may be used for incisions, dissections, and formation of subcutaneous pockets. Commercially available nerve dissection instruments may be used for dissecting the hypoglossal nerve and placing the STL cuff 1350 on the nerve.

The patient may be prepared for surgery using conventional practice including standard pre-operative care procedures, administration of antibiotics as appropriate, and administration of steroids as appropriate to reduce swelling around the nerve dissection. Because tongue movement may be observed during test stimulation, in at least one exemplary embodiment, no long-acting muscle relaxants are used during surgical preparation or during implant. General anesthesia may be administered according to conventional practice and the patient may be intubated using an endotracheal tube, taking care to position the endotracheal tube so that the tongue is free to protrude during test stimulation.

The neck may then be extended to expose the right submandibular region, and a sterile field is created around the neck and thorax, taking care to avoid obstructing visualization of the oral cavity (a clear sterile drape over the mouth may be used). By way of a neck incision (A), the hypoglossal nerve may then be exposed deep to the submandibular gland. Because the INS 1100 may be implanted on the right side to minimize cardiac artifact during respiratory sensing, this dissection may also be performed on the right side. A region of the hypoglossal nerve, for example excluding the branch that innervates retrusive muscles (e.g.

styloglossus or hyoglossus), may then be identified and isolated. Confirmation of correct nerve location may be achieved by performing a test stimulation later in the procedure. The identified nerve branch may then be circumferentially dissected to accommodate the cuff 1350. The short side 1352 of the cuff 1350 may be designed to reside on the deep side of the nerve, and the long side 1354 of the cuff 1350 may be designed to reside on the superficial side of the nerve.

The appropriate sized cuff 1350 may then be selected based on the nerve diameter at the intended location for cuff placement. Nerve size may be assessed using reference size (e.g., forceps of known width), a caliper, or a flexible gauge that wraps around the nerve, for example. The cuff 1350 may then be opened and placed around the nerve. The strap 1356 on the cuff 1350 may be used to facilitate placement of the cuff 1350 around the nerve. A curved forceps may be placed under the nerve to grasp the strap 1356 and gently pull the cuff 1350 onto the nerve. The strap 1356 may then be placed through the loop (buckle) 1358 on the cuff 1350. The cuff 1350 may be available in two sizes (small and large), and the small cuff may have an indicator mark (not shown) on the strap 1356 that should be visible after insertion through the loop 1358. If a small cuff is selected and the indicator mark does not pass through the loop, the small cuff may be too small and should be replaced with a large cuff.

A strain relief loop (L) in the STL 1300 may then be created by arranging approximately 6 cm of the STL sigmoid body 1370 in a C-shape inside a small subcutaneous pocket formed via the neck incision (A) by blunt dissection superficially along the lateral surface of the digastric muscle in a posterior direction.

The surgeon may then verify that the cuff 1350 is not pulling or twisting the nerve, and that there is contact between the inside of the cuff 1350 and the nerve.

A test-stimulation may then be performed to confirm correct positioning of the cuff 1350 on the nerve. To conduct a test-stimulation, the proximal end of STL 1300 may be plugged into the INS 1100, and the programmer system 2100 may be used to initiate a test stimulation signal delivered from the INS 1100 to the nerve via the STL 1300. The test stimulation may be performed while observing, for example, tongue movement by direct visual observation, airway caliber by nasal endoscopy, fluoroscopy, cephalogram, etc. Correct placement of the cuff on the nerve may be confirmed by, for example, observing tongue protrusion, an increase in retro-glossal airway caliber, an increase in retro-palatal airway caliber, an increase in stiffness of the anterior and/or lateral walls of the retro-glossal airway with or without an increase in airway caliber, anterior movement without superior movement of the hyoid bone, among others. Incorrect placement of the cuff on the nerve is indicated, for example, when there is insufficient opening of the retro-palatal or retro-lingual space, when the tongue is observed to retract (posterior movement), a decrease in retro-glossal airway caliber, a decrease in retro-palatal airway caliber, superior movement, and for example unilateral superior movement of the hyoid bone, among others. If necessary, the cuff 1350 may be repositioned at a different location along the length of the nerve to obtain the desired effect. The capture threshold and impedance values may be recorded and the STL 1300 may be disconnected from the INS 1100. The surgeon may create a fascia wrap by suturing fascia around the cuff on the superficial side of the nerve.

A pocket for the INS 1100 may then be created by making an incision (B) down to the pectoralis fascia approximately 2 finger breadths below the right clavicle. The INS 1100 may be implanted on the right side to minimize cardiac artifact during respiratory sensing. Blunt dissection inferior to the incision may be used to create a pocket large enough to hold the INS 1100. The pocket should be inferior to the incision (B) such that the incision (B) does not reside over the INS 1100 when later placed in the pocket.

A tunnel may be formed for the STL 1300 using the tunneling system 3000 (sheath 3020 and tip 3030 placed over tool 3010) to tunnel along a path (C) from the infraclavicular INS pocket to the neck incision (A). As shown in FIG. 11C, the lead carrier 3100 may then be placed on the most proximal electrical contact of the STL proximal connector 1310. The tip 3030 may be removed from the sheath 3020 to expose the connector 3018 of the tool 3010 and attach to the lead carrier 3100. While holding the sheath 3020 in place, the tool 3010 may be pulled proximally to pull back the STL 1300 through the sheath 3020, taking care not to pull out the C-shaped strain relief or disturb the cuff. If the C-shaped strain relief loop (L) is pulled out, it should be replaced into the small pocket. The tool 3010 may be released from the lead carrier 3100 and the lead carrier 3100 may be removed from the STL 1300. The sheath 3020 may then be removed from the body leaving the STL 1300 in place. The neck incision (A) need not be closed at this time, but rather may be closed later in the procedure allowing confirmation that the C-shaped strain relief remains in the small pocket.

The following implant instructions refer to an INS 1100 implanted at the patient's right sub-clavicular region. The right and left distal portions of the RSL 1200 may be placed near the right and left costal margins, respectively, by making four small incisions (D and E) as shown. The lateral incisions (E) may be made approximately 80% (+/-5%) of the distance from the midline to the mid-axillary line, and on the costal margin. The medial incisions (D) may be made such that the RSL 1200 is relaxed and all electrodes are on the costal margin. Using the tunneling system 3000 (sheath 3020, tip 3030 attached via connector 3018), a tunnel (G) may be formed between the pocket (B) and the medial incision (D), such that the right distal portion of the RSL 1200 may be pulled through the tunnel (G) from the pocket (B) to the medial incision (D). A tunnel (F) may then be formed between the medial incision (D) and lateral incision (E), such that the right distal portion of the RSL 1200 may be pulled through the tunnel (F) from (D) to (E). This may be repeated for the left distal portion of the RSL 1200. Alternatively, if the embodiments of RSL 1200 shown in FIG. 4F or 4G are used, a small pocket may be formed medial to (D) in order to accommodate the medial electrodes and/or loop back region 1255.

The previously described tunneling operations (F and G) may be performed as follows: The tunneling tool 3010 including the connector 3018 may be inserted into the sheath 3020 and the tip 3030 may be connected to the connector 3018, forming the tunneling system 3000. The tunneling system may be placed in the origination incision site and pushed beneath the skin towards the destination incision site, forming a tunnel. After tunneling, the tip 3030 may be removed from the connector 3018 of the tunneling tool 3010. If needed, the tool 3010 may be removed and reversed such that the connector 3018 is at the other end of the sheath 3020. With the tool 3010 inserted through the sheath 3020, the lead carrier 3100 may be attached on its proximal end to the connector 3018 and on its distal end to the distal electrode 1250 or proximal connector 1210 of the RSL 1200. While holding the sheath 3020 in place, the tunneling tool handle 3016 may be pulled and the attached lead carrier 3100 and RSL 1200 pulled into the sheath 3020. This may be visualized through the semi-transparent tunneling tool. The sheath 3020 may then be slid towards the tunneling tool handle 3016, exposing the lead carrier. The lead carrier may then be disconnected from the connector 3018, leaving the RSL 1200 in place. This process may be used to tunnel from (D) to (B) and subsequently from (E) to (D). For tunnel (G), the RSL 1200 may be pulled completely through the sheath 3020 to expose and disconnect the lead carrier.

Each anchor tab 1270 and suture hole 1290 may be secured to the underlying tissue by dissecting down to the adjacent muscle fascia and suturing each anchor tab 1270 or suture hole 1290 to the muscle fascia. Permanent sutures may be used to avoid movement of the RSL 1200, and braided suture material may be used for knot retention and to prevent corrosion through the silicone anchors.

The STL 1300 and RSL 1200 may then be connected to the INS 1100. The RSL 1200 may be plugged into the RSL port 1112, and the STL 1200 may be plugged into the STL port 1114. The set screws may be tightened using a torque wrench.

A closed loop test may be performed to confirm proper operation by observation of tongue protrusion or airway opening in concert with inspiration. The INS 1100 and proximal portions of the leads 1200/1300 may then be placed into the infraclavicular pocket, looping the excess lead length beneath or around the INS 1100. Care should be taken not to pull out the C-shaped strain relief loop (L) in the STL sigmoid lead body 1370 while manipulating the INS 1100 into place. The INS 1100 may then be sutured to underlying fascia through both suture holes 1116 found in the header 1110 of the INS 1100. Permanent sutures may be used to avoid movement of the INS both before tissue encapsulation and chronically, and braided suture material may be used for knot retention. Another system test may be performed at this point. After confirming that the C-shaped strain relief loop (L) is present in small pocket at neck incision, the incisions may be irrigated (optionally with an antibiotic solution) and closed using conventional techniques. After a healing period of approximately one month, the patient may undergo a sleep study to confirm proper operation of the system and to titrate therapy.

Screening Methods

As described previously, obstructive sleep apnea (OSA) can be characterized by periodic reductions in airflow during sleep and, more specifically, as periodic reductions in inspired air volume during sleep. These reductions in airflow and inspired air volume are respiratory events that may be categorized as hypopneas (less severe) or apneas (more severe). Such respiratory events may reduce the amount of gas exchanged in the lungs during respiration or the efficiency of that gas exchange, thereby negatively affecting the exchange of oxygen and CO2. Due to the human body's natural metabolism of oxygen and generation of CO2, a reduction in the exchange of oxygen and CO2 can lead to a reduction in blood oxygen levels and a corresponding increase in blood CO2 levels. When CO2 levels reach a threshold, the person can be aroused from sleep briefly (for less than 10 seconds) or for an extended duration (for more than 10 seconds). After sleep is reinitiated, this progression of respiratory events may repeat, leading to a disruptive sleep pattern. This repeating can be expressed as a respiratory event rate or as an apnea-hypopnea index (AHI) and may be measured as the sum of apneas and hypopneas experienced over a period of sleep divided by the hours of sleep.

Respiratory events occurring during a polysomnography (PSG) evaluation may be characterized by observed reductions in airflow (including apneas and hypopneas) as well as by measured reductions in blood oxygen levels or blood oxygen saturation levels, and by the detection of full or partial arousals from sleep. The sleep data collected from the PSG evaluation or from another method (such as with the use of a user-operated or patient-managed device that is mobile and/or home-based and capable of measuring one or more sleep-related parameters), including airflow and blood parameter measurements, can be generated or recorded with a log of the respiratory events providing the timing, severity, sleep status or state, and other characteristics associated with each respiratory event or with the entire sleep period. Each of these types of respiratory events can be a factor in determining the apnea-hypopnea index (AHI). Airflow and reductions in airflow may be measured using methods described previously (e.g. a pressure sensor connected to nasal cannula, an oral thermistor/thermocouple, a pneumotach, etc.). Measures of blood oxygen levels, blood oxygen saturation levels, and reductions in blood oxygen and blood oxygen saturation levels can be obtained or derived from measurements of SpO2, SaO2, or PaO2. The most common blood oxygen measurement technique used during a PSG evaluation is SpO2 as measured by pulse oximetry. Of the available techniques for measuring oxygen levels in the bloodstream during sleep, the measurement of blood oxygen saturation levels has been found to be useful. A reduction in blood oxygen saturation levels occurring during sleep may be called an oxygen desaturation or simply an O2 desaturation, and that a reduction in blood oxygen saturation levels as measured by SpO2 may be called a SpO2 desaturation. For example, a change in blood oxygen saturation levels from a 97% blood oxygen saturation level to a 93% blood oxygen saturation level can be called a 4% O2 desaturation because the blood oxygen saturation level was reduced by 4% during a time period associated with an observed respiratory event. For example, the exemplary 4% O2 desaturation can be associated with a time period that precedes and leads up to an arousal, or associated with a time period that precedes and leads up to a significant reduction in airflow, or associated with a time period that precedes and leads up to a particular severity level of the observed desaturation. Arousals are typically measured by electroencephalogram (EEG) and are visually scored by an experienced sleep technician.

It is believed that there have been a variety of proposed definitions for respiratory events, with the most debate over the definition of hypopnea. The American Academy of Sleep Medicine (AASM) endorsed the AHIChicago hypopnea definition in 1999. In 2007, the AASM proposed two new hypopnea definitions: a recommended AHI (AHIrec) and an alternative AHI (AHIalt) definition. In 2012, the AASM modified the hypopnea definition yet again. Each hypopnea definition proposes different combinations and thresholds of severity for airflow reductions, SpO2 desaturation, and arousal.

For example, the AHIrec hypopnea definition requires at least a 30% reduction in airflow for at least 10 seconds and a corresponding O2 desaturation of at least 4%. Such a hypopnea does not require an EEG arousal.

In another example, the AHIalt hypopnea definition requires at least a 50% reduction in airflow for at least 10 seconds and one or both of the following conditions: an EEG arousal or a corresponding O2 desaturation of at least 3%. If there is an EEG arousal, no O2 desaturation is needed to score the hypopnea. Likewise, if there is an O2 desaturation of 3% or more, no EEG arousal is needed to score the hypopnea.

Regardless of the AHI definition applied, many respiratory events will have an associated oxygen desaturation. However, some respiratory events will not have an associated oxygen desaturation, and some respiratory events may be identified solely by the detection of an oxygen desaturation without the presence or detection of other indicators. An oxygen desaturation rate, commonly known as oxygen desaturation index (ODI), is the total number of oxygen desaturations of a given severity divided by the hours of sleep for the observed sleep period. For example, a person who sleeps 8 hours and has 400 oxygen desaturations of 3%-or-greater severity during those 8 hours would have a 3%-ODI (alternatively expressed as "ODI_3%") value of 50/hour, a number calculated from a count of 400 O2 desaturations of 3%-or-greater severity divided by the 8 hours of the 8-hour sleep period over which the 400 O2 desaturations were observed. Stated another way, the exemplary value of an "ODI_3% value of 50/hour" means that the patient experienced an average of 50 desaturations of a 3%-or-greater severity for each hour of sleep of an observed sleep period. As can be appreciated, in this example, some of these 400 3%-or-greater oxygen desaturations may have a severity that is greater than 3%, which allows for calculations of ODI values for different severities of O2 desaturation. For example, if 200 of the 400 3%-or-greater oxygen desaturations have a severity of 4% or greater, then the corresponding ODI value (ODI_4%) would be 25/hour (i.e., 200 oxygen desaturations of 4% or greater severity divided by 8 hours of the 8-hour sleep period). These calculations can continue for ever-increasing severities. For example, if 40 of the oxygen desaturations had a severity of 6% or greater, and 24 of the oxygen desaturations had a severity of 8% or greater, then the ODI_6% and ODI_8% values would be 5/hour and 3/hour, respectively. As expected, increases in the ODI severity level (here from 3%, to 4%, to 6%, to 8%), will likely have corresponding ODI rate decreases (here from 50, to 25, to 5, to 3 per hour). As can be appreciated, the ODI calculation method described above can produce a flat or decreasing trend as the ODI severity level increases, because qualifying desaturations drop out of the ODI calculations as the ODI severity level increases. As can be further appreciated, the above-described ODI calculation method is a cumulative (or anti-cumulative) technique wherein each of the lower ODI severity levels includes values corresponding to the selected level combined with values that correspond to greater ODI severity levels, e.g., the calculation of the ODI_3% value includes all of the oxygen desaturations corresponding to ODI_4%, ODI_5%, etc. In an alternative ODI calculation method using a discrete technique, the calculation of each ODI severity level can be limited to include only those oxygen desaturations corresponding to the selected ODI severity level. For example, in this alternative approach, the calculation of the ODI_3% value can be limited to oxygen desaturations corresponding to a range of 3.0% to 3.9% and not include oxygen desaturations that correspond to values of 4.0% or greater. Such a calculation method would likely show a reduction of ODI values as severity increases, because most patients have more low-level oxygen desaturations than high-level oxygen desaturations, although some patients with sleep apnea may desaturate to more severe levels more often than less severe levels. As can be appreciated, the range applied to each ODI severity level can vary. For example, the ODI_3% value can correspond to a range of 2.5% to 3.4% with the 3.0% value disposed in the middle of that range, or some other arrangement that achieves the same ends.

Figure 16:
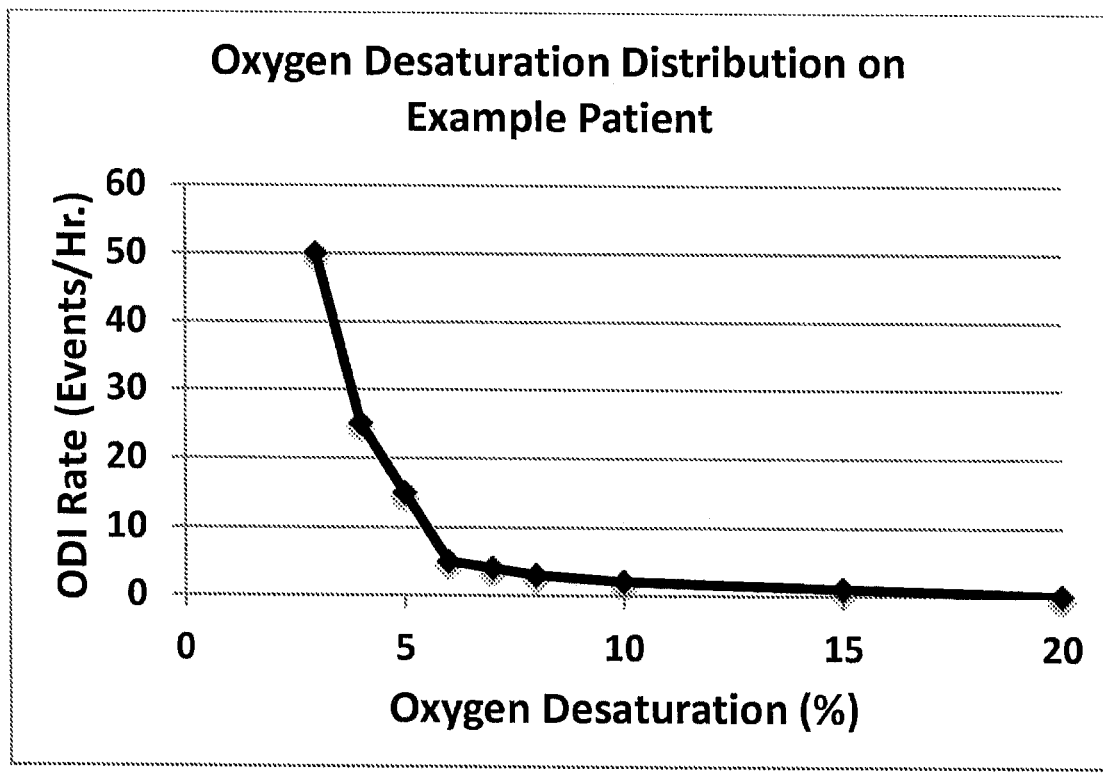
FIG. 16 illustrates an example oxygen desaturation curve.

These data, using any of the above ODI calculation methods, may be well suited to plotting on Cartesian coordinates. For example, the x-axis may display the ODI severity thresholds (e.g. 3%-20%) and the y-axis may display the ODI rate (e.g. desaturations per hour). FIG. 16 illustrates an example of the cumulative method where the ODI rates provided above (50 to 25 to 5 to 3 per hour) are plotted with additional values to display an exemplary patient having ODI rate values of 50, 25, 15, 5, 4, 3, 2, 1, and 0 events/hour are shown to correspond to ODI severity thresholds of 3%, 4%, 5%, 6%, 7%, 8%, 10%, 15%, and 20%). These plots are referred to generally as an oxygen desaturation distribution curves. An exemplary data set that could have generated the plot of FIG. 16 can have an 8-hour sleep period with an observation of 400 O2 desaturations of 3% or greater severity, 200 O2 desaturations of 4% or greater severity, 120 O2 desaturations of 5% or greater severity, 40 O2 desaturations of 6% or greater severity, 32 O2 desaturations of 7% or greater severity, 24 O2 desaturations of 8% or greater severity, 16 O2 desaturations of 10% or greater severity, 8 O2 desaturations of 15% or greater severity, and no O2 desaturations of 20% or greater severity. From the exemplary data sets for the patient represented by FIG. 16 or from similar data sets, a mean oxygen desaturation value can be derived and additional methods can be employed to identify one or more alternative representations of the oxygen desaturation values for a patient (e.g., a mean oxygen desaturation value).

As can be appreciated from FIG. 16, the number of observed O2 desaturations can vary from the exemplary numbers provided above while still supporting the same curve illustrated in FIG. 16. For example, instead of a value of 40 O2 desaturations for a 6% or greater severity (described above), a value of 38 O2 desaturations of 6% or greater severity could have been observed and rounded up to 40 when preparing the oxygen desaturation distribution curve of FIG. 16. Alternatively, the value of 38 may be used for calculations, while the corresponding value may be plotted or recorded. Apparent in the ODI calculation is the understanding that the numerator of the ODI rate (the counting of observed O2 desaturations) and the denominator of the ODI rate (the length of the sleep period) will influence the calculation of the ODI rate. As can be appreciated, the definition applied to the identification and counting of observed and excluded O2 desaturations and the identification and measurement of the sleep status and sleep period of the patient can vary and otherwise influence the calculation of the ODI rate and the plotting of the oxygen desaturation distribution curve.

Using the methods described above and similar methods, sleep data can be subdivided further, for example by sleep stage, position, or other factors. Using the above example, the person sleeping eight hours may have slept four of those hours supine and four of those hours non-supine (e.g. sleeping on the right side, left side, or prone). Each of these positions can be further subdivided by sleep stage (e.g. Stage 1, Stage 2, Stage 3, and REM). Stages 1-3 are collectively known as non-REM (NREM). Thus, if 3 of the 4 hours of supine sleep were spent in Stages 1-3, then total sleep time for supine-non-REM sleep is three hours. Similar calculations can be performed for other stage-position combinations, stage-only (e.g. NREM and REM), position-only (e.g. supine, non-supine, right, left, prone), or other metric (e.g. stimulation ON/OFF, stimulation amplitude, CPAP pressure, etc.). Thus, for each of these subsets, ODI calculations can be made with varying complexity (e.g. ODI_4% in non-supine position, ODI_6% in supine position with NREM stage sleep and with stimulation turned on, etc.).

In a clinical study, the subjects who were least likely to meet responder criteria exhibited a marked tendency for severe oxygen desaturations at their baseline PSG study. Specifically, while most subjects exhibited oxygen desaturation events within a narrow range of desaturation severity, challenging subjects (subjects that did not respond or had a reduced response to therapy) often had oxygen desaturations that were heavily skewed toward more severe desaturation levels. This correlation between desaturations and responsiveness to therapy may provide a predictor of the efficacy of the therapy, and also provide an indication as to how well a subject has responded or will respond to the therapy.

There are several methods available to characterize these severe desaturations. For example, the calculation of a mean oxygen desaturation value can provide an estimate of the average severity of oxygen desaturations. A low threshold (e.g. 3%) may be used to account for a plethora of small fluctuations in oxygen level (e.g. 0.5%) that may overwhelm the data set.

One way to screen out these fluctuations is to include only oxygen desaturations that are associated with an observable respiratory event when calculating the values described above. Although the data may vary slightly depending on the AHI definition applied, the trends will likely be similar. This is because respiratory events with severe oxygen desaturations usually meet the criteria for a respiratory event, regardless of definition.

Other methods can be also be used to characterize oxygen desaturation severity. Similar to mean oxygen desaturation, the median and mode of the oxygen desaturation distribution may provide similar characterization. In addition, the lowest oxygen level observed during a PSG (e.g. the SpO2 nadir) can be used. Curve-fitting methods may also characterize the oxygen desaturation curves, as described above. Examples of curve fitting methods include linear regression and exponential curve fitting. Many other curve fitting examples are conceivable. Additionally, time during sleep spent below threshold oxygen and oxygen saturation levels (e.g. 90%, 85%, etc.) can also characterize the severity. Similarly, the average SpO2 value during sleep can also be calculated to characterize the severity.

The graphical method illustrated in FIG. 16 is an embodiment illustrating the characterization of the oxygen desaturation severity for an exemplary patient. When comparing the oxygen desaturation distribution curves of multiple subjects implanted with a hypoglossal nerve stimulation device, differences in morphology suggests two distinct sub-groups. This is illustrated in FIG. 17.

Figure 17:
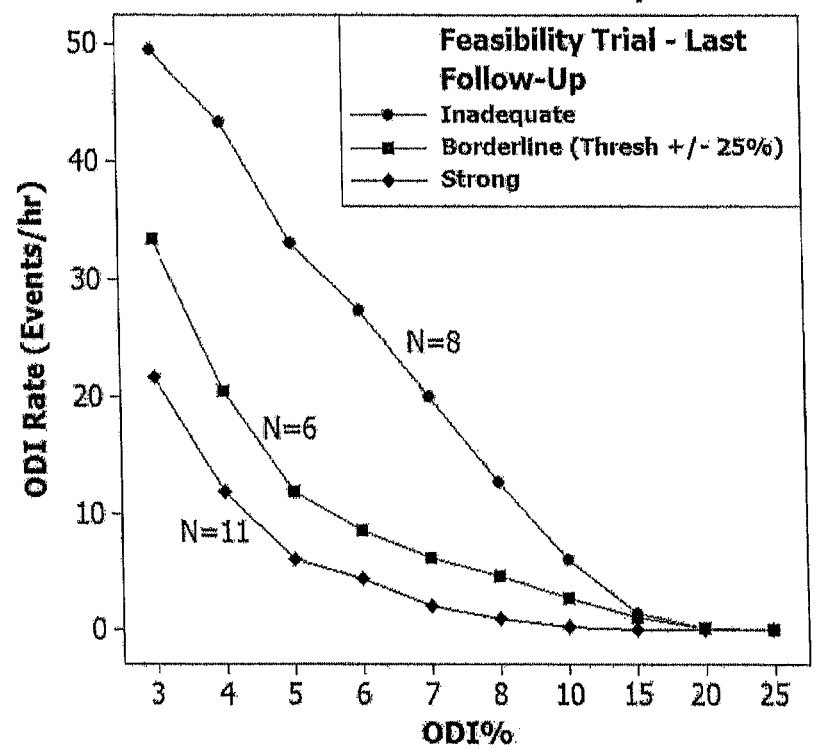
FIG. 17 provides oxygen desaturation curve data for twenty-five subjects from a clinical trial, sub-divided by therapeutic response.

The data plotted in FIG. 17 represents twenty-five evaluable subjects from a clinical study. A hypoglossal nerve stimulation (HGNS) system similar to the system described in FIG. 1 was implanted in each subject. Prior to implant, each subject had a baseline PSG. The oxygen desaturation distribution curve for each subject was determined. Follow-up PSG data was collected on all subjects. Each subject's response to HGNS therapy was characterized based on the most recent scored PSG. Each subject was categorized as a "strong" responder, "borderline" responder, or "inadequate" responder to the HGNS therapy. These designations were based on each subject's response threshold. For this study, to meet responder criteria, each subject's AHI was less than or equal to 20 and at least a 50% improvement compared to data obtained from the baseline PSG. Other responder criteria, however, is conceivable. For example, one could use at least a 50% improvement in AHI only or ODI_4% of less than or equal to 5/hr as possible responder criteria.

For the responder criteria used in this clinical study, if two subjects had baseline AHIs of 30 and 50, for example, then their responder AHI thresholds would be 15 and 20, respectively, representing a 50% improvement to the baseline values that is also less than or equal to 20. If a subject was within 25% of this threshold, they were categorized as "borderline." Continuing with the two example subjects with AHI thresholds of 15 and 20, respectively, their borderline range would be AHIs inclusively ranging from 11.25/hour to 18.75/hour and inclusively ranging from 15/hour to 25/hour, respectively. If a subject's AHI was above this "borderline" range, they were characterized as an "inadequate" responder to the HGNS therapy. If a subject's AHI was below this "borderline" range, they were characterized as a "strong" responder to the HGNS therapy.

As shown in FIG. 17, there were twenty-five evaluable subjects. Eleven subjects were categorized as "strong" responders. Six subjects were categorized as "borderline" responders. Eight subjects were categorized as "inadequate" responders. FIG. 17 shows the median oxygen desaturation distribution curve for each of these sub-groups. The oxygen desaturation distribution curves for the "strong" and "borderline" sub-groups have a similar morphology to each other. The morphology of the "inadequate" responder sub-group is different; it is skewed to the right and has a higher degree of linearity. These two distinct morphologies suggest a different phenotype, patient profile, or underlying mechanism.

This "inadequate" sub-group of the OSA population may be more challenging to treat with HGNS and can be screened out by analyzing the oxygen desaturation profile collected during a baseline PSG (prior to implant with an HGNS system). Thus, subjects with severe oxygen desaturations, the least likely to respond to HGNS therapy, can be screened out prospectively. Stated another way, inclusion criteria for an HGNS system may require mild to moderate oxygen desaturations corresponding to the "strong" and "borderline" sub-groups. Given the plethora of methods to characterize oxygen desaturation severity, other thresholds and criteria are available. One embodiment is mean oxygen desaturation associated with respiratory events. As expected, the higher the mean oxygen desaturation threshold, the more likely that challenging subjects with severe oxygen desaturations will satisfy the criteria. Example severity thresholds include values equal to, greater than, or less than 3%, 4%, 5%, 6%, 7%, and 8%, and can further include thresholds of values equal to, greater than, or less than 9%, 10%, 11%, 12%, 13%, 14%, 15%, 16%, 17%, 18%, 19%, 20%, 21%, 22%, 23%, 24%, and 25%. Based on empirical data and with reference to FIG. 17, subjects with mean oxygen desaturations (associated with respiratory events) below 5% are associated with the "borderline" or "strong" sub-groups and are likely to respond to a HGNS therapy, those inclusively between 5% and 8% are less likely to respond to HGNS therapy, and those above 8% are associated with the "inadequate" sub-group and are unlikely to respond to a HGNS therapy. As can be appreciated from FIG. 17, at ODI_10% and higher, the ODI rates for the three sub-groups are similar. At ODI_10% all three sub-groups provide an ODI rate that is less than 10 events/hour but still has the "strong" sub-group being distinguishable from the other two sub-groups (with $ODI\_10\%_{strong}=1$ event/hr, $ODI\_10\%_{borderline}=4$ events/hr, and $ODI\_10\%_{inadequate}=6$ events/hr). And at ODI_15%, ODI_20%, and ODI_25% all three sub-groups provide ODI rates that are either identical or within a range of 3 events/hours (with ODI_15%$_{strong}$=near 0 events/hr, ODI_15%$_{borderline}$=near 0 events/hr, and ODI_15%$_{inadequate}$=2 events/hr, and with all values of ODI_20% and ODI_25% near zero). In contrast, as illustrated in FIG. 17, at ODI_8% all three-sub-groups provide an ODI rate that is less than 15 events/hour but the "inadequate" sub-group provides an ODI rate that is distinguishable from the other two sub-groups (with ODI_8%$_{strong}$=2 events/hr, ODI_8%$_{borderline}$=5 events/hr, and ODI_8%$_{inadequate}$=13 events/hr). Likewise, at ODI_7% the "inadequate" sub-group provides an ODI rate of 20 events/hour and is distinguishable from the other two sub-groups that provide ODI rates that are less than 10 events/hour (i.e., the "borderline" and "strong" sub-groups have ODI rates that are 50% or less of the corresponding ODI rate for the "inadequate sub-group") (with ODI_7%$_{strong}$=3 events/hr and ODI_7%$_{borderline}$=6 events/hr). Again, referring again to FIG. 17, at ODI_6% the "inadequate" sub-group provides an ODI rate of more than 25 events/hour and is distinguishable from the other two sub-groups that provide ODI rates that are less than 10 events/hour (i.e., the "borderline" and "strong" sub-groups have ODI rates that are 40% or less of the corresponding ODI rate for the "inadequate sub-group") (with ODI_6%$_{strong}$=5 events/hr, ODI_6%$_{borderline}$=9 events/hr, and ODI_6%$_{inadequate}$=26 events/hr). At ODI_5% the "inadequate" sub-group provides an ODI rate of more than 30 events/hour and is distinguishable from the other two sub-groups that provide ODI rates that are less than 15 events/hour (i.e., the "borderline" and "strong" sub-groups have ODI rates that are 50% or less of the corresponding ODI rate for the "inadequate sub-group") (with ODI_5%$_{strong}$=6 events/hr, ODI_5%$_{borderline}$=12 events/hr, and ODI_5%$_{inadequate}$=33 events/hr). At ODI_4% the "inadequate" sub-group provides an ODI rate of more than 40 events/hour and is distinguishable from the other two sub-groups that provide ODI rates that are 20 events/hour or less (i.e., the "borderline" and "strong" sub-groups have ODI rates that are 50% or less of the corresponding ODI rate for the "inadequate sub-group") (with ODI_4%$_{strong}$=12 events/hr, ODI_4%$_{borderline}$=20 events/hr, and ODI_4%$_{inadequate}$=43 events/hr). At ODI_3% the "inadequate" sub-group provides an ODI rate of 50 events/hour and is distinguishable from the other two sub-groups that provide ODI rates of less than 35 events/hour for the "borderline" sub-group and less than 25 events/hour for the "strong" sub-group (i.e., the "borderline" sub-group has an ODI rate that is 70% or less of the corresponding ODI rate for the "inadequate sub-group", and the "strong" sub-group has an ODI rate that is 50% or less of the corresponding ODI rate for the "inadequate sub-group") (with ODI_3%$_{strong}$=22 events/hr, ODI_3%$_{borderline}$=33 events/hr, and ODI_3%$_{inadequate}$=50 events/hr).

As can be further appreciated from FIG. 17, the curvatures of the "borderline" and "strong" sub-groups are similar from ODI_3% to ODI_25% and, in particular, closely aligned from ODI_5% to ODI_8%. In contrast, the curvature of the "inadequate" sub-group is not similar or aligned between ODI_5% and ODI_10% as the slope for the "inadequate" sub-group is steeper than the slopes of the "borderline" and "strong" sub-groups. For example, for the "strong" sub-group, the slope between ODI_5% and ODI_8% is 1.33 (the absolute value of a rise of −4 (ODI rate of 2 at ODI_8%−ODI rate of 6 at ODI_5%) divided by a run of 3 (ODI_8%−ODI_5%)) and for the "borderline" sub-group the slope between ODI_5% and ODI_8% is 2.33 (the absolute value of a rise of −7 (ODI rate of 5 at ODI_8%− ODI rate of 12 at ODI_5%) divided by a run of 3 (ODI_8%−ODI_5%)). In contrast, for the "inadequate" sub-group the slope between ODI_5% and ODI_8% is 6.67 (the absolute value of a rise of −20 (ODI rate of 13 at ODI_8%−ODI rate of 33 at ODI_5%) divided by a run of 3 (ODI_8%−ODI_5%)). Comparatively, the slope of the "inadequate" sub-group (6.67) is five times or greater than the slope of the "strong" sub-group (1.33), which is a comparison that can be expressed mathematically as: slope$_{inadequate}$>Y times slope$_{strong}$, where "Y" is 5, 4, 3, 2, or 1 or a number provided between these values. Using a similar comparison, the slope of the "inadequate" sub-group (6.67) is 2.75 times or greater than the slope of the "borderline" sub-group (2.33), which is a comparison that can be expressed mathematically as: slope$_{inadequate}$>X times slope$_{borderline}$, where "X" is 2.75, 2, or 1 or a number provided between these values. These data are based on a patient group of only 25 subjects who were selected using specific screening criteria. Thus, the ranges and ratios discussed herein could in fact be broader in the general population or apneic population, for example.

These findings should increase the likelihood of therapeutic success and increase clinical efficacy results. As health economics continue to play an ever-increasing role in the medical device field, findings like these are increasingly valuable. This is because large costs can be avoided, namely the costs of implanting subjects who are poor candidates.

Identifying and distinguishing the three sub-groups ("strong", "borderline", and "inadequate", or any other sub-groups separating HGNS-responders from HGNS-non-responders) in the available data (PSG or otherwise) can be achieved in a number of ways. Likewise, a value representative of the oxygen desaturations experienced by a patient can be obtained in a number of ways, such as by generating a mean oxygen desaturation value or a median oxygen desaturation value as described above. One possible way to evaluate patient responsiveness to HGNS therapy is to obtain the mean oxygen desaturation value for a patient and then to manually compare the mean or median O2 desaturation value to the desaturation threshold described above (in which, for example, responders are patients with mean oxygen desaturations below 5% and non-responders are patients with mean oxygen desaturations above 8%).

Automated methods are also available for the processing of sleep and PSG data and for determining whether a patient is a responder or a non-responder for HGNS therapy. For example, a website can be provided with a functionality that provides an indication as to whether a patient is a candidate for implantation of a nerve stimulation device—e.g., a determination as to whether a patient or a set of sleep data for a patient indicates status as a responder or non-responder. The website can include a function that allows a sleep lab, patient, or a user-operated, sleep measurement device, such as a mobile or home-based sleep measurement device, for example, to upload sleep data to a server, can include a function that processes the sleep data to determine whether the patient or the sleep data indicates status as a responder or non-responder, and can include a function that displays the responder/non-responder status to a user. The sleep lab, patient, or user-operated sleep measurement device, such as a mobile or home-based sleep measurement device, for example, can pre-condition the sleep data, or the website can have a function that pre-conditions the sleep data, to allow for a more efficient or more standard evaluation of the sleep data. In another alternative, any of the above functionality of the website, or its equivalent, can be provided via a mobile application, as a stand-alone software product, or as a firmware product, or as an update made to an existing system provided at a sleep lab or other device. In a further alternative, the functionality can be provided as a feature on a physician or patient programmer such as the programmer system 2100 or the therapy controller 2500 illustrated in FIG. 1. In another alternative, the functionality can be implemented with the transmission of the sleep data to a remote server that provides the functionality, with the sleep lab, patient, or user-operated sleep measurement device, such as a mobile or home-based sleep measurement device, for example, transmitting the sleep data and/or the provider of the functionality receiving the sleep data and/or providing a determination to the sleep lab, patient, or a clinician. In yet another alternative, the functionality can be coupled with a blood oxygen monitoring or sensing device configured to measure blood oxygen levels, blood oxygen saturation levels, and reductions in blood oxygen and blood oxygen saturation levels, or a device configured to measure SpO2, SaO2, or PaO2 as described above. Such a blood oxygen monitoring device, which may be a stand-alone, user-operated device, can be implemented to interact with a website, software, an app or any of the other implementation of the functionality as described above. In a further alternative, in at least some embodiments, the processing of sleep and PSG data and the determining whether a patient is a responder or a non-responder for nerve stimulation therapy may be accomplished manually and/or with a calculator.

Additional screening can be used to supplement the above-described methods. For example, the airway can be characterized during sleep by a Pcrit measurement in differing sleep stages and body postures, per the methods of Schwartz et al. A higher Pcrit value is indicative of a more collapsible airway which may be more difficult to treat with this therapy. A surrogate measure for Pcrit may be an auto-PAP device that adjusts airway pressure dynamically to eliminate flow limitation. For example, a patient may require 12 cmH$_2$O of air pressure to maintain a patent airway in the supine position, yet only require 8 cmH$_2$O of air pressure in the lateral position. The auto-PAP would automatically adjust for this.

The volume of air expired during a pressure drop may be measured. The pressure drop may occur during natural expiration during wakefulness. Alternatively, the patient may be asleep during the measurement. The timing of the pressure drop during expiration may occur at a certain point during expiration to ensure consistency. The duration of the pressure drop may be fixed. An example of this measure is $V_{NEP\_0.5}$.

The airway may be visualized using an imaging modality such as, but not limited to, cephalogram, MRI, fMRI, CT, ultrasound, OCT, naso-endoscopy, photography, and video imaging. This imaging may be performed during sleep, under sedation, or during wakefulness. The patient may be asked to protrude the tongue, inhale/exhale at specific flow rates, or perform Muller's Maneuver. Tongue protrusion force may also be measured. Tongue size may be observed and/or measured quantitatively or qualitatively (e.g., Modified Mallampati). BMI may also be a good predictor of patient response.

The following metrics (and others) may be measured and used in screening: size of tongue and soft palate, angle of the soft palate, redundancy of tissue, and length of soft palate. Endoscopy is one method for obtaining these metrics. Additional size metrics may include craniofacial structures, tonsil size, adenoids, and/or pharyngeal fat pads.

Mechanical linkage or coupling between airway structures may also be assessed. For example, airway opening may be measured at different levels concurrent with other motions, (e.g. measuring opening of the airway at the retro-palatal space during voluntary tongue protrusion or anterior displacement of the tongue).

Nasal airway collapse may be measured using nasal peak inspiratory flow meters in different body positions, for example. Additionally, acoustic rhinometry may provide another way to measure this.

Body Mass Index (BMI) may be a useful tool in screening. Additional metrics include % body fat, % visceral fat, neck circumference, % neck fat, and/or body fat distribution.

A patient's arousal threshold from sleep may be quantified by measuring intra-pleural arousal pressure. A nasal EPAP device may be used in screening. An EPAP device reduces airflow through the nares. This may increase airway patency during the expiratory phase of respiration. An example of EPAP is the ProVent device (Ventus Medical Inc., Belmont Calif.). Arousals and respiratory events may be assessed with and without the EPAP device. During therapy, the patient's tongue may protrude past the teeth. A dental examination (i.e. identify sharp teeth), patient's use of dentures, and tolerance to oral appliances may be used in screening.

The airway may be characterized using a dual air pump and a valve system, configured for connection to a mask on the patient. In this configuration, the two different pressures (e.g., difference of 1 cm H$_2$O) are maintained by each pump which is connected to the valve. The valve may be attached via a tube to the mask such that the pressure at the mask is from only one of the pumps. The valve may then be automated to alternate between the two pressures at a programmable rate (e.g., 1 Hz). This allows the airway to fluctuate between pressures within breaths. An airway may be characterized by lowering the pressure to a level that brings flow limitation, and then observing what pressures remove this flow limitation.

Awake Titration

As described previously, the patient may undergo an awake titration 10200, an iterative process where the response to stimulation is documented over a range of comfortable stimulation levels (FIG. 12B). These stimulations may be delivered manually (e.g., 2 second commanded stimulation bursts) or synchronous with respiration. A range of amplitudes may be tested across multiple frequencies (range of 20 to 50 Hz, nominal 40 Hz), and pulse widths (range of 30 to 215 µs, nominal 90 µs) 10220.

The awake titration may involve defining a wake-stimulation operating window, defined at its lower limit by a capture threshold and at its upper limit by a discomfort threshold. The capture threshold may be defined as the lowest stimulation level at which muscle contraction is visible, palpable, or perceptible (e.g., gross tongue movement or stiffening) is observed. The discomfort threshold may be defined as the lowest stimulation level at which the patient experiences an unacceptable sensation (e.g., discomfort, pain) while awake.

While determining this range, the patient may be in the supine position or alternatively, in a posture typical of sleep. In general, during the stimulation titration, one may begin with the lowest settings for pulse width (30 µs) and amplitude (0.4 mA) at a nominal frequency (40 Hz). If stimulation produces pulsatile (vibrating) contractions, the frequency may be increased to 50 Hz. The pulse width is incrementally increased to 60 µs, then to nominal (90 µs), keeping Amplitude at 0.4 mA. With the pulse width set to 90 µs, amplitude may be iterated according to the process described hereinafter. If maximum amplitude is reached and additional intensity is required, the pulse width may be increased while reducing amplitude to minimum (0.4 mA). If maximum pulse width (215 µs) is reached and additional intensity is required, frequency may be increased while reducing the pulse width to 90 µs and the amplitude to minimum (0.4 mA).

At each stimulation level, observations may be recorded such as: visible tongue motion, palpable genioglossus muscle contraction, perception of muscle movement, tongue protrusion, tongue retrusion, tongue depression, tongue flattening, tongue cupping, and/or tongue protrusion past the teeth 10230.

After awake titration 10200, the patient may be sent home at a stimulation level in this operating range, beginning the daytime familiarization period 10400. This may occur prior to the sleep titration night, such that the patient may acclimate to the sensation of stimulation. This may allow higher levels of stimulation to be assessed during the sleep titration without patient arousal. Patients have been observed to tolerate (i.e., not arouse) higher stimulation intensities while asleep compared to wakefulness, so the arousal threshold may be higher than the wake discomfort threshold.

Sleep Titration

As described previously, after implantation and a healing period of approximately one month, the patient may undergo a sleep (PSG) study to confirm proper operation of the system and to titrate therapy stimulation levels 10500. Titration may utilize the set-up illustrated in FIG. 10, wherein the programmer system 2100 interfaces with the PSG equipment 2800. Generally, an oro-nasal mask may be used in order to measure airflow. Alternatively, a nasal cannula may be used. In at least one exemplary embodiment, a calibrated pneumotach is used with the oro-nasal mask to measure the patient's airflow 10510. Alternatively, an uncalibrated pneumotach may be used. A thermistor or a thermocouple may also be used to sense airflow. The thermistor or thermocouple may be calibrated or uncalibrated.

Figure 14:
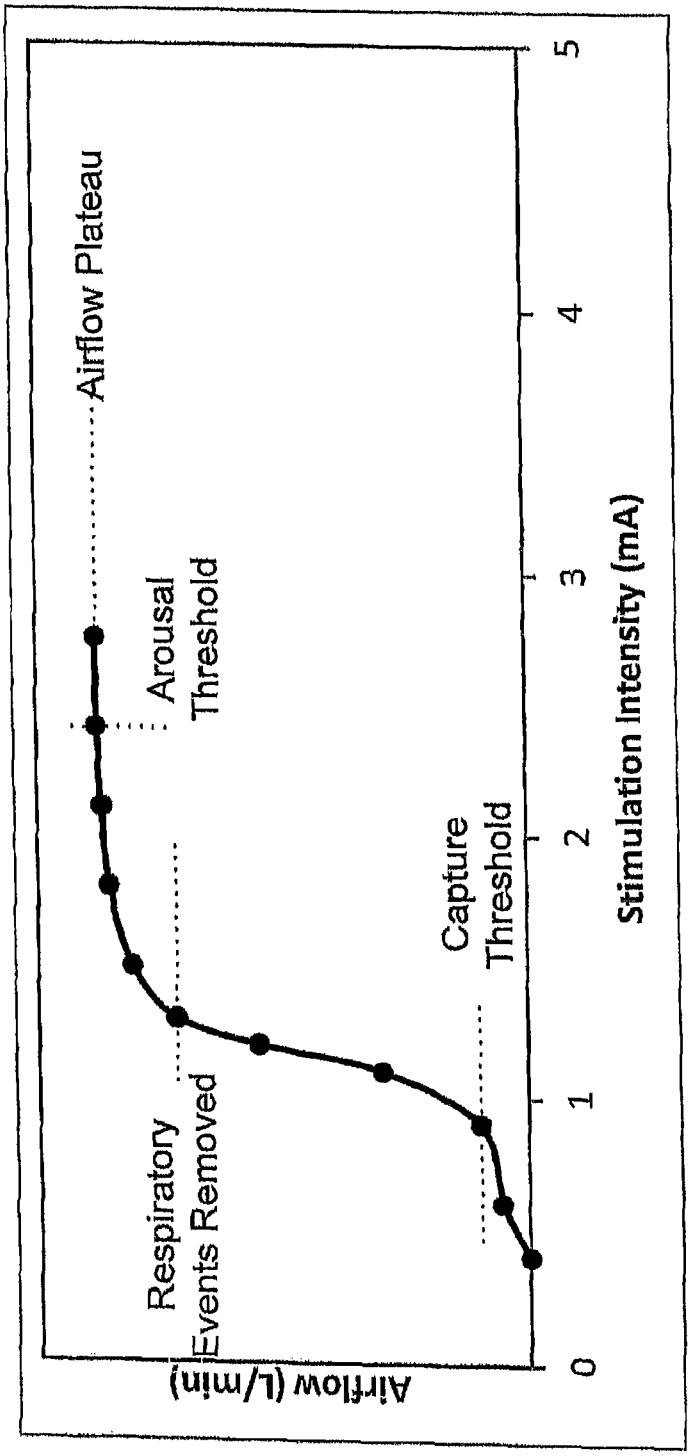
FIG. 14 illustrates an example of the effect of stimulation on airflow.

FIG. 14 illustrates an example of a patient's airflow response to stimulation. As shown in FIG. 14, the inspired airflow increases as stimulation delivered to the nerve increases. The airflow capture threshold is the stimulation level at which an increase in airflow is first observed. As stimulation continues to increase, muscle (i.e. genioglossus) activation and airflow also increase. Prior to full muscle activation, a stimulation level which first removes respiratory events is observed. At full muscle activation, increasing stimulation does not increase airflow, resulting in an airflow plateau. The patient may arouse due to stimulation at a level on the plateau. Data comprising this curve may be acquired during a sleep titration PSG for each patient.

Figure 12C:
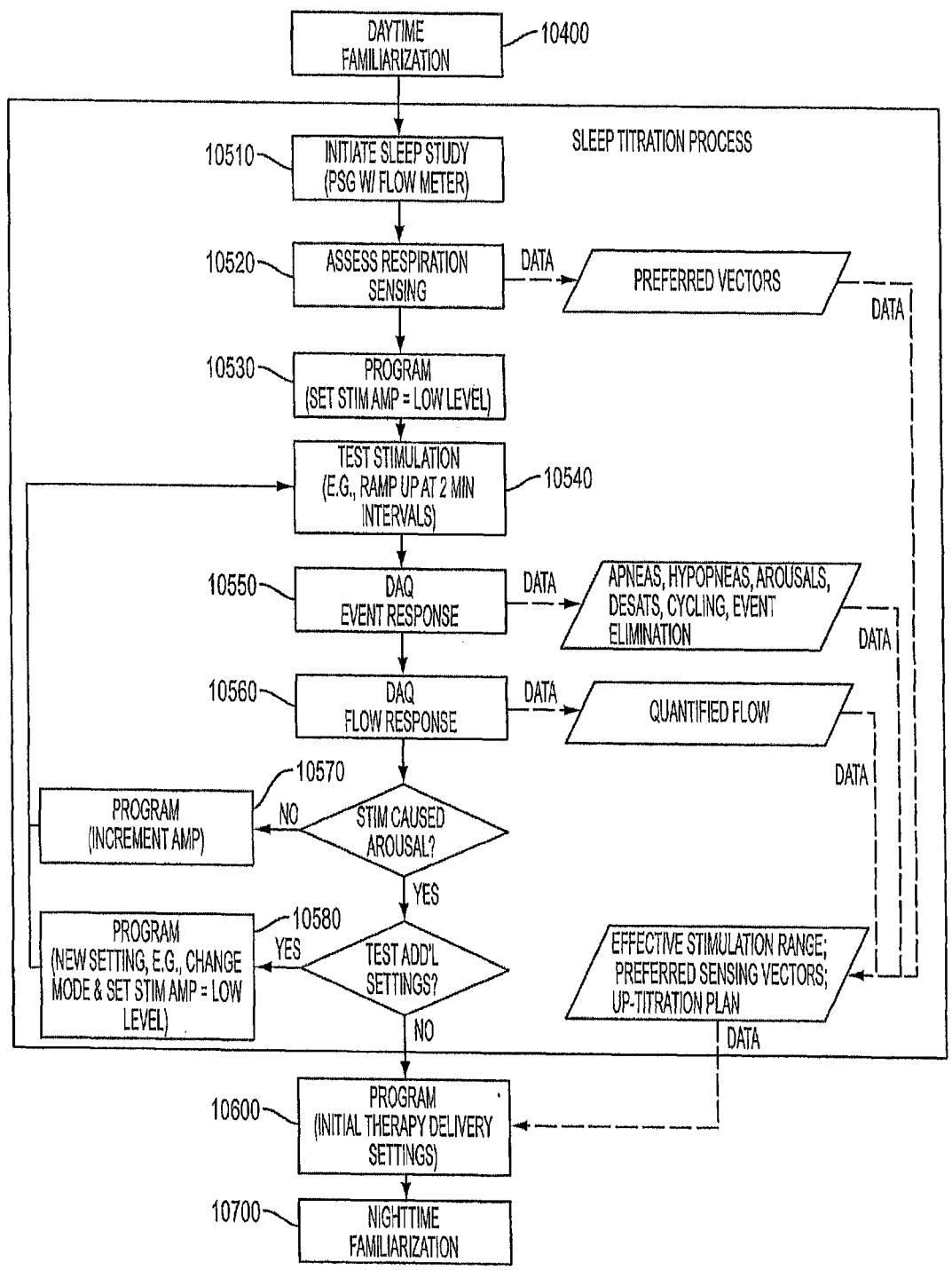

The sleep titration process is illustrated schematically in FIG. 12C. Titration generally involves establishing an effective range of stimulation settings 10540, where the lower end is defined by the lowest stimulation level where respiratory events (e.g., apneas, hypopneas, oxygen desaturations, etc.) 10550 begin to decrease or airflow begins to increase, and the range's upper end is defined by stimulation that arouses the patient. A goal setting at which the patient is effectively treated (i.e. respiratory events removed) may be estimated.

Figure 13:
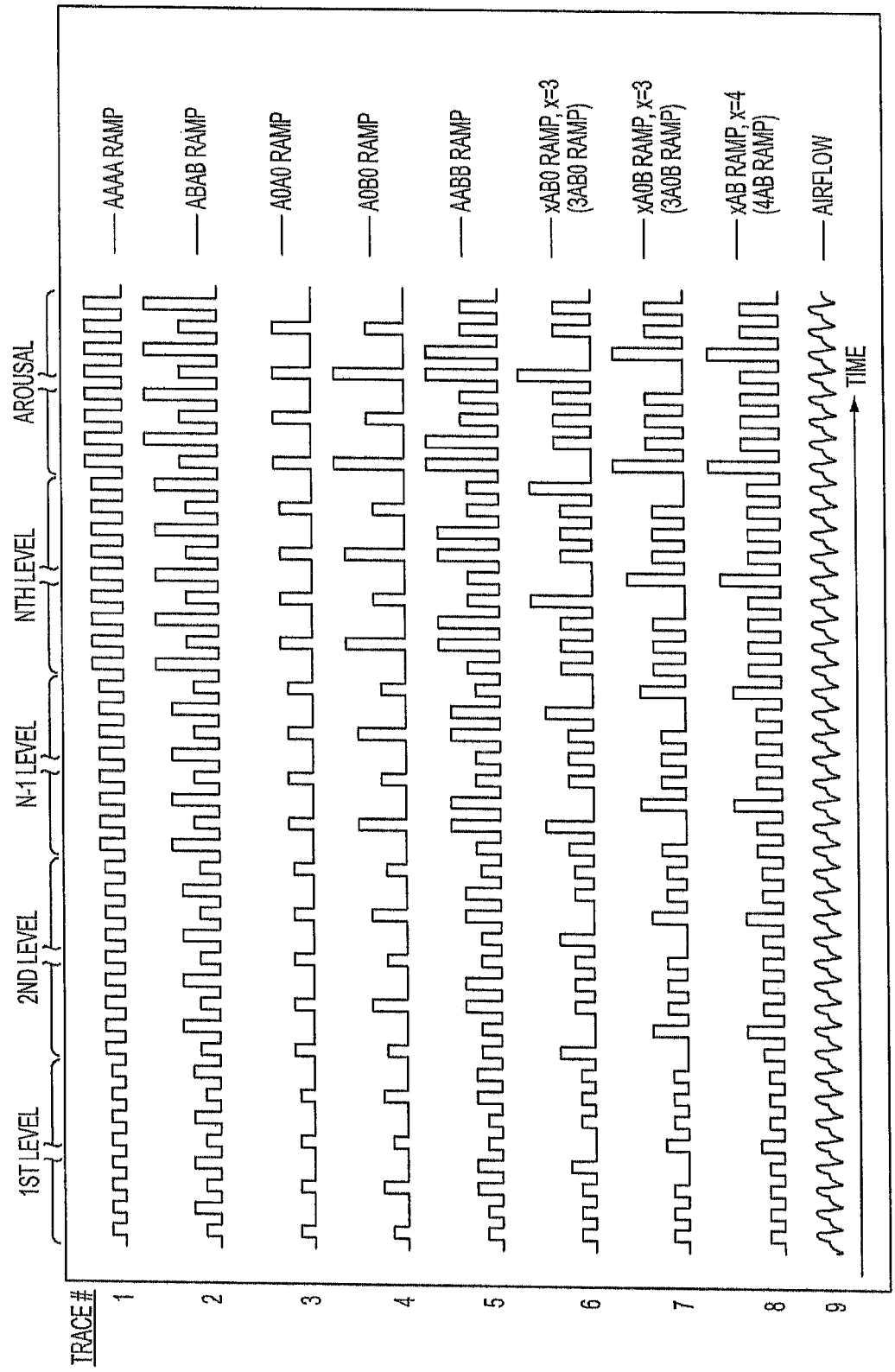
FIG. 13 (traces 1-9) illustrate various stimulation output modes of the implantable neurostimulator shown in FIG. 1.

During a sleep titration, device settings may be programmed using the programmer system 2100. At the start of titration, most stimulation settings will be at their default values (40 Hz frequency, 90 uS pulse width, 50% stimulation duty cycle, 0 ms phase adjust, etc.). Titration typically consists of many series of "ramps" in different body positions and sleep stages, wherein each ramp is a series of intervals where the stimulation intensity is increased from the previous interval in a certain stimulation mode 10540, illustrated in FIG. 13. For example, at 40 Hz, 90 uS, in A0A0 mode, stimulation level of the "A" breaths could be incremented every two minutes, from the nerve capture amplitude to the amplitude that causes arousal, as illustrated in FIG. 13 trace 3. Ramps are typically performed in A0A0, ABAB, AABB, A0B0, or AAAA modes, as illustrated in FIG. 13, traces 1, 2, 3, and 5. In addition, ramps may be performed using any of the previously discussed modes, also shown in FIG. 13. At each interval, observations are made as to whether stimulation causes arousal, reduces respiratory events, or increases airflow (e.g., increased $V_{i,max}$).

Alternative stimulation modes (not illustrated) may be utilized during wakefulness or sleep, (e.g. during a sleep titration PSG). An alternative mode may be xAy0 mode, where stimulation is delivered for "x" breaths wherein "x" is a programmable number of breaths, followed by "y" breaths with no stimulation wherein "y" is a programmable number of breaths. For example, in mode 4A40, stimulation is delivered on four consecutive breaths followed by no stimulation on four consecutive breaths.

A0A0 mode may be useful in determining if a stimulated breath has more flow than an adjacent unstimulated breath. In the same manner, ABAB and AABB modes may be useful in determining if a stimulated "A" breath provides more flow compared to an adjacent breath with less stimulation, "B." Likewise, A0B0 mode may be useful in comparing flows during "A" stimulation, "B" stimulations, and unstimulated breaths. During a ABAB, AABB, and A0B0 ramps, the difference in stimulation between "A" and "B" stimulations may be constant. ABAB, AABB, and AAAA ramps may also be useful in determining absolute flow (e.g., tidal volume, minute volume, etc.) and determining what level of stimulation reduces or eliminates respiratory events, since stimulation is delivered every breath. These observations may be recorded for future reference (e.g. physician use). Each stimulation mode may be combined with any of the pulse configurations, such as nested stimulation, soft start, or retention intensity, as chosen by physician or technician.

When a stimulation level is estimated to be efficacious, it may be tested in AAAA mode for a fixed time (e.g., five minutes) after which stimulation may be turned off for a fixed time (e.g., five minutes). If stimulation noticeably reduced or eliminated respiratory events compared to no stimulation, the settings may be considered the goal setting.

Additional titration PSG studies may be performed, either as a separate sleep study or as a split night study. In order to compare multiple stimulation settings during sleep, a crossover PSG study may be performed wherein the stimulation settings are changed at fixed intervals throughout the night, toggling through a select group of settings. For example, stimulation may alternate between two stimulation settings every five minutes. Afterwards, respiratory events may be determined for each interval such that an index (e.g., AHI, ODI, etc.) can be calculated for each stimulation setting. This may be useful to gauge whether an increase in stimulation would provide addition therapeutic benefits or to gauge whether a decrease in stimulation would not lessen any therapeutic benefits. In addition, the oxygen sensor of the INS 1100 may be used to measure oxygen de-saturations and calculate an ODI.

Another type of titration PSG may be a characterization night, per the methods of Schwartz et al., such that a Pcrit may be determined in REM/nREM sleep, both supine and lateral. Another type of sleep study is the home PSG study, which may be utilized to assess efficacy without the burden of an in-lab PSG. Many home PSG systems are available for use.

The patient may also undergo a vector-sweeping sleep study 10520, wherein the programming system 2100 and a respiratory signal (e.g., nasal cannula) are utilized. During this study, the secondary vector may be changed at regular intervals to cycle through a select group of vectors. These vectors are compared to the primary vector to determine an optimal sensing vector to deliver therapy. Selection may be based on maximum signal strength, consistent correlation to respiratory fiducials (e.g., offset of inspiration), and maximum signal stability/reliability across sleep stages, body positions, and disordered breathing events, for example. A stable signal has a minimum probability of signal inversion. A reliable signal has a minimum probability of signal loss, and may for example have a minimum threshold of 0.1 to 0.5 Ohms peak-to-peak, for example. The optimal vector may be selected by incrementally scrolling through all or a subset of possible vectors while sampling the respiration signal and comparing the signal against themselves or predefined thresholds. This scrolling technique may be performed manually (with inputs via the programmer system) or automatically (i.e., programmed). The sampling technique may also be performed manually (visual observation using programmer system) or automatically (i.e., programmed).

Post-Sleep-Titration: Nighttime Familiarization and Up-Titration

Figure 12D:
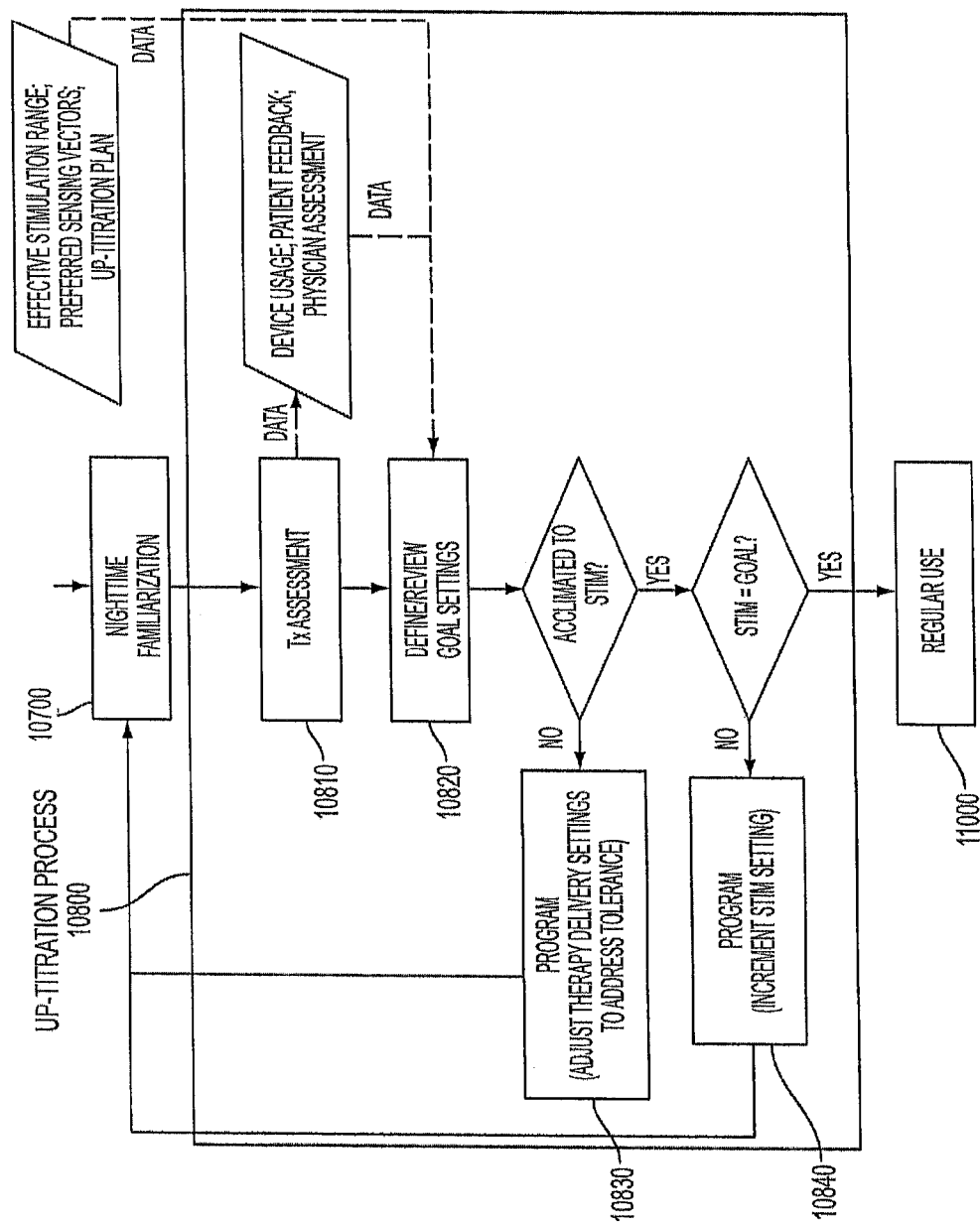

After titration, the patient is typically sent home with the device active and stimulation set to a level at which she can fall asleep. This begins the post-sleep-titration process, as illustrated in FIG. 12D. This process may include nighttime familiarization 10700, up-titration of stimulation 10800, and determining efficacy 11100.

The stimulation settings at which the patient is sent home may initially be below the estimated goal settings. As the patient becomes acclimated to sleeping with the device on 10700, stimulation may be slowly incremented, over the course of days, towards the range where therapeutic effects were observed during the sleep titration and ultimately towards the estimated goal settings. This period is known as up-titration 10800. These increments may be performed by a physician or caretaker, or by the patient, if the physician allows the patient to have limited control of stimulation via the therapy controller 2500.

Several feedback parameters may aid in determining the appropriate time to up-titrate a patient 10810. These include the device's therapy history of frequency and duration of therapy sessions, patient feedback (e.g., more daytime energy, no tongue abrasions, stimulation not causing arousal or pain, etc.), patient's bed-partner feedback (e.g., reduced snoring, perceives patient to be less sleepy, etc.), and most notably, a PSG study. Taken together, these may show whether the patient needs more time to acclimate to stimulation, is ready to have stimulation increased 10840, is receiving therapeutic benefits, or is fully treated. In addition, these feedback may provide data to adjust the patient's estimated goal settings 10820. For example, a patient's upper airway may, over time, undergo muscle remodeling such that less stimulation than originally estimated provides efficacious therapy. Alternatively, a patient may gain weight such that more stimulation than originally estimated may be needed to provide efficacious therapy.

If the stimulation is causing discomfort to the patient such that stimulation disrupts sleep or inhibits falling asleep with stimulation on, many options are available, 10830. Stimulation may be reduced and the patient may be given more time for nighttime familiarization. A different strategy that may increase the therapy provided to the patient is to utilize the device features of core hours, soft start, retention intensity, and nested stimulation. The core hours feature (FIG. 6K) allows the patient to fall asleep at one level of stimulation and after a programmable time interval, have stimulation increased to a more therapeutic level. Patients may be able to tolerate higher stimulations when asleep compared to wakefulness and in addition, tolerate higher stimulations further into a therapy session than at the start of a session.

As mentioned previously, the INS 1100 may be programmed to change stimulation level between therapy sessions, days, or other programmable value, enabling comparisons between stimulation level and therapy session data. For example, the INS 1100 may be programmed to alternate between 1.8 mA and 2.0 mA, where the change occurs between therapy sessions. This may be used as a diagnostic mode to assess the incremental benefit of the higher stimulation level. A patient receiving daily therapy would thus receive therapy at 1.8 mA on one day, 2.0 mA the next, 1.8 mA the next day, 2.0 mA the next day, and so on. This may allow therapy session data to be compared with stimulation level. For example, a physician may compare the cycling rate (via the cycling detector) during therapy sessions at 1.8 mA and 2.0 mA over time to determine if there is an observable difference. If cycling is reduced at 2.0 mA, the physician may increase stimulation and re-test. If there was no observable difference, the physician may decrease stimulation and re-test or simply set stimulation to the lower level. This may reduce the likelihood of delivering stimulation at a level that, compared to a lower level, provides no additional flow or no additional benefit. As mentioned previously, other therapy session data may be compared to stimulation level as well in a similar manner. Examples of other therapy session data are: oxygen desaturation frequency and severity, stimulation time, variations in respiratory rate, and variations in respiratory prediction.

Various pulse configurations may also help a patient acclimate to stimulation. The soft start stimulations (FIG. 6G) may provide a smoother transition from unstimulated breaths to stimulated breaths, reducing the patient's perception of stimulation intensity. Retention intensity (FIGS. 6E and 6F) may also provide therapy with reduced patient perception of stimulation intensity, since the full amplitude is only used for a part of the stimulation. Nested stimulations (FIG. 6H) may be used in a similar manner.

The patient may use positive airway pressure (PAP) therapy (e.g., CPAP, bi-PAP, auto-PAP, etc.) in conjunction with the neurostimulator. This may allow the patient to receive therapeutic benefits in addition to what is provided by the stimulation. The pressure necessary to provide these benefits may decrease as stimulation is up-titrated, 10800. This progress towards lower pressures may be monitored using the auto-PAP technology which automatically adjusts pressure to the level necessary to remove flow limitation. In time, the patient may wish to stop PAP therapy altogether. In a similar manner, other therapies such as but not limited to positional therapy and mandibular advancement may be used in conjunction with the neurostimulator.

If the patient begins noticing tongue abrasions, a tooth guard or other tooth covering (e.g. dental wax) may be used such that the tongue does not scrape against the teeth when stimulation causes tongue protrusion. Tooth guards may be custom-made (e.g., by a dentist).

Additional strategies for acclimation may include another sleep titration night to examine different stimulation frequencies, pulse widths, and modes, as previously described.

Different stimulation frequencies and pulse widths may capture different muscle groups in a more therapeutic manner. In additions, respiration vectors may need to be assessed during a vector sweeping titration.

Therapy efficacy may be measured using standard PSG techniques during and after familiarization and up-titration. Therapy efficacy may be evaluated by assessing indicia of sleep disordered breathing such as AHI, apnea index, hypopnea index, respiratory disturbance index, apnea-hypopnea index, ODI, FOSQ, ESS, BDI, PSQI, or other measures.

Alternative Embodiments

The stimulation may be delivered to the nerve by utilizing a variety of stimulation electrode configurations, in addition to the configurations previously mentioned.

Mono-polar stimulation may be delivered to the nerve wherein the cathode (or multiple cathodes) is an electrode (or multiple electrodes) in the STL nerve cuff 1350, and wherein the anode is the INS 1100. Similarly, far-field bi-polar stimulation may be delivered to the nerve wherein the cathode (or multiple cathodes) is an electrode (or multiple electrodes) in the nerve cuff, and wherein the anode is an RSL electrode 1250 or 1260.

Any combination of bi-polar and mono-polar stimulation may be utilized to deliver stimulation to the nerve. For example, mono-polar stimulation may be delivered between a cathode electrode in the STL nerve cuff 1350 and the INS 1100 anode. Simultaneously, far-field bi-polar stimulation may be delivered between a different cathode electrode in the STL nerve cuff 1350 and an RSL electrode 1250 or 1260 anode.

The INS 1100 may be programmed to periodically change stimulation parameters throughout a therapy session to vary which muscle fibers are recruited at any given time. For example, stimulation may be delivered at an initial lower frequency (e.g. 30 Hz) for 5 minutes, followed by stimulation delivered at a higher frequency (e.g. 50 Hz) for 2 minutes. Each frequency may have a unique pulse width, pulse width, and/or amplitude. This sequence could be repeated throughout the night.

This may allow certain muscle fibers to rest during periods when other muscle fibers are active. This may reduce muscle fatigue. In addition, stimulation at more than a single frequency and/or pulse width may be a more effective means of building muscle strength and endurance. Different stimulation settings (e.g. frequency, pulse width, and/or amplitude) may result in slightly different movement of the tongue. Varying stimulation settings may decrease the possibility of repetition-induced irritation, inflammation, or injury.

Alternatively, it may be possible to effectively build muscle strength and endurance by deactivating a portion of the nerve fibers and activating a remaining subset of fibers. This may allow delivery of higher levels of stimulation to the remaining fibers. This may reduce subject discomfort which could have occurred if all the fibers had been activated at that same intensity. Additionally, this may increase airway patency or opening by selecting muscles whose activation results in tongue protrusion and deactivating tongue retrusion muscles.

Certain fibers in the nerve may be selectively deactivated by choosing the cathode of pulse delivery and sequence of pulse delivery such that the fibers are not recruited by subsequent or simultaneous pulses. For example, a nerve fiber that innervates a retrusor muscle may be deactivated by delivering a sub-threshold pulse from a nearby cathode. This may allow a subsequent or simultaneous pulse at a different cathode to activate a nerve protrusor muscle nerve fiber without recruiting the retrusor muscle.

Any aspect set forth in any embodiment may be used with any other embodiment set forth herein. Every device and apparatus set forth herein may be used in any suitable medical procedure.

It will be apparent to those skilled in the art that various modifications and variations can be made in the disclosed methods and processes without departing from the scope of the disclosure. Other embodiments will be apparent to those skilled in the art from consideration of the specification and practice of the disclosure disclosed herein. It is intended that the specification and examples be considered as exemplary only, with a true scope and spirit of the disclosure being indicated by the following claims.

We claim:

1. A method of evaluating and treating a patient using a nerve stimulation device, the method comprising:
   receiving, by a server, preconditioned sleep data for analysis, the sleep data including a log of respiratory events for a sleep period of a patient, the sleep data further including blood oxygen data correlated with said respiratory events, wherein the blood oxygen data supports a mean oxygen desaturation value and an oxygen desaturation distribution curve, plotted against desaturation rate, having a slope between two points on the curve;
   comparing, by the server, at least one of the mean oxygen desaturation value or the slope of the oxygen desaturation distribution curve with a threshold;
   determining, by the server, that the at least one of the mean oxygen desaturation value or the slope of the oxygen desaturation distribution curve is below the threshold;
   providing, by the server, an indication that the patient is a candidate for the implantation of the nerve stimulation device to be displayed to a user via a user interface, the indication being based on the determination that the at least one of the mean oxygen desaturation value or the slope of the oxygen desaturation distribution curve is below the threshold;
   implanting the nerve stimulation device within the patient based on the indication; and
   delivering nerve stimulation therapy to the patient via the nerve stimulation device.

2. The method of claim 1, wherein the server includes a memory having reference sleep data compiled from a plurality of subjects, wherein the server compares the sleep data of the patient to the sleep data of the plurality of subjects to determine the indication.

3. The method of claim 1, wherein:
   the threshold for the mean oxygen desaturation value is 5%.

4. The method of claim 1, wherein the server compares the slope to the threshold to determine the indication.

5. The method of claim 4, wherein the indication is determined based on an absolute value of the slope being below the threshold.

6. The method of claim 1, wherein the indication further specifies that the patient is one of a strong responder or a borderline responder to the nerve stimulation therapy based on an analysis of the sleep data by the server.

7. The method of claim 1, wherein the sleep data is received by the server through a website, a mobile application, a software product, or a firmware product.

8. The method of claim 1, wherein the sleep data is received by the server by a sleep lab, a patient, and/or a user-operated sleep measurement device.

9. The method of claim 1, wherein the blood oxygen data is at least one of oxygen saturation data, oxygen desaturation data, SpO2 data, SaO2 data, or PaO2 data.

10. The method of claim 1, wherein:
the threshold for the mean oxygen desaturation value is at least one of 3%, 4%, 5%, 6%, 7%, or 8%.

11. The method of claim 1, wherein:
the threshold for the mean oxygen desaturation value is at least one of 6%, 7%, 8%, 9%, 10%, 11%, 12%, 13%, 14%, 15%, 16%, 17%, 18%, 19%, 20%, 21%, 22%, 23%, 24%, 25%.

12. The method of claim 1, wherein:
the threshold for the mean oxygen desaturation value is 8%.

13. The method of claim 1, wherein the threshold is determined based on mean oxygen desaturation values or slopes of oxygen desaturation distribution curves of a plurality of subjects.

14. The method of claim 13, wherein the plurality of subjects comprises a strong sub-group of subjects and an inadequate sub-group of subjects, the strong sub-group of subjects meeting an improvement criteria upon receiving a stimulation treatment from a nerve stimulation device and the inadequate sub-group of subjects not meeting the improvement criteria upon receiving a stimulation treatment from a nerve stimulation device.

15. A method of evaluating and treating a patient using a nerve stimulation device, the method comprising:
receiving, at a server configured to analyze sleep data, sleep data from a sleep lab, the sleep data including a log of respiratory events for a sleep period of a patient, the sleep data further including blood oxygen data correlated with said respiratory events, wherein the blood oxygen data supports a mean oxygen desaturation value and an oxygen desaturation distribution curve, plotted against desaturation rate, having a slope between two points on the curve;
comparing, by the server, at least one of the mean oxygen desaturation value or the slope of the oxygen desaturation distribution curve with a threshold;
determining, by the server, that the at least one of the mean oxygen desaturation value or the slope of the oxygen desaturation distribution curve is below the threshold;
determining, by the server that the patient is a candidate for the implantation of the nerve stimulation device based on the at least one of the mean oxygen desaturation value or the slope of the oxygen desaturation distribution curve being below the threshold;
providing, by the server, an output based on the sleep data, the output including an indication that the patient is a candidate for the implantation of the nerve stimulation device, wherein the output is configured to be displayed to a user;
implanting the nerve stimulation device within the patient based on the indication; and
delivering nerve stimulation therapy to the patient via the nerve stimulation device.

16. The method of claim 15, wherein the indication is determined by comparing the sleep data of the patient to reference sleep data compiled from a plurality of subjects.

17. The method of claim 15, wherein:
the threshold for the mean oxygen desaturation value is 5%.

18. The method of claim 15, wherein the indication is determined by comparing the slope to the threshold.

19. The method of claim 18, wherein the indication is determined based on an absolute value of the slope being below the threshold.

20. The method of claim 15, wherein the indication further specifies that the patient is one of a strong responder or a borderline responder to the nerve stimulation therapy based on an analysis of the sleep data.

21. The method of claim 15, wherein the sleep data is received from the sleep lab through a website, a mobile application, a software product, or a firmware product.

22. The method of claim 21, further comprising processing the sleep data received from the sleep lab at the website, the mobile application, the software product, or the firmware product to generate the output.

23. The method of claim 15, wherein the blood oxygen data is at least one of oxygen saturation data, oxygen desaturation data, SpO2 data, SaO2 data, or PaO2 data.

24. The method of claim 15, wherein:
the threshold for the mean oxygen desaturation value is at least one of 3%, 4%, 5%, 6%, 7%, or 8%.

25. The method of claim 15, wherein:
the threshold for the mean oxygen desaturation value is at least one of 6%, 7%, 8%, 9%, 10%, 11%, 12%, 13%, 14%, 15%, 16%, 17%, 18%, 19%, 20%, 21%, 22%, 23%, 24%, or 25%.

26. The method of claim 15, wherein:
the threshold for the mean oxygen desaturation value is 8%.

27. The method of claim 15, wherein the threshold is determined based on mean oxygen desaturation values or slopes of oxygen desaturation distribution curves of a plurality of subjects.

28. The method of claim 27, wherein the plurality of subjects comprises a strong sub-group of subjects and an inadequate sub-group of subjects, the strong sub-group of subjects meeting an improvement criteria upon receiving a stimulation treatment from a nerve stimulation device and the inadequate sub-group of subjects not meeting the improvement criteria upon receiving a stimulation treatment from a nerve stimulation device.

29. A method of evaluating and treating a patient using a nerve stimulation device, the method comprising:
receiving, at a server configured to analyze sleep data, sleep data from a blood oxygen monitor, the sleep data including a log of respiratory events for a sleep period of a patient, the sleep data further including blood oxygen data correlated with said respiratory events, wherein the blood oxygen data supports a mean oxygen desaturation value and an oxygen desaturation distribution curve, plotted against desaturation rate, having a slope between two points on the curve;
comparing, by the server, at least one of the mean oxygen desaturation value or the slope of the oxygen desaturation distribution curve with a threshold;
determining, by the server, that the at least one of the mean oxygen desaturation value or the slope of the oxygen desaturation distribution curve is below the threshold;
determining, by the server that the patient is a candidate for the implantation of the nerve stimulation device based on the at least one of the mean oxygen desaturation value or the slope of the oxygen desaturation distribution curve being below the threshold;
providing, by the server, an output based on the sleep data, the output including an indication that the patient is a candidate for the implantation of the nerve stimulation device, wherein the output is configured to be displayed to a user, implanting the nerve stimulation device within the patient based on the indication; and delivering nerve stimulation therapy to the patient via the nerve stimulation device.

30. The method of claim 29, wherein the indication is determined by comparing the sleep data of the patient to reference sleep data compiled from a plurality of subjects.

31. The method of claim 29, wherein:
the threshold for the mean oxygen desaturation value is 5%.

32. The method of claim 29, wherein the indication is determined by comparing the slope to the threshold.

33. The method of claim 32, wherein the indication is determined based on an absolute value of the slope being below the threshold.

34. The method of claim 29, wherein the indication further specifies that the patient is one of a strong responder or a borderline responder to the nerve stimulation therapy based on an analysis of the sleep data.

35. The method of claim 29, wherein the sleep data is received from the blood oxygen monitor through a website, a mobile application, a software product, or a firmware product.

36. The method of claim 35, further comprising processing the sleep data received from the blood oxygen monitor at the website, the mobile application, the software product, or the firmware product to generate the output.

37. The method of claim 29, wherein the blood oxygen data is at least one of oxygen saturation data, oxygen desaturation data, SpO2 data, SaO2 data, or PaO2 data.

38. The method of claim 29, wherein:
the threshold for the mean oxygen desaturation value is at least one of 3%, 4%, 5%, 6%, 7%, or 8%.

39. The method of claim 29, wherein:
the threshold for the mean oxygen desaturation value is at least one of 6%, 7%, 8%, 9%, 10%, 11%, 12%, 13%, 14%, 15%, 16%, 17%, 18%, 19%, 20%, 21%, 22%, 23%, 24%, or 25%.

40. The method of claim 29, wherein:
the threshold for the mean oxygen desaturation value is 8%.

41. The method of claim 29, wherein the threshold is determined based on mean oxygen desaturation values or slopes of oxygen desaturation distribution curves of a plurality of subjects.

42. The method of claim 41, wherein the plurality of subjects comprises a strong sub-group of subjects and an inadequate sub-group of subjects, the strong sub-group of subjects meeting an improvement criteria upon receiving a stimulation treatment from a nerve stimulation device and the inadequate sub-group of subjects not meeting the improvement criteria upon receiving a stimulation treatment from a nerve stimulation device.

43. A method of evaluating and treating a patient using a nerve stimulation device, the method comprising:
providing a programming device configured to communicate with one or more sensors configured to generate sleep data during a polysomnography evaluation;
receiving sleep data with the programming device, the sleep data including a log of respiratory events for a sleep period of a patient captured by the one or more sensors, the sleep data further including blood oxygen data correlated with said respiratory events, wherein the blood oxygen data supports a mean oxygen desaturation value and an oxygen desaturation distribution curve, plotted against desaturation rate, having a slope between two points on the curve;

comparing, by the programing device, at least one of the mean oxygen desaturation value or the slope of the oxygen desaturation distribution curve with a threshold;

determining, by the programming device, that the at least one of the mean oxygen desaturation value or the slope of the oxygen desaturation distribution curve is below the threshold;

determining, by the programming device, that the patient is a candidate for the implantation of the nerve stimulation device based on the at least one of the mean oxygen desaturation value or the slope of the oxygen desaturation distribution curve being below the threshold;

providing, by the programming device, an output based on the sleep data, the output including an indication that the patient is a candidate for the implantation of the nerve stimulation device;

displaying, via a display of the programming device, the indication to a user;

implanting the nerve stimulation device within the patient based on the indication; and delivering nerve stimulation therapy to the patient via the nerve stimulation device.

44. The method of claim 43, wherein the indication is determined by comparing the sleep data of the patient to reference sleep data compiled from a plurality of subjects.

45. The method of claim 43, wherein:
the threshold for the mean oxygen desaturation value is 5%.

46. The method of claim 43, wherein the indication is determined by comparing the slope to the threshold.

47. The method of claim 46, wherein the indication is determined based on an absolute value of the slope being below the threshold.

48. The method of claim 43, wherein the indication further specifies that the patient is one of a strong responder or a borderline responder to the nerve stimulation therapy based on an analysis of the sleep data.

49. The method of claim 43, wherein the sleep data is received from the programming device through a website, a mobile application, a software product, or a firmware product.

50. The method of claim 49, further comprising processing the sleep data received from the programming device at the website, the mobile application, the software product, or the firmware product to generate the output.

51. The method of claim 43, wherein the blood oxygen data is at least one of oxygen saturation data, oxygen desaturation data, SpO2 data, SaO2 data, or PaO2 data.

52. The method of claim 43, wherein:
the threshold for the mean oxygen desaturation value is at least one of 3%, less than 4%, less than 5%, less than 6%, less than 7%, or 8%.

53. The method of claim 43, wherein:
the threshold for the mean oxygen desaturation value is at least one of 6%, 7%, 8%, 9%, 10%, 11%, 12%, 13%, 14%, 15%, 16%, 17%, 18%, 19%, 20%, 21%, 22%, 23%, 24%, or 25%.

54. The method of claim 43, wherein:
the threshold for the mean oxygen desaturation value is 8%.

55. The method of claim 43, wherein the threshold is determined based on mean oxygen desaturation values or slopes of oxygen desaturation distribution curves of a plurality of subjects.

56. The method of claim 55, wherein the plurality of subjects comprises a strong sub-group of subjects and an inadequate sub-group of subjects, the strong sub-group of subjects meeting an improvement criteria upon receiving a stimulation treatment from a nerve stimulation device and the inadequate sub-group of subjects not meeting the improvement criteria upon receiving a stimulation treatment from a nerve stimulation device.

\* \* \* \* \*